United States Patent
Zalevsky et al.

(10) Patent No.: US 12,030,940 B2
(45) Date of Patent: Jul. 9, 2024

(54) IMMUNOTHERAPEUTIC TUMOR TREATMENT METHOD

(71) Applicant: Nektar Therapeutics, San Francisco, CA (US)

(72) Inventors: Jonathan Zalevsky, Berkeley, CA (US); Neel K. Anand, San Mateo, CA (US); Haiying Cai, Cupertino, CA (US); Bo-Liang Deng, San Ramon, CA (US); Zhongxu Ren, Foster City, CA (US); Bhalchandra V. Joshi, Madison, AL (US); Mary Tagliaferri, San Anselmo, CA (US); Werner Rubas, Redwood City, CA (US); Saul Kivimae, San Francisco, CA (US); Rhoneil L. Pena, Fremont, CA (US)

(73) Assignee: Nektar Therapeutics, San Francisco, CA (US)

( * ) Notice: Subject to any disclaimer, the term of this patent is extended or adjusted under 35 U.S.C. 154(b) by 519 days.

(21) Appl. No.: 16/639,520

(22) PCT Filed: Aug. 17, 2018

(86) PCT No.: PCT/US2018/000318
§ 371 (c)(1),
(2) Date: Feb. 14, 2020

(87) PCT Pub. No.: WO2019/036031
PCT Pub. Date: Feb. 21, 2019

(65) Prior Publication Data
US 2021/0130467 A1 May 6, 2021

Related U.S. Application Data
(60) Provisional application No. 62/546,896, filed on Aug. 17, 2017.

(51) Int. Cl.
*C07K 16/28* (2006.01)
*C07K 14/55* (2006.01)

(52) U.S. Cl.
CPC .......... *C07K 16/2818* (2013.01); *C07K 14/55* (2013.01)

(58) Field of Classification Search
CPC ............................ C07K 16/2818; C07K 14/55
See application file for complete search history.

(56) References Cited

U.S. PATENT DOCUMENTS

| 9,861,705 B2 | 1/2018 | Bossard et al. |
| 10,960,079 B2 | 3/2021 | Bossard et al. |

(Continued)

FOREIGN PATENT DOCUMENTS

| WO | WO 2010/019233 A1 | 2/2010 | |
| WO | WO-2010019233 A1 * | 2/2010 | ........... A61K 31/337 |

(Continued)

OTHER PUBLICATIONS

Wang et al. Antibody Structure, Instability, and Formulation Journal of Pharmaceutical Sciences, vol. 96, No. 1, Jan. 2007 (Year: 2007).*

(Continued)

*Primary Examiner* — Scarlett Y Goon
*Assistant Examiner* — Gabrielle A Small
(74) *Attorney, Agent, or Firm* — Jacqueline F. Mahoney

(57) ABSTRACT

Disclosed herein are methods in the field of cancer immunotherapy that involve the treatment of a subject having cancer by administering to the subject a toll-like receptor 7/8 (TLR7/8) agonist in combination with a long-acting IL-2Rβ-biased agonist and a programmed cell death protein 1 (PD-1)/programmed cell death protein ligand 1 (PD-L1) axis inhibitor, and related compositions, dosage forms, and kits.

28 Claims, 1 Drawing Sheet

(56) References Cited

U.S. PATENT DOCUMENTS

| | | |
|---|---|---|
| 2005/0281781 A1 | 12/2005 | Ostroff |
| 2008/0044438 A1 | 2/2008 | Ostroff et al. |
| 2016/0222060 A1 | 8/2016 | Miller et al. |
| 2019/0008978 A1 | 1/2019 | Huang et al. |
| 2021/0023230 A1 | 1/2021 | Bossard et al. |

FOREIGN PATENT DOCUMENTS

| | | | | |
|---|---|---|---|---|
| WO | WO 2012/065086 A1 | 5/2012 | | |
| WO | WO 2013/043647 A1 | 3/2013 | | |
| WO | WO 2013169693 A1 | 11/2013 | | |
| WO | WO 2015/125159 A1 | 8/2015 | | |
| WO | WO-2015125159 A1 * | 8/2015 | ......... | A61K 38/2013 |
| WO | WO 2017/019896 A1 | 2/2017 | | |
| WO | WO 2017/024296 A1 | 2/2017 | | |
| WO | WO-2017019896 A1 * | 2/2017 | ............. | A61K 39/00 |
| WO | WO 2017/079283 A1 | 5/2017 | | |
| WO | WO 2017/112741 A1 | 6/2017 | | |
| WO | WO 2018/078620 A1 | 5/2018 | | |
| WO | WO 2018/132496 A1 | 7/2018 | | |

OTHER PUBLICATIONS

Baheti et al. Excipients used in lyophilization of small molecules. J. Excipients and Food Chem. 1 (1) 2010 p. 41-54. (Year: 2010).*

Pasut and Veronese. PEG conjugates in clinical development or use as anticancer agents: An overview. Advanced Drug Delivery Reviews 61 (2009) 1177-1188 (Year: 2009).*

Milling et al Delivering safer immunotherapies for cancer. Advanced Drug Delivery Reviews(2017) 114: 79-101 (Year: 2017).*

Anz, et al., "Suppression of Intratumoral CCL22 by Type I Interferon Inhibits Migration of Regulatory T Cells and Blocks Cancer Progression", Cancer Research, vol. 75, No. 21, pp. 4483-4493, (2015).

Bacchi, et a., "Novel Synthetic Polyamines are Effective in the Treatment of Experimental Microsporidiosis, an Opportunistic AIDS-Associated Infection", Antimicrobial Agents and Chemotherapy, vol. 46, No. 1, pp. 55-61, (Jan. 2002).

Berge, et al., "Pharmaceutical Salts", Journal of Pharmaceutical Sciences, vol. 66, No. 1, pp. 1-19, (Jan. 1977).

Bohnhorst, et al., "Toll-like receptors mediate proliferation and survival of multiple myeloma cells", Leukemia, vol. 20, pp. 1138-1144, (2006).

Callahan, et al., "CTLA-4 and PD-1 pathway blockade: combinations in the clinic", Frontiers in Oncology, vol. 4, Article 385, pp. 1-6, (Jan. 2015).

Charych, et al., "Tipping the balance in the tumor microenvironment: An engineered cytokine (NKTR-214) with altered IL2 receptor binding selectivity and improved efficacy", Cancer Research, Abstract 482, Proceedings: AACR 104th Annual Meeting (2013).

Chi, et al., "Anti-tumor Activity of Toll-Like Receptor 7 Agonists", Frontiers in Pharmacology, vol. 8, Article 304, pp. 1-10, (May 2017).

Gupta et al., "Safety and pharmacodynamic activity of MEDI9197, TLR 7/8 agonist, administered intratumorally in subjects with solid tumors", Cancer Research, Abstract CT091, Proceedings: AACR Annual Meeting 2017 Washington, D.C., (Apr. 1-5, 2017).

Jego, et al., "Pathogen-associated molecular patterns are growth and survival factors for human myeloma cells through Toll-like receptors", Leukemia, vol. 20, pp. 1130-1137, (2006).

Kaczanowska, et al., "TLR agonists: our best frenemy in cancer immunotherapy", Journal of Leukocyte Biology, vol. 3, pp. 847-863, (2013).

Kiniwa, et al., "$CD8^+$ $Foxp3^+$ Regulatory T Cells Mediate Immunosuppression in Prostate Cancer", Clin. Cancer Res. vol. 13, No. 23, pp. 6947-6958, (Dec. 1, 2007).

Lu, et al., "TLR agonists for cancer immunotherapy: tipping the balance between the immune stimulatory and inhibitory effects", Frontiers in Immunology, vol. 5, Article 83, pp. 1-4, (Mar. 2014).

Mullins et al., "Intratumoral immunotherapy with TLR7/8 agonist MEDI9197 modulates the tumor microenvironment and holds potential for combination with immune checkpoint inhibitors", Cancer Research, Abstract 4697, Proceedings: AACR Annual Meeting 2017, Washington, D.C., (Apr. 1-5, 2017).

Nishii et al., "Combined treatment with PD-L1 blockade and a TLR7/8 agonist dramatically enhances antitumor immunity", Cancer Research, Abstract 563, Proceedings: AACR 107th Annual Meeting 2016, New Orleans, LA, (Apr. 16-20, 2016).

Varthaman, et al., "TLR3-Induced Maturation of Murine Dendritic Cells Regulates CTL Responses by Modulating PD-L1 Trafficking", PLOS One, vol. 11, No. 12, pp. 1-15, (Dec. 2, 2016).

Wolfle et al., "PD-L1 expression on tolerogenic APCs is controlled by STAT-3", Eur. J. Immunol., vol. 41, pp. 413-424, (2011).

Zhao, et al., "Combination therapy targeting toll like receptors 7, 8 and 9 eliminates large established tumors", Journal for Immuno Therapy of Cancer, vol. 2, No. 12, pp. 1-10, (2014).

PCT International Search Report and the Written Opinion corresponding to PCT Application No. PCT/US2018/000318 dated Feb. 15, 2019.

PCT International Preliminary Report on Patentability corresponding to PCT Application No. PCT/US2018/000318 dated Feb. 27, 2020.

Enzon Pharmaceuticals, Macromolecular Engineering Technologies, 16 pages, (2004).

Nektar™—Transforming Therapeutics, Nektar Molecule Engineering: Polyethylene Glycol and Derivatives for Advanced PEGylation, 24 pages, Catalog—2003, (Jul. 2003).

Nektar™—Transforming Therapeutics, Nektar Advanced PEGylation: Polyethylene Glycol and Derivatives for Advanced PEGylation, 27 pages, Catalog—2004, (Jul. 2004).

Nektar™—Transforming Therapeutics, Nektar Advanced PEGylation: Polyethylene Glycol and Derivatives for Advanced PEGylation, 33 pages, (Catalog 2005-2006).

NOF Corporation, PEG Derivatives, Phospholipid and Drug Delivery Materials for Pharmaceuticals, 46 pages, Catalogue 2003—1$^{st}$, (Jan. 2003).

NOF Corporation, PEG Derivatives, Phospholipid and Drug Delivery Materials for Pharmaceuticals, 27 pages, Catalogue 2003—2$^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

Aldara—imiquimod cream, Valeant Pharmaceuticals, North America LLC, 28 pages, Revised Aug. 2014.

(56) References Cited

OTHER PUBLICATIONS

European Examination Report corresponding to European Patent Application No. 18 792567.2 dated Mar. 6, 2023.

* cited by examiner

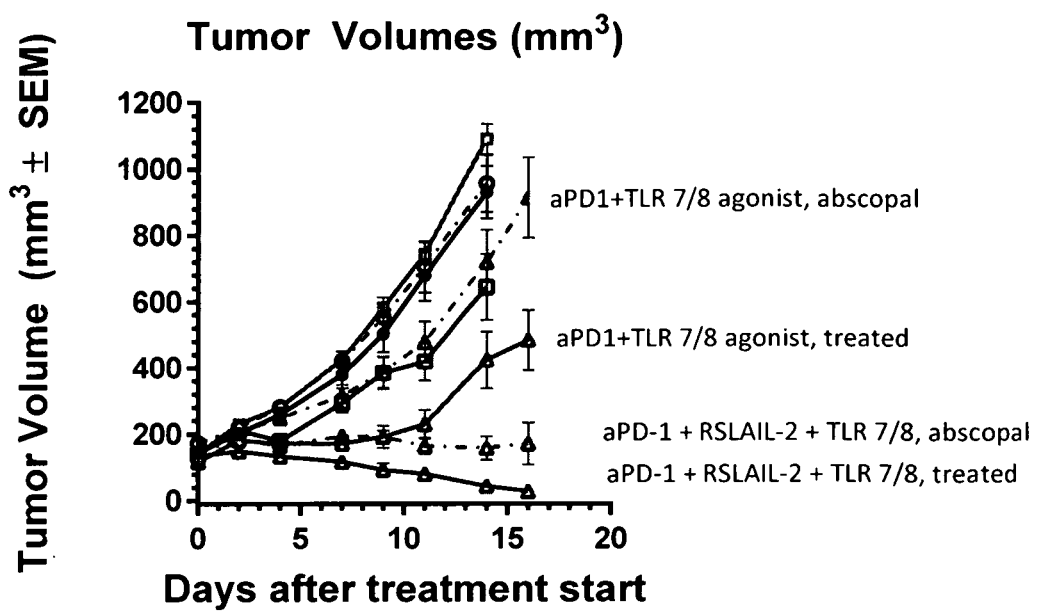

IMMUNOTHERAPEUTIC TUMOR TREATMENT METHOD

CROSS-REFERENCE TO RELATED APPLICATION

This application is a 35 U.S.C. § 371 application of International Application No. PCT/US2018/000318, filed Aug. 17, 2018, designating the United States, which claims the benefit of priority under 35 U.S.C. § 119(e) to U.S. Provisional Patent Application No. 62/546,896, filed on Aug. 17, 2017, the disclosure of which is incorporated herein by reference in its entirety.

FIELD

Described herein are (among other things) compositions comprising a programmed cell death protein 1 (PD-1)/programmed cell death protein ligand 1 (PD-L1) axis inhibitor in combination with an IL-2Rβ selective agonist, and/or a toll-like receptor (TLR) agonist, related formulations, systems and kits, therapeutic combinations, methods of treatment, and methods of making the compositions. Disclosures herein also relate to the field of cancer immunotherapy and involve, for example, the treatment of an individual having cancer by administering to the individual a programmed cell death protein 1 (PD-1)/programmed cell death protein ligand 1 (PD-L1) axis inhibitor in combination with a long-acting IL-2Rβ-biased agonist and/or a toll-like (TLR) receptor agonist.

BACKGROUND

The programmed cell death (PD-1) receptor is a member of the B7/CD28 family of costimulatory receptors. PD-1 is expressed on several cells including myeloid derived cells, B cells, and T cells. PD-1 regulates T cell activation through binding to its ligands, programmed cell death ligand 1 (PD-L1) and programmed cell death ligand 2 (PD-L2). PD-L1 is expressed in a number of cells including hematopoietic cells, leucocytes, and parenchymal cells. PD-L2 is expressed by dendritic cells and macrophages.

In the normal course, the PD-1 pathway plays a role in the control of T cell activity during an inflammatory response. Briefly, PD-1 receptor binding inhibits T cell proliferation; inhibits interferon-γ (IFN-γ), tumor necrosis factor-α (TNF-α), and interleukin-2 (IL-2) production; and reduces T cell survival. The PD-1 receptor on T cells binds PD-L1 expressed by antigen presenting cells (APCs) to thereby inhibit pro-inflammatory events such as T cell proliferation and cytokine production. Thus, the PD-1 checkpoint functions as a control over immune response hyperactivity.

A range of solid tumors have been found to upregulate expression of PD-L1 and/or PD-L2. Binding of the PD-1 ligands expressed on the tumor cell to the PD-1 receptor inhibits T cell proliferation, which blocks or reduces anti-tumor immune response (e.g., facilitates immune escape by the tumor cells).

PD-1 protein/programmed cell death protein ligand 1 (PD-L1) axis inhibitors can act as immune checkpoint blockade agents. PD-1/PD-L1 axis inhibitors block the interaction between PD-1 (CD 279) and its ligands, PD-L1 and PD-L2 and prevent suppression of T cell immunity. Administration of a PD-1/PD-L1 axis inhibitor can be effective to enhance T cell cytolytic activity. Administration of a PD-1/PD-L1 axis inhibitor can also be effective to support an immune stimulatory tumor microenvironment, help overcome immune suppression pathways in the tumor, and help support sustained systemic anti-tumor T cell response. For example, recent publications (Gupta et al., Phase I data on the Toll-like receptor 7/8 (TLR7/8) agonist MEDI9197 in solid tumors, Abstract #CT091, AACR 2017; Wölfle S J et al., PD-L1 expression on tolerogenic APCs is controlled by STAT-3. Eur J Immunol. 2011 February; 41(2):413-24) indicate that usage of TLR7/8 agonists resulted in induced up-regulation of PD-L1 in tumors in an IFN-dependent manner. Several PD-1/PD-L1 axis inhibitors are in various stages of clinical and non-clinical development.

Administration of IL-2Rβ-selective agonists has been suggested as being beneficial to patients suffering from certain cancers by targeting the adaptive immune system. Such administration is expected to reduce the immune-suppressing effects of regulatory T-cells while increasing CD8+ memory T-cells, to thereby recruit the patient's own immune system to eliminate cancer cells (see, for example, Charych et al., AACR 2013, Abstract #482).

Recruiting the immune system of a cancer patient in the treatment of cancer via administration of IL-2Rβ-selective agonists—which can be directly immunoactivating—can, in some cases, be further enhanced, for example, through the administration of additional agents. However, numerous challenges arise when trying to activate cytotoxic immune responses against tumors by administering more than one immunomodulating substance. For instance, in some cases, the administration of a second immunomodulator can actually attenuate or suppress rather than enhance the cytotoxic effect of a first immunomodulator, which when administered as a single agent (i.e., as a monotherapy) promotes a strong antitumor response. In cancer immunotherapy, achieving a favorable balance between immune stimulation and immune inhibition to provide an effective antitumor response, especially when administering multiple active agents, represents a significant challenge.

Besides targeting the adaptive immune system, stimulators of the innate immune system can also be administered to treat cancer. For example, Toll-like receptors (TLRs), due to their strong immune stimulatory capacity, have been investigated. TLRs are primarily expressed by cells belonging to the innate immune systems' arm, that is, dendritic cells (DCs) and monocytes. Although TLRs are functionally expressed in several types of tumors, they can act to exert both positive and negative effects on carcinogenesis. TLRs comprise a family of highly conserved germline-encoded pattern recognition receptors that detect pathogen-associated molecular patterns (PAMPs) expressed by a variety of infectious organisms. TLRs trigger the innate immune system and bolster adaptive immunity against antigens expressed by pathogens and tumors. At least 13 different TLRs have been identified in mammals (Zhao, G., et al., *Journal for ImmunoTherapy of Cancer* 2014, 2:12). TLR1, -2, -4, -5, -6, and -10 are expressed on the cell surface, while TLR-3, -7, -8, and -9 are situated on endosomal membranes within the cell. (Kaczanowska, S., et al., *J. Leukoc Biol.* 2013 June; 93(6):847-863). TLRs are sensors detecting pathogen and malignant cell-derived molecules called pathogen-associated molecular patterns (PAMPs) which, upon binding to TLRs, trigger the nuclear factor (NF)-κB and type I interferon pathways resulting in the production of pro-inflammatory cytokines in dendritic cells (DCs) and other antigen presenting cells such as macrophages. TLRs are crucial for stimulation of DC maturation, antigen uptake and presentation, and the differentiation of $CD4^+$ cells and control of regulatory T (Treg) cells.

TLRs-7, -8, and -9 are similar in their recognition of nucleic acid motifs and expression within endosomal compartments (Zhao, G., 2014, ibid). Several ligands, both synthetic and natural nucleosides, have been characterized as TLR7 and/or TLR8 ligands. Recognition of these nucleoside ligands by TLR7 or TLR8 receptors activates intracellular pathways that culminate in the induction of proinflammatory cytokines, chemokines, and type I interferons (IFNs), and in the upregulation of co-stimulatory molecules. TLRs are type I membrane proteins, characterized by an ectodomain composed of leucine-rich repeats, responsible for recognition of pathogen-associated molecular patterns, and a cytoplasmic domain, called the Toll/interleukin-1 receptor (TIR) domain, which is required for downstream signaling. TLR7 and TLR8 are closely related, sharing their intracellular endosomal location, as well as their ligands. Recognition of a ligand by TLR7 or TLR8 is followed by recruitment of the TLR domain—containing adaptor molecule myeloid differentiation primary response gene 88 (MyD88). The association of TLR7/8 and MyD88 stimulates the recruitment of members of the interleukin-1 receptor-associated kinase family, resulting in the downstream activation of mitogen-activated protein kinases (MAPKs) and the IκB kinase (IKK) complex. Toll-like receptor agonists of TLR 7 and TLR 8 activate macrophages and can, in some instances, change the tumor environment from a tumor-promoting to a tumor-suppressive (inflammatory) environment.

In light of their potential ability to activate several cell types such as DCs, monocytes, macrophages, fibroblasts, and human keratinocytes, induce apoptosis, generate enhanced immunogenicity and sensitization to killing mediated by cytotoxic T-cell lymphocytes and chemotherapeutics, TLR ligands are considered to be a class of immune-response modifiers having the potential to generate an effective antitumor immune response. Furthermore, TLR-8 ligands have been shown to reverse the suppressive function of CD8+ Treg cells (Kiniwa Y., et al., *Clin Cancer Res* 2007; 13:6947-58). Moreover, the application of TLR8 ligands resulted in a reduction of tumor infiltrating Foxp3$^+$ Treg cells changing the tumor environment from tumor promoting to tumor suppressive (Anz D. et al., *Cancer Res.* 2015; 75:4483-93). On the other hand, TLR activation has, in certain instances, been shown to be advantageous for the proliferation, invasiveness, and/or survival of tumor cells (see, e.g., Bohnhorst J., et al., *Leukemia* 2006; 20:1138-1144; and Jego G., et al., *Leukemia* 2006; 20:1130-1137). Certain TLR 7/8 agonists have also been shown to induce immunosuppression and autoimmune disease (Chi H., et al., *Frontiers in Pharmacology.* 2017; 8:304).

TLR agonists have been investigated for their antitumor properties, however, in general, most TLR agonists have underperformed as cancer therapeutics. TLR agonists have been investigated for their antitumor properties; however, in general, most TLR agonists have underperformed as cancer therapeutics. It has been postulated that such underperformance might be explained by a mechanism in which induction of immune suppressive factors dampens TLR-agonist-induced inflammation. (Lu, H., *Frontiers in Immunology*, March 2014, 5, 83). For example, TLR agonists have immune stimulatory effects through the induction of co-stimulatory molecules such as CD80, CD86, and CD40 on dendritic cells and inflammatory cytokines such as TNF-α and IL-12 that polarize the immune response. However, TLR agonists also have immune inhibitory effects, e.g., by inducing several immune suppressive factors including IL-10, regulatory T cells (Tregs), and PD-1, all of which can suppress anti-tumor immunity (Lu, H., 2014, ibid). Thus, a notable challenge exists in trying to arrive at an immunotherapeutic combination in which all components interact favorably to provide an enhanced therapeutic effect.

As discussed above, although there have been substantial efforts in developing effective cancer immunotherapies encompassing various platforms to date, there remains a need to identify and provide new and more effective immunotherapeutic treatment regimens, for example, for treating cancer. The present disclosure seeks to address this and other needs.

A number of aspects and embodiments are described herein. As such, each of the features and embodiments described herein, even if not explicitly stated, is meant to be applicable (but is not required to be applicable) to any other aspect, embodiment or feature or combination of features, unless stated to the contrary.

SUMMARY

Administering a programmed cell death protein 1 (PD-1)/programmed cell death protein ligand 1 (PD-L1) axis inhibitor in combination with a long-acting IL-2Rβ-biased agonist and/or a TLR agonist can result in synergy in non-overlapping complementary mechanisms stimulating innate and adaptive arms of the immune system leading to an effective immuno-oncology (IO) therapy. Moreover, efficient utilization of multiple immune targeting pathways may optimize efficacy and/or minimize toxicities by avoiding overlapping mechanisms of action that exacerbate immune-mediated adverse events. The complementary biological mechanisms of a PD-1/PD-L1 axis inhibitor targeting checkpoint blockade with a long-acting IL-2Rβ-biased agonist targeting the adaptive immune system and lymphoid cell pathways, and/or a TLR agonist targeting the innate immune system and myeloid cell pathways, are ideal to synergistically activate the immune system to enhance efficacy.

In a first aspect, provided herein is a method comprising administering to a subject having cancer a PD-1/PD-L1 axis inhibitor in combination with an IL-2Rβ-activating amount of along-acting IL-2Rβ-biased agonist and/or a TLR agonist, each of which described in greater detail herein.

In another aspect, provided herein is a method comprising administering to a subject having cancer, a PD-1/PD-L1 axis inhibitor and an IL-2Rβ-activating amount of a long-acting IL-2Rβ-biased agonist.

In another aspect, provided herein is a method comprising administering to a subject having cancer, a PD-1/PD-L1 axis inhibitor and a TLR agonist.

In another aspect, provided herein is a method comprising administering to a subject having cancer, a PD-1/PD-L1 axis inhibitor, an IL-2Rβ-activating amount of a long-acting IL-2Rβ-biased agonist, and a TLR agonist.

By way of clarity, with regard to the sequence of administering, the PD-1/PD-L1 axis inhibitor, the TLR agonist, and the long-acting IL-2Rβ-biased agonist may be administered concurrently or sequentially and in any order, and via the same and/or different routes of administration, each in an immunomodulating amount. Moreover, treatment may comprise a single cycle of therapy, or can comprise multiple (i.e., two or more) cycles of therapy. Additional cycles of therapy can include administration of each of the PD-1/PD-L1 axis inhibitor, the TLR agonist, and the long-acting IL-2Rβ-biased agonist, or administration of a subset thereof, and this disclosure is not limited in this regard.

In one or more embodiments, relating to any one of the foregoing aspects, the TLR7/8 agonist is administered locally. Additionally, in one or more embodiments related to any one or more of the foregoing aspects, the long-acting IL-2Rβ-biased agonist is administered parenterally. In yet one or more further embodiments related to any one or more of the foregoing aspects, the PD-1/PD-L1 axis inhibitor is administered parenterally. In one or more related embodiments, the TLR agonist is administered directly to the site of a tumor. In some applicable embodiments, the PD-1/PD-L1 axis inhibitor and the long-acting IL-2Rβ-biased agonist are administered concurrently or even as components of a single formulation.

In one or more embodiments related to any one or more of the foregoing aspects, the PD-1/PD-L1 axis inhibitor, the long-acting IL-2Rβ-biased agonist and/or the TLR agonist, e.g., a multi-armed polymer conjugate of a TLR 7/8 agonist, are administered separately from each other. In yet one or more further embodiments, the TLR agonist is administered to the subject prior to administering the long-acting IL-2Rβ-biased agonist and/or the PD-1/PD-L1 axis inhibitor. In one or more alternative embodiments, the TLR agonist is administered on day 1 of treatment and the long-acting IL-2Rβ-biased agonist and/or the PD-1/PD-L1 axis inhibitor are administered on any one of days 1 to 4 of treatment. For example, the long-acting IL-2Rβ-biased agonist and the PD-1/PD-L1 axis inhibitor are administered on any one of days 1, 2, 3, or 4 of treatment. In some embodiments, the PD-1/PD-L1 axis inhibitor, the long-acting IL-2Rβ-biased agonist, and the TLR agonist are administered together on at least one day of the treatment regimen.

In one or more embodiments related to any one or more of the foregoing aspects, the PD-1/PD-L1 axis inhibitor, the long-acting IL-2Rβ-biased agonist and the TLR agonist are administered concurrently with each other. For example, in one or more embodiments, the PD-1/PD-L1 axis inhibitor, the long-acting IL-2Rβ-biased agonist, and/or the TLR agonist are administered on day 1 of treatment.

In one or more embodiments related to any one or more of the foregoing aspects, the PD-1/PD-L1 axis inhibitor, the long-acting IL-2Rβ-biased agonist and/or the TLR7/8 agonist are administered in the same formulation.

In one or more embodiments related to any one or more of the foregoing aspects, the PD-1/PD-L1 axis inhibitor and the TLR agonist are administered concurrently with each other. For example, in one or more embodiments, the PD-1/PD-L1 axis inhibitor and the TLR agonist are administered on day 1 of treatment. In one or more embodiments, the PD-1/PD-L1 axis inhibitor and the TLR agonist are administered in the same formulation.

In one or more embodiments related to any one or more of the foregoing aspects, the PD-1/PD-L1 axis inhibitor and the long-acting IL-2Rβ-biased agonist are administered concurrently with each other. For example, in one or more embodiments, the PD-1/PD-L1 axis inhibitor and the long-acting IL-2Rβ-biased agonist are administered on day 1 of treatment. In one or more embodiments, the PD-1/PD-L1 axis inhibitor and the long-acting IL-2Rβ-biased agonist are administered in the same formulation.

In a preferred embodiment, the subject is a human subject.

In one or more additional embodiments, the cancer is a solid cancer. For example, in one or more embodiments, the cancer is selected from the group consisting of breast cancer, ovarian cancer, colon cancer, prostate cancer, bone cancer, colorectal cancer, gastric cancer, lymphoma, malignant melanoma, liver cancer, small cell lung cancer, non-small cell lung cancer, pancreatic cancer, thyroid cancers, kidney cancer, cancer of the bile duct, brain cancer, cervical cancer, maxillary sinus cancer, bladder cancer, esophageal cancer, Hodgkin's lymphoma, and adrenocortical cancer.

In some embodiments, the long-acting IL-2Rβ-biased agonist comprises aldesleukin releasably covalently attached to polyethylene glycol. In yet some additional embodiments, the long-acting IL-2Rβ-biased agonist comprises aldesleukin releasably covalently attached to from 4, 5, and 6 polyethylene glycol polymers. In yet some further embodiments, the long-acting IL-2Rβ-biased agonist comprises aldesleukin releasably covalently attached to an average of about 6 polyethylene glycol polymers. In one or more additional embodiments, the polyethylene glycol polymers that are releasably, covalently attached to aldesleukin are branched. In yet one or more particular embodiments, the long-acting IL-2Rβ-biased agonist is multi(2,7-(bis-methoxyPEG-carboxyamide)(9H-fluorene-9-yl)methyl N-carbamate)interleukin-2, such as for example, (2,7-(bis-methoxyPEG$_{10kD}$-carboxyamide)(9H-fluorene-9-yl)methyl N-carbamate)$_{4-6}$interleukin-2. In yet one or more additional embodiments, the long-acting IL-2Rβ-biased agonist is (2,7-(bis-methoxyPEG-carboxyamide)(9H-fluorene-9-yl)methyl N-carbamate)$_{6\ avg}$interleukin-2.

In yet some further embodiments related to any one or more of the foregoing aspects or embodiments, the TLR agonist is a TLR-7 agonist or a TLR 8 agonist. In one or more embodiments, the TLR agonist is a TLR-7 agonist. In yet one or more alternative embodiments, the TLR agonist is a TLR-8 agonist. In some embodiments, the TLR7/8 agonist is a long-acting TLR agonist such as a long-acting TLR-7 or a long-acting TLR-8 agonist (e.g., a multi-armed polymer modified TLR-7 or TLR-8 agonist).

In yet some additional embodiments, the long-acting TLR agonist is a multi-armed water-soluble polymer conjugate of a TLR agonist such as a TLR7/8 agonist. In yet one or more further embodiments, the multi-armed water-soluble polymer is stably covalently linked to the TLR agonist, e.g., a TLR7/8 agonist.

In one or more alternative embodiments, the multi-armed water-soluble polymer is releasably covalently linked to the TLR agonist. In yet one or more particular embodiments, the long-acting TLR agonist is a 4-arm-pentaerythritolyl-based polyethylene glycol conjugate having a TLR agonist molecule covalently linked, either stably or releasably, at the terminus of each of its four polymer arms, optionally through an intervening spacer or linker moiety. In some embodiments related to the TLR agonist, the TLR agonist is imiquimod or resiquimod. In yet some further embodiments, the TLR agonist is resiquimod. In one or more particular embodiments, the TLR agonist is a 4-arm-PEG20kD-CM-glycine-N-R848, where R848 is a synonym for resiquimod (1-[4-Amino-2-(ethoxymethyl)-1H-imidazo[4,5-c]quinolin-1-yl]-2-methylpropan-2-ol).

In yet some further embodiments related to any one or more of the foregoing aspects or embodiments, the PD-1/PD-L1 axis inhibitor is an antibody. In yet some further embodiments related to any one or more of the foregoing aspects or embodiments, the PD-1/PD-L1 axis inhibitor is a human monoclonal antibody. In one or more embodiments, the PD-1/PD-L1 axis inhibitor is atezolizumab (available from Genentech as TENCENTRIQ®), avelumab (available from Merck KGaA and Pfizer as BAVENCIO®), durvalumab (available from AstraZeneca as IMFINZI®), nivolumab (available from Bristol-Myers Squibb as OPDIVO®), pembrolizumab (available from Merck as KEYTRUDA®), or tislelizumab (BeiGene BGB-A317).

Pembrolizumab and nivolumab are PD-1 inhibitors while atezoluzumab, avelumab and durvalumab are PD-L1 inhibitors.

In some embodiments, the combination therapy comprises administration of a PD-1/PD-L1 axis inhibitor and 4-arm-PEG20kD-CM-glycine-N-R840 or (2,7-(bis-methoxyPEG$_{10kD}$-carboxyamide)(9H-fluorene-9-yl)methyl N-carbamate)$_{4-6}$interleukin-2. In some further embodiments, the combination therapy comprises administration of a PD-1/PD-L1 axis inhibitor in combination with 4-arm-PEG20kD-CM-glycine-N-R848 and (2,7-(bis-methoxyPEG$_{10kD}$-carboxyamide)(9H-fluorene-9-yl)methyl N-carbamate)$_{4-6}$interleukin-2. In some further embodiments, the PD-1/PD-L1 axis inhibitor is nivolumab. In yet some additional embodiments, the PD-1/PD-L1 axis inhibitor is pembrolizumab.

In some embodiments of any one or more aspects of the method of administering, the administering is effective to produce an abscopal effect in the subject.

In yet a further aspect, provided is a kit comprising a T cell stimulatory amount of a PD-1/PD-L1 axis inhibitor, an IL-2Rβ-activating amount of a long-acting IL-2Rβ-biased agonist, and/or an innate immunity activating amount of a TLR agonist, accompanied by instructions for use in treating a subject having cancer.

In yet a further aspect, provided is a kit comprising a T cell stimulatory amount of a PD-1/PD-L1 axis inhibitor and an IL-2Rβ-activating amount of a long-acting IL-2Rβ-biased agonist, accompanied by instructions for use in treating a subject having cancer.

In yet a further aspect, provided is a kit comprising a T cell stimulatory amount of a PD-1/PD-L1 axis inhibitor and an innate immunity activating amount of a TLR agonist, accompanied by instructions for use in treating a subject having cancer.

In some embodiments of the kits, the PD-1/PD-L1 axis inhibitor, the long-acting IL-2Rβ-biased agonist, and/or the TLR agonist are comprised in a single composition for administration to the subject, where the singe composition optionally comprises a pharmaceutically acceptable excipient. In one or more further embodiments of the kit, the PD-1/PD-L1 axis inhibitor and the long-acting IL-2Rβ-biased agonist are comprised in a single composition for administration to the subject, where the kit optionally further comprises an additional separate composition comprising the TLR agonist, i.e., for administration to the subject, each separate composition optionally comprising one or more pharmaceutically acceptable excipients.

In some alternative embodiments of the kit, each of the PD-1/PD-L1 axis inhibitor, the long-acting IL-2Rβ-biased agonist, and/or the TLR agonist is provided in separate containers, and the kit comprises instructions for administering each of the PD-1/PD-L1 axis inhibitor, the TLR agonist, and/or the long-acting IL-2Rβ-biased agonist separately to the subject.

In some embodiments of the kit, each of the PD-1/PD-L1 axis inhibitor, the long-acting IL-2Rβ-biased agonist, and/or the TLR agonist is in solid form. In one or more related embodiments, each of the PD-1/PD-L1 axis inhibitor, the long-acting IL-2Rβ-biased agonist, and/or the long-acting TLR agonist is in a solid form suitable for reconstitution in an aqueous diluent.

In yet one or more further embodiments, each of the PD-1/PD-L1 axis inhibitor, the long-acting IL-2Rβ-biased agonist, and/or the TLR agonist is comprised within separate compositions each comprising a pharmaceutically acceptable excipient.

Additional aspects and embodiments are set forth in the following description and claims.

BRIEF DESCRIPTION OF THE DRAWINGS

FIG. 1 is a plot of mean tumor volumes (mm$^3$) in mice over a time course of 16 days following treatment with various immunotherapeutic agents and combinations thereof in an EMT6 tumor model, where the treatment groups included (i) a PD-1 antibody (aPD-1) (■), (ii) aPD-1+an exemplary long acting IL-2 agonist, "RSLAIL-2" (□), (iii) aPD-1+TLR 7/8 agonist treated right flank (Δ, solid line), (iv) aPD-1+TLR 7/8 agonist abscopal left flank (Δ, dashed line), (v) aPD-1+RSLAIL-2+TLR 7/8 agonist treated right flank (▲, solid line), (vi) aPD-1+RSLAIL-2+TLR 7/8 agonist abscopal flank (▲, dashed line), (vii) vehicle treated right flank (●), (viii) vehicle untreated left flank (○), which study is further described in Example 19.

DETAILED DESCRIPTION

Definitions

In describing and claiming certain features of this disclosure, the following terminology will be used in accordance with the definitions described below unless indicated otherwise.

As used in this specification, the singular forms "a," "an," and "the" include plural referents unless the context clearly dictates otherwise.

"Water-soluble, non-peptidic polymer" indicates a polymer that is at least 35% (by weight) soluble, preferably greater than 70% (by weight), and more preferably greater than 95% (by weight) soluble, in water at room temperature. Typically, an unfiltered aqueous preparation of a "water-soluble" polymer transmits at least 75%, more preferably at least 95%, of the amount of light transmitted by the same solution after filtering. It is most preferred, however, that the water-soluble polymer is at least 95% (by weight) soluble in water or completely soluble in water. With respect to being "non-peptidic," a polymer is non-peptidic when it has less than 35% (by weight) of amino acid residues.

The terms "monomer," "monomeric subunit" and "monomeric unit" are used interchangeably herein and refer to one of the basic structural units of a polymer. In the case of a homo-polymer, a single repeating structural unit forms the polymer. In the case of a co-polymer, two or more structural units are repeated—either in a pattern or randomly—to form the polymer. Preferred polymers are homo-polymers. The water-soluble, non-peptidic polymer comprises one or more monomers serially attached to form a chain of monomers. The polymer can be formed from a single monomer type (i.e., is homo-polymeric) or two or three monomer types (i.e., is co-polymeric).

A "polymer" as used herein is a molecule possessing from about 2 to about 4000 or more, e.g. from about 2 to about 2000, monomers. Specific polymers include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG polymer" or any polyethylene glycol is one in which substantially all (preferably all) monomeric subunits are ethylene oxide subunits, though, the polymer may contain distinct end capping moieties or functional groups, e.g., for conjugation. PEG polymers may comprise one of the two following structures:

—(CH$_2$CH$_2$O)$_n$— or —(CH$_2$CH$_2$O)$_{n-1}$CH$_2$CH$_2$—, depending upon whether or not the terminal oxygen(s) has been displaced, e.g., during a synthetic transformation. As stated above, for the PEG polymers, the variable (n) (i.e. number of repeat units) ranges from about 2 to 2000, or from about 2 to 4000, and the terminal groups and architecture of the overall PEG can vary. When PEG further comprises a functional group for linking to, e.g., a small molecule or to a protein, the functional group when covalently attached to a PEG polymer does not result in formation of an oxygen-oxygen bond (—O—O—, a peroxide linkage).

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy or an alkaaryloxy group. Thus, examples of end-capping moieties include alkoxy (e.g., methoxy and, ethoxy), benzyloxy, as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

The term "targeting moiety" refers to a molecular structure that helps the conjugates to localize to a targeting area, e.g., help enter a cell, or bind a receptor. Preferably, the targeting moiety comprises a vitamin, antibody, antigen, receptor, DNA, RNA, sialyl Lewis X antigen, hyaluronic acid, sugars, cell-specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When a polymer conjugate has a targeting group comprising a detectable label, the amount and/or distribution/location of the polymer and/or the moiety (e.g., active agent) to which the polymer is conjugated can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques (e.g., gel filtration chromatography). Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation, MALDI TOF, or viscometry to determine weight average molecular weight. PEG polymers are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

"Branched," in reference to the geometry or overall structure of a polymer, refers to a polymer having two or more polymer "arms" or "chains" extending from a branch point.

"Forked", in reference to the geometry or overall structure of a polymer, refers to a polymer having two or more functional groups (typically through one or more atoms) extending from a branch point.

A "branch point" refers to a bifurcation point comprising one or more atoms at which a polymer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group that is being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "releasable linkage" is a relatively labile bond that cleaves under physiological conditions, wherein the cleavage may occur by way of any of a number of different mechanisms. One type of exemplary releasable linkage is a hydrolysable bond, that is, one that cleaves upon reaction with water (i.e., is hydrolyzed), e.g., under physiological conditions, such as for example, hydrolysis of an amide bond such as an aromatic amide bond. The tendency of a bond to hydrolyze in water may depend not only on the general type of linkage connecting two atoms but also on the substituents attached to these atoms. Exemplary hydrolytically unstable or weak linkages may include but are not limited to carboxylate ester, phosphate ester, anhydrides, acetals, ketals, acyloxyalkyl ether, imines, orthoesters, peptides, oligonucleotides, thioesters, and carbonates. Releasable linkages also include enzymatically releasable linkages, where an "enzymatically releasable linkage" means a linkage that is subject to cleavage by one or more enzymes. Additional types of release mechanisms include but are not limited to 1,6-benzyl elimination, β-elimination, and the like. While certain bonds may be considered to be stable or releasable, such characterization should be considered within the overall structure of a molecule or structural entity. In certain instances, a polymer conjugate containing a releasable bond may be referred to as a prodrug, wherein upon cleavage of a releasable bond in vivo (i.e., under physiological conditions), the parent drug is released (or may be eventually released, depending upon the number of polymeric moieties releasably attached to an active agent). A covalent "releasable" linkage, for example, in the context of a water soluble polymer such as polyethylene glycol that is covalently attached to an active moiety such as interleukin-2 or a TLR agonist, such as for example, resiquimod (also known as R848), is one that cleaves under physiological conditions to thereby release or detach a water-soluble polymer from the active moiety, or to detach an active moiety from a water-soluble polymer.

A "stable" linkage or bond refers to a chemical bond that is substantially stable in water (e.g., under physiological conditions), that is to say, does not undergo hydrolysis under physiological conditions to any appreciable extent over an extended period of time. Examples of hydrolytically stable linkages generally include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

A "TLR 7/8 agonist" (or "TLR agonist") is any compound which is an agonist to Toll-like receptor 7 and/or Toll-like receptor 8.

A "PD-1 inhibitor" is any compound (such as a small molecule, ligand, or antibody) which inhibits binding of a programmed cell death protein 1 receptor (PD-1 receptor) with any of its ligands (e.g., PD-L1 and PD-L2). A "PD-L1 inhibitor" is any compound (such as a small molecule, ligand, or antibody) which at least inhibits binding of a PD-1 receptor with the PD-L1 ligand. As used herein, "PD-1/PD-L1 axis inhibitor" refers to PD-1 inhibitors generally as well as PD-L1 inhibitors specifically unless apparent otherwise by context.

"Substantially" or "essentially" means nearly totally or completely, for instance, 95% or greater of a given quantity.

"Pharmaceutically acceptable excipient" or "pharmaceutically acceptable carrier" refers to a component that may be included in the compositions described herein and causes no significant adverse toxicological effects to a subject.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, isopropyl, 3-methylpentyl, and the like. As used herein, "alkyl" includes cycloalkyl when three or more carbon atoms are referenced. An "alkenyl" group is an alkyl group of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo atoms (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclyl, amino, phenoxy, nitro, carboxy, acyl, cyano, or the like. The substituted alkyl groups may be substituted once, twice or three times with the same or with different substituents.

"Lower alkyl" refers to an alkyl group containing from 1 to 7 carbon atoms, and may be straight chain or branched, as exemplified by methyl, ethyl, n-butyl, i-butyl, t-butyl.

"Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

The term "aryl" means an aromatic group having up to 14 carbon atoms. Aryl groups include phenyl, naphthyl, biphenyl, phenanthrenyl, naphthalenyl, and the like. "Substituted phenyl" and "substituted aryl" denote a phenyl group and aryl group, respectively, substituted with one, two, three, four or five (e.g., 1-2, 1-3 or 1-4 substituents) chosen from halo (F, Cl, Br, I), hydroxy, cyano, nitro, alkyl (e.g., $C_{1-6}$ alkyl), alkoxy (e.g., $C_{1-6}$ alkoxy), benzyloxy, carboxy, aryl, and so forth.

A basic reactant or an acidic reactant described herein includes neutral, charged, and any corresponding salt forms thereof.

An exemplary conjugate, active moiety, or other suitably applicable chemical moiety as described herein is meant to encompass, where applicable, analogues, isomers, polymorphs, solvates, and pharmaceutically acceptable salt forms thereof.

"Pharmacologically effective amount," "physiologically effective amount," and "therapeutically effective amount" are used interchangeably herein to mean the amount of an active agent, such as, for example, a polymer conjugate, that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature. For example, a therapeutically effective amount of a compound, or a combination of one or more compounds, when administered (either sequentially or concomitantly) is an amount that elicits a desired biological or medicinal response, e.g., either destroys cancer cells or slows or arrests the progression of a cancer in a subject. The term also applies to a dose of the compounds that will induce a particular desired response in target cells, e.g., when administered in combination, to provide in a beneficial effect. In certain embodiments, the combined effect is additive. In certain embodiments, the combined effect is synergistic. Further, it will be recognized by one skilled in the art that in the case of the instant combination therapy, the amount of each of a PD-1/PD-L1 axis inhibitor, a long-acting IL-2Rβ-biased agonist, such as, e.g., multi(2,7-(bis-methoxyPEG-carboxyamide)(9H-fluorene-9-yl)methyl N-carbamate)interleukin-2, and/or a TLR agonist, may be used in a "sub-therapeutic amount", i.e., less than the therapeutically effective amount of such compound when administered alone.

Combination therapy or "in combination with" refers to the use of more than one therapeutic agent to treat a particular disorder or condition. By "in combination with," it is not intended to imply that the therapeutic agents must be administered at the same time and/or formulated for delivery together, although these methods of delivery are within the scope of this disclosure. A therapeutic agent can be administered concurrently with, prior to, or subsequent to, one or more other additional agents. The therapeutic agents in a combination therapy can also be administered on an alternating dosing schedule, with or without a resting period (e.g., no therapeutic agent is administered on certain days of the schedule). The administration of a therapeutic agent "in combination with" another therapeutic agent includes, but is not limited to, sequential administration and concomitant administration of the two or more agents. In general, each therapeutic agent is administered at a dose and/or on a time schedule determined for that particular agent.

"Pharmaceutically acceptable excipient" or "pharmaceutically acceptable carrier" refers to a component that may be included in the compositions described herein and causes no significant adverse toxicological effects to a patient.

The term "patient," or "subject" as used herein refers to a living organism suffering from or prone to a condition that can be prevented or treated by administration of a compound or composition or combination as provided herein, such as a cancer, and includes both humans and animals. Subjects include, but are not limited to, mammals (e.g., murines, simians, equines, bovines, porcines, canines, felines, and the like), and preferably are human.

"Optional" or "optionally" means that the subsequently described circumstance may, but need not necessarily, occur so that the description includes instances where the circumstance occurs and instances where it does not.

A "small molecule" as used herein refers to an organic compound typically having a molecular weight of less than about 1000 Da.

Overview

The compositions, systems, kits, combinations and methods described herein incorporate a number of innovative advances in drug design and treatment rationale that integrate into novel, potentially safer and highly efficacious anti-cancer therapies that are capable of innate immune system activation.

In an effort to address at least some of the shortcomings associated with current anti-tumor strategies involving single immunotherapeutic agents, such as for example, high systemic exposure and related toxicities and/or sub-optimal oncolytic effects, provided herein are compositions, systems, combinations, and methods comprising administering to a subject having a cancer an innate immunity activating amount (e.g., a T cell stimulatory amount of a PD-1/PD-L1 axis inhibitor, a TLR agonist, and/or an IL-2Rβ-activating amount of a long-acting IL-2Rβ-biased agonist). The present disclosure is based, at least in part, on the discovery of a surprisingly advantageous therapeutic combination comprising (i) a PD-1/PD-L1 axis inhibitor and at least a TLR agonist or a long-acting IL-2R agonist, more specifically, an IL-2Rβ-biased agonist, or (ii) a PD-1/PD-L1 axis inhibitor, a TLR agonist, and a long-acting IL-2R agonist, and more specifically, an IL-2Rβ-biased agonist.

IL-2 stimulates immune cell proliferation and activation through a receptor-signaling complex containing alpha (IL2Rα, CD25), beta (IL2Rβ, CD122), and common gamma chain receptors ($\gamma_c$, CD132). At high doses, IL2 binds to heterodimeric IL2Rβγ receptor leading to desired expansion of tumor killing CD8+ memory effector T (CD8 T) cells. However, IL2 also binds to its heterotrimeric receptor IL2Rαβγ with greater affinity, which expands immunosuppressive CD4+, CD25+ regulatory T cells (Tregs), which can lead to an undesirable effect for cancer immunotherapy. Thus, provided herein is a treatment modality that combines administration of a PD-1/PD-L1 axis inhibitor with (i) an IL-2Rαβ-biased agonist, and in particular, a long-acting IL-2Rαβ-biased agonist, (ii) or a TLR agonist, such as a TLR7/8 agonist, or (iii) both, i.e., with an IL-2Rαβ-biased agonist, and in particular, a long-acting IL-2Rαβ-biased agonist and a TLR agonist, such as a TLR 7/8 agonist. Without being bound by theory, it is believed that by utilizing a PD-1/PD-L1 axis inhibitor capable of stimulating activity of T cells (e.g., enhancing antitumor immune activity of T cells by preventing the suppression of proliferation and immune response of T cells) when selectively combined with a long-acting IL-2 compound in which a region that interacts with the IL2Rα subunit responsible for activating immunosuppressive Tregs is masked (i.e., its activity suppressed or dampened), i.e., a long-acting IL-2Rαβ-biased agonist, and/or selectively combined with a TLR agonist having a mechanism of action of antigen-presenting cell maturation and T-cell priming, a superior therapeutic efficacy can be achieved, as will become apparent from the instant disclosure and supporting examples. Indeed, in a representative example, the foregoing combination produced an unexpectedly advantageous and beneficial increase in survival as compared to administration of a PD-1/PD-L1 axis inhibitor alone or administration of a TLR agonist in combination with a long-acting IL-2Rαβ-biased agonist. In the representative example, when a TLR agonist was directly administered to one tumor (the primary tumor), an abscopal effect was also observed in tumors where the TLR agonist was not directly administered (secondary tumor).

PD-1/PD-L1 Axis Inhibitor

The compositions, systems or combinations provided herein comprise at least one PD-1/PD-L1 axis inhibitor. The treatment methods provided herein comprise administering a PD-1/PD-L1 axis inhibitor, e.g., for immune checkpoint blockade. Administration of the PD-1/PD-L1 axis inhibitor is effective to, for example, enhance T cell cytolytic activity.

Various PD-1/PD-L1 axis inhibitors can be utilized and/or administered in accordance with the compositions, systems, combinations and methods described herein, and the compositions, systems, combinations and methods herein are not limited in this regard. Without being limited as to theory, it is believed that successful outcomes can be achieved via the IL-2 pathway (i.e., via co-administration of a PD-1/PD-L1 axis inhibitor with a TLR agonist and/or a long-acting IL-2Rαβ-biased agonist) to stimulate the desired T-cell responses due to the complementary natures and mechanisms of action of the PD-1/PD-L1 axis inhibitor, TLR agonist, and/or the long-acting IL-2Rαβ-biased agonist.

Illustrative PD-1/PD-L1 axis inhibitors include, but are not limited to, for example: atezolizumab (TECENTRIQ®, MPDL3280A, Roche Holding AG), avelumab (BAVENCIO®, MSB0010718C, Merck KGaA), durvalumab (IMFINZI®, AstraZeneca PLC), nivolumab (OPDIVO®, ONO-4538, BMS-936558, MDX1106, Bristol-Myers Squibb Company), pembrolizumab (KEYTRUDA®, MK-3475, lambrolizumab, Merck & Co., Inc.), BCD100 (BIOCAD Biopharmaceutical Company), BGB-A317 (BeiGene Ltd./Celgene Corporation), CBT-501 (CBT Pharmaceuticals), CBT-502 (CBT Pharmaceuticals), GLS-010 (Harbin Gloria Pharmaceuticals Co., Ltd.), 161308 (Innovent Biologics, Inc.), WBP3155 (CStone Pharmaceuticals Co., Ltd.), AMP-224 (GlaxoSmithKline plc), BI 754091 (Boehringer Ingelheim GmbH), BMS-936559 (Bristol-Myers Squibb Company), CA-170 (Aurigene Discovery Technologies), FAZ053 (Novartis AG), LY3300054 (Eli Lilly & Company), M7824 (Merck KGaA), MEDI0680 (AstraZeneca PLC), PDR001 (Novartis AG), PF-06801591 (Pfizer Inc.), REGN2810 (Regeneron Pharmaceuticals, Inc.), SHR-1210 (Incyte Corporation), TSR-042 (Tesaro, Inc.), AGEN2034 (Agenus Inc.), CX-072 (CytomX Therapeutics, Inc.), JNJ-63723283 (Johnson & Johnson), MGD013 (MacroGenics, Inc.), AN-2005 (Adlai Nortye), ANA011 (AnaptysBio, Inc.), ANB011 (AnaptysBio, Inc.), AUNP-12 (Pierre Fabre Medicament S.A.), BBI-801 (Sumitomo Dainippon Pharma Co., Ltd.), BION-004 (Aduro Biotech), CA-327 (Aurigene Discovery Technologies), CK-301 (Fortress Biotech, Inc.), ENUM 244C8 (Enumeral Biomedical Holdings, Inc.), FPT155 (Five Prime Therapeutics, Inc.), FS118 (F-star Alpha Ltd.), hAb21 (Stainwei Biotech, Inc.), J43 (Transgene S.A.), JTX-4014 (Jounce Therapeutics, Inc.), KD033 (Kadmon Holdings, Inc.), KY-1003 (Kymab Ltd.), MCLA-134 (Merus B.V.), MCLA-145 (Merus B.V.), PRS-332 (Pieris AG), SHR-1316 (Atridia Pty Ltd.), STI-A1010 (Sorrento Therapeutics, Inc.), STI-A1014 (Sorrento Therapeutics, Inc.), STI-A1110 (Les Laboratoires Servier), XmAb20717 (Xencor, Inc.), and pidilizumab (CT-011, Medivation).

BGB-A317 (tislelizumab), under development by BeiGene Ltd., is a humanized IgG4, monoclonal antibody having an engineered Fc region (i.e., where the ability to bind Fc gamma receptor I has been specifically removed). BGB-A317 binds to PD-1 and inhibits the binding of PD-1 to PD-L1 and PD-L2.

In one or more embodiments, the PD-1/PD-L1 axis inhibitor is selected from atezolizumab, avelumab, durvalumab, nivolumab, pembrolizumab, and BGB-A317. It will be appreciated that one or more PD-1/PD-L1 axis inhibitor can be administered in combination as the PD-1/PD-L1 axis inhibitor in the tri- and bi-therapeutic treatment methods provided herein. For example, in one or more embodiments, the PD-1/PD-L1 axis inhibitor is atezolizumab. In yet one or more further embodiments, the PD-1/PD-L1 axis inhibitor is avelumab. In yet other embodiments, the PD-1/PD-L1 axis inhibitor is durvalumab. In some other embodiments, the PD-1/PD-L1 axis inhibitor is nivolumab. In yet one or more additional embodiments, the PD-1/PD-L1 axis inhibitor is pembrolizumab. In some other embodiments, the PD-1/PD-L1 axis inhibitor is BGB-A317.

As shown in Example 19, administration of a combination of a PD-1/PD-L1 axis inhibitor, an exemplary long-acting IL-2Rαβ-biased agonist, multi(2,7-(bis-methoxyPEG-carboxyamide)(9H-fluorene-9-yl)methyl N-carbamate)interleukin-2, and a long acting TLR 7/8 agonist, was effective to increase survival in a murine EMT6 tumor model when compared to immunotherapy with (i) single agent: PD-1/PD-L1 axis inhibitor, TLR agonist, or long-acting IL-2Rαβ-biased agonist (i.e., that is to say, each administered as a single immunotherapeutic agent, (ii) doublet therapy with: an exemplary TLR agonist combined with an exemplary long-acting IL-2Rαβ-biased agonist; with an exemplary PD-1/PD-L1 axis inhibitor combined with an exemplary long-acting IL-2Rαβ-biased agonist; or with an exemplary PD-1/PD-L1 axis inhibitor combined with an exemplary TLR agonist. In the illustrative animal model explored, triplet combination therapy comprising an intermittent 200 µg dose of the PD-1/PD-L1 axis inhibitor resulted in 100% survival.

Toll-Like Receptor 7/8 (TLR7/8) Agonist

The compositions, systems, combinations and treatment methods provided herein may, in one or more embodiments, comprise a TLR agonist, i.e., for stimulating an innate immune response. Administration of the TLR agonist is effective to, for example, activate innate immunity, myeloid cell response and increase tumor antigen presentation. Generally, the TLR agonist can create a tumor suppressing microenvironment in the tumor by mimicking local infection.

Various TLR agonists can be used in the compositions, systems or combinations; or be administered in accordance with the methods described herein, and the disclosure is not limited in this regard. Without being limited as to theory, it is believed that successful outcomes can be achieved via the IL-2 pathway (i.e., via co-administration of a PD-1/PD-L1 axis inhibitor, and a TLR agonist with or without a long-acting IL-2Rαβ-biased agonist) to stimulate the desired T-cell responses due to the complementary natures and mechanisms of action of the PD-1/PD-L1 axis inhibitor, the TLR agonist (and the long-acting IL-2Rαβ-biased agonist).

The ILR agonist is, in some preferred embodiments, long-acting, for example, in the form of a water-soluble polymer conjugate, preferably a multi-arm water soluble polymer conjugate such as a multi-arm polyethylene glycol polymer (PEG) conjugate of a TLR 7/8 agonist. Exemplary multi-arm polymer conjugates of a TLR agonist are described in PCT Application No. PCT/US2018/0131999, the contents of which is expressly incorporated herein by reference in its entirety.

In some embodiments, the TLR agonist is a multi-arm polymer conjugate of a Toll-like receptor ("TLR") agonist compound, i.e., a TLR 7/8 agonist (an agonist of the TLR 7, TLR 8 receptor or both). In some particular embodiments, the multi-arm polymer conjugate has a structure in accordance with Formula I:

Formula I wherein R, taken together with each Q, is a residue of a polyol, polythiol, or polyamine bearing from 3 to about 50 hydroxyl, thiol, or amino groups, respectively; each Q is independently a linker selected from oxygen, sulfur and —NH (e.g., corresponding to an oxygen, sulfur or nitrogen atom from the polyol, polythiol, or polyamine, respectively); each POLY is independently a water-soluble, non-peptidic polymer such as for example a polyethylene glycol; each $X_r$ is independently a linkage-containing spacer moiety; q is a positive integer from 3 to about 50; and each TLR 7/8 AG is a Toll-like receptor 7/8 agonist, wherein Formula I also encompasses pharmaceutically acceptable salts thereof. Discussed below are each of the various components of the multi-arm polymer conjugate of Formula I.

Considering Formula I, in one or more embodiments, the residue of the polyol, polythiol or polyamine, "R," in connection with the multi-arm polymer is an organic radical-containing moiety possessing from about 3 to about 150 carbon atoms (e.g., from about 3 to about 50 carbon atoms). In some preferred embodiments, R when taken together with Q, that is, $(R-Q)_q$, that is the polyol, polyamine or polythiol core molecule, comprises from 3 to about 25 carbon atoms, or from 3 to about 10 carbon atoms, e.g., such as 3, 4, 5, 6, 7, 8, 9, or 10 carbon atoms. The residue may contain one more heteroatoms (e.g., O, S, or N) in addition to those defined by Q. By residue, in reference to a polyol (or polyamine or polythiol), is meant the parent molecule following removal of one or more of its terminal hydrogen atoms, to provide an organic radical suitable for attachment to POLY.

As previously indicated, the residue of the polyol, polythiol or polyamine, "R-Q"$_q$ that forms the basis of the branching for the multi-armed conjugates provided herein, originates from a corresponding polyol, polythiol or polyamine. In one or more embodiments, the corresponding polyol, polythiol, or a polyamine bears at least three hydroxyl, thiol, or amino groups, respectively, available for polymer attachment. A "polyol" is a molecule comprising three or more hydroxyl groups. A "polythiol" is a molecule that comprises three or more thiol groups. A "polyamine" is a molecule comprising three or more amino groups.

In one or more embodiments, the polyol, polyamine or polythiol typically contains 3 to about 25 hydroxyl groups, or amino groups, or thiol groups, respectively, such as from 3 to about 10 (i.e., 3, 4, 5, 6, 7, 8, 9, or 10) hydroxyl, amino groups or thiol groups, respectively, preferably from 3 to about 8 (i.e., 3, 4, 5, 6, 7, or 8) hydroxyl, amino groups or thiol groups, respectively. In one or more embodiments, the number of atoms between each hydroxyl, thiol, or amino group will vary, although lengths of from about 1 to about 20 (e.g., from 1 to about 5) intervening atoms, such as carbon atoms, between each hydroxyl, thiol or amino group, are exemplary. In referring to intervening core atoms and lengths, —CH$_2$— is considered as having a length of one intervening atom, —CH$_2$CH$_2$— is considered as having a length of two atoms, and so forth.

Exemplary polyols and polyamines have (Radical)-(OH)$_q$ and (Radical)-(NH$_2$)$_q$ structures, respectively, where (Radical) corresponds to an organic-containing radical and q is a positive integer from 3 to about 50. Note that, as described above, in Formula I, the variable "Q," when taken together with R, typically represents a residue of the core organic radical as described herein. That is to say, when describing polyols, polythiols and polymer amines, particularly by name, these molecules are referenced in their form prior to incorporation into a multi-armed polymer-containing structure (i.e., are referred to as their parent molecules). That is to say, when describing preferred organic core molecules, particularly by name, the core molecules are described in their precursor form, rather than in their radical form after removal of, for example, one or more protons. So, if for example, the organic core radical is derived from pentaerythritol, the precursor polyol possesses the structure C(CH$_2$OH)$_4$, and the organic core radical, together with Q, corresponds to C(CH$_2$O—)$_4$, where Q is O. So, for example, for a conjugate of Formula I wherein R taken together with Q is a residue of the polyol, pentaerythritol C(CH$_2$OH)$_4$, a residue R together with Q corresponds to "C(CH$_2$O—)$_4$", such that each of "q" polymer arms in the multi-armed polymer conjugate will emanate from each of the oxygen atoms of the pentaerythritol core or residue.

Illustrative polyols include aliphatic polyols having from 1 to 10 carbon atoms and from 3 to 10 hydroxyl groups, including for example, trihydroxyalkanes, tetrahydroxyalkanes, polyhydroxy alkyl ethers, polyhydroxyalkyl polyethers, and the like. Cycloaliphatic polyols include straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional examples of aliphatic polyols include derivatives of glucose, ribose, mannose, galactose, and related stereoisomers. Aromatic polyols may also be used, such as 1,1,1-tris(4'-hydroxyphenyl) alkanes, such as 1,1,1-tris(4-hydroxyphenyl)ethane, 2,6-bis(hydroxyalkyl)cresols, and the like. Other core polyols that may be used include polyhydroxycrown ethers, cyclodextrins, dextrins and other carbohydrates (e.g., monosaccharides, oligosaccharides, and polysaccharides, starches and amylase).

Exemplary polyols include glycerol, trimethylolpropane, pentaerythritol, dipentaerythritol, tripentaerythritol, ethoxylated forms of glycerol, trimethylolpropane, pentaerythritol, dipentaerythritol, tripentaerythritol. Also, preferred are reducing sugars such as sorbitol and glycerol oligomers, such as diglycerol, triglycerol, hexaglycerol and the like. A 21-arm polymer can be synthesized using hydroxypropyl-β-cyclodextrin, which has 21 available hydroxyl groups. Additionally, a polyglycerol having an average of 24 hydroxyl groups is also included as an exemplary polyol.

Exemplary polyamines include aliphatic polyamines such as diethylene triamine, N,N',N''-trimethyldiethylene triamine, pentamethyl diethylene triamine, triethylene tetramine, tetraethylene pentamine, pentaethylene hexamine, dipropylene triamine, tripropylene tetramine, bis-(3-aminopropyl)-amine, bis-(3-aminopropyl)-methylamine, and N,N-dimethyl-dipropylene-triamine. Naturally occurring polyamines that can be used include putrescine, spermidine, and spermine. Numerous suitable pentamines, tetramines, oligoamines, and pentamidine analogs suitable for use are described in Bacchi et al. (2002) *Antimicrobial Agents and Chemotherapy*, 46(1):55-61, which is incorporated by reference herein.

Provided below are illustrative structures corresponding to residues of polyols (although each structure is depicted with the oxygen atom ("O") derived from the corresponding hydroxyl group, each "O" can be substituted with sulfur ("S") or NH to depict the corresponding residue of a polythiol or polyamine, respectively). Note that the residues shown below would be understood in terms of conjugates of Formula I as corresponding to R taken together with Q to provide a multi-armed polymer conjugate having a number of arms corresponding to the number of oxygen (or other suitable heteroatom) atoms shown below.

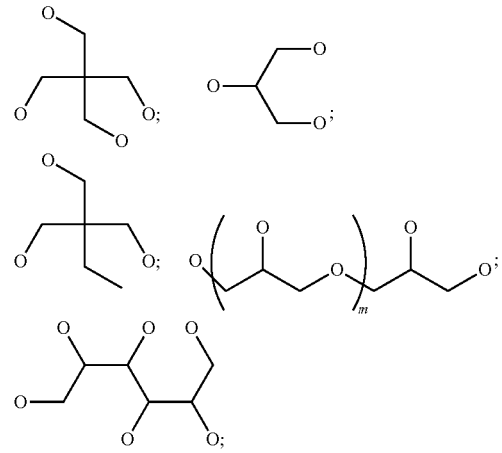

-continued

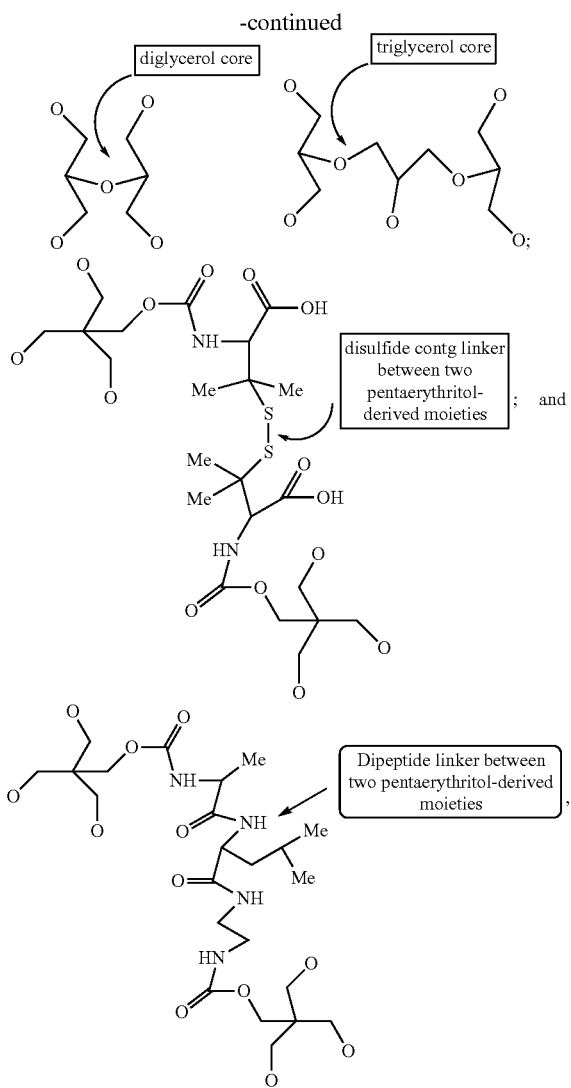

wherein m is a positive integer from 0-40 [e.g., 0-10, for example, 0-5 (i.e., 0, 1, 2, 3, 4, 5, etc.)].

The multi-arm polymer TLR 7/8 agonist conjugates comprise a water-soluble, non-peptidic polymer. A wide array of polymers may be used and the structures provided herein are not limited with respect to the type (e.g., polyethylene oxide or polyoxazoline), or size (e.g., from 2 to 4,000 monomers in size) of water-soluble polymer.

With respect to type, the water-soluble, non-peptidic polymer is understood as a series of repeating monomers, wherein the type of monomer(s) dictates the type of water-soluble, non-peptidic polymer. Exemplary monomers include, but are not limited to alkylene oxides, such as ethylene oxide or propylene oxide; olefinic alcohols, such as vinyl alcohol, 1-propenol or 2-propenol; vinyl pyrrolidone; hydroxyalkyl methacrylamide and hydroxyalkyl methacrylate, where, in each case, alkyl is preferably methyl; α-hydroxy acids, such as lactic acid or glycolic acid; phosphazene, oxazoline, carbohydrates such as monosaccharides, alditol such as mannitol; and N-acryloylmorpholine. In one or more embodiments, the water-soluble, non-peptidic polymer is a co-polymer of two monomer types selected from this group, or, more preferably, is a homo-polymer of one monomer type selected from this group. With respect to co-polymers, which includes block copolymers, the two monomer types in a co-polymer may be of the same monomer type, for example, two alkylene oxides, such as ethylene oxide and propylene oxide.

With respect to size, the water-soluble, non-peptidic polymer may be a relatively small or the water-soluble, non-peptidic polymer may be relatively large.

In reference to POLY in Formula I, that is to say, each polymer arm, in those embodiments in which a relatively small water-soluble, non-peptidic polymer is present, exemplary values of molecular weights include: below about 2000; below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 daltons. Exemplary ranges for a relatively small water-soluble, non-peptidic polymer include from about 100 to about 1400 daltons; from about 100 to about 1200 daltons; from about 100 to about 800 daltons; from about 100 to about 500 daltons; from about 100 to about 400 daltons; from about 200 to about 500 daltons; from about 200 to about 400 daltons; from about 75 to 1000 daltons; and from about 75 to about 750 daltons.

For relatively small water-soluble, non-peptidic polymers ("POLY"), the number of monomers in will typically fall within one or more of the following ranges: between 1 and about 30 (inclusive); between about 2 and about 25; between about 2 and about 20; between about 2 and about 15; between about 2 and about 12; between about 2 and about 10. In certain instances, the number of monomers in series in the polymer (and the corresponding conjugate) is one of 1, 2, 3, 4, 5, 6, 7, or 8. In additional embodiments, the polymer (and the corresponding conjugate) contains 9, 10, 11, 12, 13, 14, 15, 16, 17, 18, 19, or 20 monomers. In yet further embodiments, the polymer portion in each polymer "arm" (and the corresponding conjugate) possesses 21, 22, 23, 24, 25, 26, 27, 28, 29 or 30 monomers in series. Thus, for example, when the water-soluble, non-peptidic polymer arm comprises —($OCH_2CH_2$)$_n$—, "n" is an integer that, in some embodiments, is selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30, and can fall within one or more of the following ranges: between about 1 and about 25; between about 1 and about 20; between about 1 and about 15; between about 1 and about 12; between about 1 and about 10.

When the molecular weight of the overall water-soluble, non-peptidic polymer in the conjugate is relatively large (e.g., greater than 2,000 daltons), the overall molecular weight can fall within the range of 2,000 daltons to about 150,000 daltons. Exemplary ranges, however, include molecular weights in the range of from about 3,000 daltons to about 120,000 daltons; in the range of from about 5,000 daltons to about 110,000 daltons; in the range of from greater than 5,000 daltons to about 100,000 daltons, in the range of from about 6,000 daltons to about 90,000 daltons, in the range of from about 10,000 daltons to about 85,000 daltons, in the range of greater than 10,000 daltons to about 85,000 daltons, in the range of from about 20,000 daltons to about 85,000 daltons, in the range of from about 53,000 daltons to about 85,000 daltons, in the range of from about 25,000 daltons to about 120,000 daltons, in the range of from about 29,000 daltons to about 120,000 daltons, in the range of from about 35,000 daltons to about 120,000 daltons, and in the range of from about 40,000 daltons to about 120,000 daltons.

Exemplary molecular weights for relatively large water-soluble, non-peptidic polymers, in reference to each of the polymer arms "POLY", in Formula I, include about 500 daltons, about 750 daltons, about 1,000 daltons, about 1500 daltons, about 2,000 daltons, about 2,200 daltons, about 2,500 daltons, about 3,000 daltons, about 4,000 daltons, about 4,400 daltons, about 4,500 daltons, about 5,000 daltons, about 5,500 daltons, about 6,000 daltons, about 7,000 daltons, about 7,500 daltons, about 8,000 daltons, about 9,000 daltons, about 10,000 daltons, about 11,000 daltons, about 12,000 daltons, about 13,000 daltons, about 14,000 daltons, about 15,000 daltons, and about 20,000 daltons.

Exemplary molecular weights for relatively large water-soluble, non-peptidic polymers, in reference to the overall polymer portion of the multi-arm conjugate include, for example, about 20,000 daltons, 22,500 daltons, about 25,000 daltons, about 30,000 daltons, about 35,000 daltons, about 40,000 daltons, about 45,000 daltons, about 50,000 daltons, about 55,000 daltons, about 60,000 daltons, about 65,000 daltons, about 70,000 daltons, and about 75,000 daltons. Branched versions of the water-soluble, non-peptidic polymer having a total molecular weight of any of the foregoing can also be used in each of the polymer arms to provide a multiply-branched conjugate.

Thus, regardless of whether a relatively small or large water-soluble, non-peptidic polymer is used, when the water-soluble, non-peptidic polymer is a poly(ethylene oxide), the polymer will comprise a number of $(OCH_2CH_2)$ monomers [or $(CH_2CH_2O)$ monomers, depending on how the PEG is defined]. As used throughout the description, the number of repeat units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

With respect to multi-arm water-soluble, non-peptidic polymers, these polymers typically contain three or more discernable water-soluble, non-peptidic polymer arms or segments. Among other benefits, multi-arm water-soluble, non-peptidic polymers—given the ability of each arm to covalently attach to a TLR 7/8 agonist—have the potential to provide greater drug character compared to, for example, a linear polymer having a single TLR 7/8 agonist attached thereto. In one or more preferred embodiments, the multi-arm water soluble polymer has 4 polymer arms, e.g., PEG arms, each attached to a TLR 7/8 agonist, via Xr.

In reference to Formula I, the linkage-containing spacer moiety that generally covalently attaches POLY to the TLR 7/8 agonist may be hydrolytically and/or enzymatically stable or releasable at biologically relevant pHs. That is to say, in some embodiments, Xr is a hydrolytically stable linkage. In yet some other embodiments, Xr comprises a releasable linkage.

As described previously, a stable linkage is one that does not appreciably cleave in vivo following administration to a patient. In this regard, stable linkages are known to those of ordinary skill in the art. In addition, whether a given linkage serves as a stable linkage in connection with the conjugates provided herein may be tested through experimentation (e.g., by administering a conjugate having the proposed stable linkage to a patient and testing, e.g., via chromatographic or other suitable techniques, periodically obtained blood samples for indications of cleavage).

In some embodiments of a multi-arm conjugate, the linkage containing spacer moiety comprises a releasable linkage interposed between the TLR 7/8 agonist and the water-soluble, non-peptidic polymer. Thus, a releasable linkage is one that cleaves in vivo following administration to a patient, to thereby release the TLR 7/8 agonist compound (or a slightly modified version thereof, e.g., with a small molecular tag) from its polymer arm. In this regard, releasable linkages are known to those of ordinary skill in the art. In addition, whether a given linkage is releasable in nature in connection with the multi-armed conjugates provided herein can be tested through experimentation (e.g., by administering a conjugate having the proposed releasable linkage to a patient and testing, e.g., via chromatographic or other suitable techniques, periodically obtained blood samples for indications of cleavage). In some preferred embodiments, a multi-arm polymer conjugate of a TLR 7/8 agonist comprises a releasable linkage, that is to say, Xr comprises a releasable linkage.

For example, assessment of the releasable nature of a linkage comprised in a multi-armed polymer conjugate of a TLR 7/8 agonist can be determined in vitro after incubation of a conjugate sample with heparinized and pooled plasma (pH 7.2-7.4) from humans at 37° C. and samples withdrawn at various time points, where samples are immediately frozen until sample analysis and quantification, e.g., using any suitable technique for detection and quantification such as LC-MS. An apparent conversion half-life ($t_{1/2,app}$) is then calculated based on the assumption that the conjugate conversion from its initial nominal incubation concentration is attributed only to TLR 7/8 agonist release, where a $t_{1/2}$ of about 300 hours or less can be considered to be indicative of a releasable linkage or a releasable conjugate.

Exemplary releasable linkages for use in connection with the conjugates provided herein may include, without limitation, amide, thioether, carbamate, ester, carbonate, urea and enzyme-cleavable peptidic linkages, depending upon the structure of the TLR 7/8 agonist compound and the overall linker structure. In some instances, a bond or linkage may not generally be considered to be "releasable" or cleavable in nature, when considered alone, however, when taken together with the structure of the molecular entity to which it is covalently attached, e.g., a TLR 7/8 agonist compound having an imidazoquinoline structure, such linkage may releasable, due to particular release mechanism such as a beta-elimination, amide hydrolysis, or the like. For example, thioether, amide, carbamate, ester, carbonate, urea, and the like can cleave via a β-elimination reaction or via hydrolysis (with or without the enzymatic coordination, e.g., an ester can serve as a releasable linkage regardless of whether the ester is cleaved via an esterase).

Multi-arm polymer conjugates of a TLR 7/8 agonist comprising a releasable linkage are, in instances when release results in release of the unmodified parent molecule, often categorized as prodrugs, since they release the covalently attached TLR 7/8 agonist compound following administration (i.e., under physiological conditions). In general, multi-arm polymer resiquimod (R-848) conjugates described herein comprise releasable linkages to resiquimod.

With respect to enzyme-cleavable peptidic linkages, the spacer moiety can include one or more of a series of amino acids known to be a substrate for an enzyme present in the intended patient population. In this way, upon administration to the patient, enzymatic-induced cleavage of the enzyme-cleavable peptidic linkage comprised in the conjugate will release a TLR 7/8 agonist (or a TLR 7/8 agonist with a relatively small molecular fragment or "tag" resulting from the cleavage). Examples of peptidic linkages subject to enzymatic cleavage in a given patient population are described, for example, in U.S. Patent Application Publication No. US 2005/0079155, and can also be determined experimentally.

In reference to Xr, the linkage-containing spacer moiety may comprise any of a number of exemplary amino acids, such a beta-alanine, glycine, L-alanine, L-valine, leucine, dimethylglycine and the like. In some embodiments, Xr comprises a carboxymethyl ("CM") group, —CH$_2$C(O)— covalently attached to any one or more of the foregoing amino acids via its amino group, wherein its terminal carboxy group is covalently attached to an amino group of the TLR 7/8 agonist to provide an amide linkage, which in some embodiments, is releasable.

In some embodiments, the linkage-containing spacer moiety, "Xr," is in accordance with Formula II:

(Formula II)

wherein "a" is zero or one (such that zero represents absence of "X$^1$" and one indicates its presence); "b" is zero or one (such that zero represents absence of "Lr" and one indicates its presence); X$^1$, when present, is a spacer; Lr, when present, is a linkage; and X$^2$ is a functional group directly covalently attached to the TLR 7/8 agonist.

In those instances of Formula II wherein a and b are both zero, it will be understood that the linkage-containing spacer is made up of X$^2$, the functional group that covalently attaches the TLR 7/8 agonist to the remainder of the multi-arm polymer (e.g., to a polymer arm, POLY). In such an instance, the linkage-containing spacer only contains the functional group X$^2$ and no other atoms are present between the TLR 7/8 agonist and the water-soluble, non-peptidic polymer. Typically, X$^2$ comprises an atom or atoms of the unmodified TLR 7/8 agonist to which the remainder of the multi-arm polymer is covalently attached. For example, if attachment occurs at an amino group of the TLR 7/8 agonist, typically the amino group forms part of X$^2$.

In those instances of Formula II wherein either or both of a and b are one, it will be understood that the linkage-containing spacer contains one or more additional atoms other than those that make up X$^2$. Non-limiting exemplary X$^1$ and Lr, when considered either left to right or right to left, include —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—, —CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—, —CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—, —CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—, —CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$-, a bivalent cycloalkyl group, —N(R$^6$)—, where R$^6$ is H or an organic radical selected from the group consisting of alkyl, substituted alkyl, alkenyl, substituted alkenyl, alkynyl, substituted alkynyl, aryl and substituted aryl, and combinations of one or more of the foregoing. Additional spacers and linkages include acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, 4-(methoxy-lower alkyl)-1-piperizinyl, fluorenyl, and guanidine. For purposes of the present description, however, a group of atoms is not considered a spacer when it is immediately adjacent to a polymeric segment, and the group of atoms is the same as a monomer of the polymer such that the group would represent a mere extension of the polymer chain.

When present, a spacer and or linkage is typically but is not necessarily linear in nature. In addition, a spacer and/or linkage is typically but is not necessarily hydrolytically stable and/or is enzymatically stable. In one or more embodiments, a spacer or linkage, when present, has a chain length of less than about 12 atoms (e.g., less than about 10 atoms, less than about 8 atoms, and less than about 5 atoms). With respect to determining length of a particular spacer or linkage, length herein is defined as the number of atoms in a single chain, not counting substituents. For instance, a urea linkage such as this, R-POLY-NH—(C═O)—NH-TLR 7/8 Agonist, is considered to have a chain length of three atoms (—N̲H—C̲(O)—N̲H—).

In reference to Formula II, a particular example of X$^1$, when present, includes —CH$_2$C(O)— (referred to herein as carboxymethyl).

Examples of X$^2$ include, —C(O)—NH— (where NH is a point of attachment to the TLR 7/8 agonist, and forms part of the unmodified TLR agonist prior to covalent attachment); —NH—C(O)—N̲H— (where N̲H is a point of attachment to the TLR 7/8 agonist and forms part of the unmodified TLR agonist prior to covalent attachment); —NH—C̲(O) (where the carbonyl carbon represents a point of attachment to the TLR 7/8 agonist and forms part of the unmodified TLR agonist prior to covalent attachment), and —N̲H (where the nitrogen atom represents a point of attachment to the TLR 7/8 agonist and forms part of the unmodified TLR agonist prior to covalent attachment).

Examples of Lr include —($CR_xR_y$)$_z$—, and —NH($CR_xR_y$)$_z$— where each $R_x$ and $R_y$ is independently selected from hydrogen, lower alkyl, halo (X), and halo-substituted lower alkyl, and z is an integer from 1 to 6, e.g., is selected from 1, 2, 3, 4, 5, and 6. Examples of lower alkyl include methyl, ethyl, propyl, isopropyl, butyl, isobutyl, sec-butyl, pentyl, and hexyl; exemplary halo groups are fluoro, chloro, bromo, iodo. Illustrative Lr groups include, e.g., —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CHF$—, —$CHCH_3$—, —$CHCH(CH_3)_2$—, —$CHCH_2CH(CH_3)_2$—, —$C(CH_3)_2$—, —$NHCH_2$—, —$NHCH_2CH_2$—, —$NHCH_2CH_2CH_2$—, —$NHCH_2CH_2CH_2CH_2$—, —$NHCH_2CH_2CH_2CH_2CH_2$—, —$NHCH_2CH_2CH_2CH_2CH_2CH_2$—, —$NHCH_2CHF$—, —$NHCHCH_3$—, —$NHCHCH(CH_3)_2$—, —$NHCHCH_2CH(CH_3)_2$—, and —$NHC(CH_3)_2$—. Additional structures are provided herein.

In one or more embodiments, a TLR 7/8 agonist, e.g., a long acting TLR 7/8 agonist that is a multi-arm water soluble polymer-TLR agonist conjugate, may possess from about 3 to about 50 polymer arms, and more typically will possess from about 3 to about 10 polymer arms extending from a central core molecule (e.g., typically a polyol, polythiol or polyamine) to which the water-soluble polymer portion is either stably or releasably covalently attached (e.g., will possess 3, 4, 5, 6, 7, 8, 9 or 10 water-soluble polymer arms). Typically, the water-soluble polymer arms extending from a central core are stably covalently attached thereto. Exemplary polyol core molecules include, for example, glycerol, trimethylolpropane, reducing sugars such as sorbitol or pentaerythritol, and glycerol oligomers, such as hexaglycerol. Typically, but not necessarily, the multi-armed water-soluble polymer conjugate will possess a TLR agonist covalently attached at the terminus of each polymer arm.

Turning now to the TLR 7/8 agonist of Formula I, a TLR 7/8 agonist is any compound that is an agonist to Toll-like receptor 7 and/or Toll-like receptor 8. Preferably, the TLR 7/8 agonist is a small molecule agonist. Illustrative structural classes include guanosine-containing compounds and imidazoquinolines. Illustrative TLR agonists include, but are not limited to, for example, TLR-7 or TLR-8 agonists.

Representative TLR agonists include, for example, telratolimod (3M-052, 3M; MEDI-9797, MedImmune), resiquimod (R848; S-28463, available from 3M), imiquimod (R837; S-26308), S-28690 (an imidazoquinoline, 3M), N-[4-(4-amino-2-ethyl-1H-imidazo[4,5-c]quinolin-1-yl)butyl-]methanesulfonamide (3M-001, 3M), (852A, 3M; PF-4878691, Pfizer) vesimune (TMX-101, Telormedix SA), esatolimod (GS-9620, Gilead Sciences), ANA-773 (Anadys), methyl 2-(3-(((3-(6-amino-2-butoxy-8-oxo-7,8-dihydro-9H-purin-9-yl)propyl)(3-morpholinopropyl)amino) methyl)phenyl)acetate (AZD8848, Astra Zeneca), CL097, a water-soluble derivative of R848 (InvivoGen), a thiazoloquinolone derivative (CL057; 3M-002, 3M), 3M-003 (an imidazoquinoline, 3M), TMX-202 (Telormedix SA), TMX-302 (Telormedix SA), TMX-306 (Telormedix SA), 9-benzyl-8-hydroxy-2-(2-merthoxyethoxy) adenine (IV136, Pfizer), 4-{[6-amino-2-(2-methoxyethoxy)-8-oxo-7H-purin-9(8H)-yl]methyl}benzoic acid (1V209), an imidazoquinoline (3M-011, 3M), 2-butylamino-8-hydroxy-9-(6-methylpyridine-3-ylmethyl) adenine (SM-276001), methyl 3-[(6-amino-2-butoxy-7,8-dihydro-8-oxo-9H-purin-9-yl)methyl] benzeneacetate (SM-324405), 9-benzyl-8-hydroxy-2-(2-methoxyethoxy) adenine (SM-360320), 4-Amino-1-benzyl-6-trifluoromethyl-1,3-dihydroimidazo [4,5-c] pyridin-2-one (PF-4171455, Pfizer), CpG, CpR, ssRNA, BHMA, methyl 2-(3-(((3-(6-amino-2-butoxy-8-oxo-7,8-dihydro-9H-purin-9-yl)propyl)(3-(dimethylamino)propyl)amino)methyl)phenyl)acetate (AZ12441970, AstraZeneca), and 2-(3-(((3-(6-amino-2-butoxy-8-oxo-7H-purin-9(8H)-yl)propyl)(3-(dimethylamino)propyl)amino)phenyl)acetic acid (AZ12443988, AstraZeneca).

For example, in one or more embodiments, the TLR 7/8 agonist is selected from the following: 4-((6-amino-8-hydroxy-2-(2-methoxyethoxy)-9H-purin-9-yl)-methyl)-N-(20-azido-3,6,9,12,15,18-hexaoxaicosyl)benzamide; 3-(1-(1-(4-((6-amino-8-hydroxy-2-(2-methoxyethoxy)-9H-purin-9-yl)methyl)phenyl)-1-oxo-5,8,11,14,17,20-hexaoxa-2-azadocosan-22-yl)-1H-1,2,3-triazol-4-yl)propanoic acid; 4-((6-amino-8-hydroxy-2-(2-methoxyethoxy)-9H-purin-9-yl)-methyl)-N-(20-amino-3,6,9,12,15,18-hexaoxaicosyl)benzamide; 4-((6-amino-8-hydroxy-2-(2-methoxyethoxy)-9H-purin-9-yl)methyl)-N-(32-azido-3,6,9,12,15,18,21,24,27,30-decaoxa-yl)methyl)-N-(32-azido-3,6,9,12,15,18,21,24,27,30-decaoxadotriacontyl)benzamide; 3-(1-(1-(4-((6-amino-8-hydroxy-2-(2-methoxyethoxy)-9H-3-(1-(1-(4-((6-Amino-8-hydroxy-2-(2-methoxyethoxy)-9Hpurin-9-yl) methyl)phenyl)-1-oxo-5,8,11,14,17,20,23,26,29,32-decaoxa-2-azatetratriacontan-34-yl)-1H-1,2,3-triazol-4-yl)-propanoic acid; 4-((6-amino-8-hydroxy-2-(2-methoxyethoxy)-9H-purin-9-yl)methyl)-N-(32-amino-3,6,9,12,15,18,21,24,27,30-decaoxadotriacontyl)-benzamide; 4-((6-amino-8-hydroxy-2-(2-methoxyethoxy)-9H-purin-9-yl) methyl)-N-(59-amino-3,6,9,12,15,18,21,24,27,30,33,36,39,42,45,48,51,54,57-nonadecaoxanonapentacontyl)benzamide; N-[4-(4-amino-2-ethyl-1H-imidazo[4,5c]quinolin-1-yl)butyl] methanesulfonamide; [8-(3-(pyrrolidin-1-ylmethyl)benzyl)-4-amino-2-butoxy-7,8-dihydropteridin-6(5H)-one]; [2-(4-((6-amino-2-(2-methoxyethoxy)-8-oxo-7H-purin-9(8H)-yl) methyl) benzamido) ethyl 2,3-Bis (dodecanoyloxy) propyl phosphate]; [1-(4-((6-amino-2-(2-methoxyethoxy)-8-oxo-7H-purin-9(8H)-yl) methyl) phenyl)-1-oxo-5,8,11,14,17,20-hexaoxa-2-azatricosan-23-oic acid]; [9-benzyl-8-hydroxy-2-(2-methoxyethoxy) adenine; methyl 2-(3-(4-{[6-amino-2-butoxy-8-oxo-7H-purin-9(8H)-yl]methyl}phenyl)acetate, SM-324406: 2-(3-{[6-amino-2-butoxy-8-oxo-7H-purin-9(8H)-yl]methyl}phenyl)acetic acid; methyl 2-(3-(((3-(6-amino-2-butoxy-8-oxo-7H-purin-9(8H)-yl)propyl)(3-(dimethylamino)propyl)amino)phenyl) acetate; 2-(3-(((3-(6-amino-2-butoxy-8-oxo-7H-purin-9 (8H)-yl)propyl)(3-(dimethylamino)propyl)amino)phenyl).

In some particular embodiments of Formula I, the TLR 7/8 agonist is telratolimod (3M-052, 3M; MEDI 9197, MedImmune), resiquimod (R848; S-28463, available from 3M), N-[4-(4-amino-2-ethyl-1H-imidazo[4,5-c]quinolin-1-yl)butyl-]methanesulfonamide (3M-001, 3M-852A, 3M; PF-4878691, Pfizer), imiquimod (R837; S-26308), S-28690 (an imidazoquinoline, 3M), vesimune (TMX-101, Telormedix SA), vesatolimod (GS-9620, Gilead Sciences), ANA-773 (Anadys), methyl 2-(3-(((3-(6-amino-2-butoxy-8-oxo-7,8-dihydro-9H-purin-9-yl)propyl)(3-morpholinopropyl) amino)methyl)phenyl)acetate (AZD8848, AstraZeneca), 2-(ethoxymethyl)-1H-imidazo[4,5-c]quinolin-4-amine (CL097, a water-soluble derivative of R848, InvivoGen), methyl 3-[(6-amino-2-butoxy-7,8-dihydro-8-oxo-9H-purin-9-yl)methyl]benzeneacetate (SM-324405), methyl 2-(3-(((3-(6-amino-2-butoxy-8-oxo-7,8-dihydro-9H-purin-9-yl) propyl)(3-(dimethylamino)propyl)amino)methyl)phenyl) acetate (AZ12441970, AstraZeneca), GSK2245053 (GlaxoSmithKline), an adenine analog (SZU-101, Santa Cruz Biotechnology), 4-[6-amino-8-hydroxy-2-(2-methoxyethoxy)purin-9-ylmethyl]benzaldehyde (UC-1V150, U.C. San Diego), 9-benzyl-8-hydroxy-2-(2-merthoxyethoxy)adenine (SM360320, 1V136, Pfizer), VTX-1463 and VTX-2337 (VentiRx). In yet some other embodiments, the TLR 7/8 agonist is (N-[4-(4-amino-2-ethyl-1H-imidazo[4,5c]quinolin-1-yl)butyl] methanesulfonamide or [8-(3-(pyrrolidin-1-ylmethyl)benzyl)-4-amino-2-butoxy-7,8-dihydropteridin-6(5H)-one].

In certain preferred embodiments, the TLR 7/8 agonist is an imidazoquinoline compound. Illustrative imidazoquinolines include, for example, 1-substituted, 2-substituted 1H-imidazo[4,5-c]-quinolin-4-amine compounds such as described in U.S. Pat. No. 5,389,640. Such compounds include 4-amino-7-chloro-alpha, alpha-dimethyl-2-ethoxymethyl-1H-imidazo[4,5-c]q uinoline-1-ethanol; 4-amino-alpha,alpha-dimethyl-2-hydroxymethyl-1H-imidazo[4,5-c]quinoline-1-ethanol; 4-amino-alpha,alpha-dimethyl-2-methoxymethyl-1H-imidazo[4,5-c]quinoline-1-ethanol; 2-ethoxymethyl-1-(3-methoxypropyl)-1H-imidazo[4,5-c]quinolin-4-amine; and 1-(2-methoxyethyl)-2-methoxymethyl-1H-imidazo[4,5-c]quinolin-4-amine.

In one or more preferred embodiments, the TLR 7/8 agonist is resiquimod (R-848) or imiquimod (1-isobutyl-1H-imidazo[4,5-c]quinolin-4-amine), or is a derivative thereof. In one or more particular embodiments, the TLR 7/8 agonist is imiquimod,

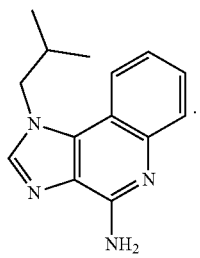 [SMILES: CC(C)Cn1cnc2c(N)nc3ccccc3c21]

In yet certain other particular embodiments, the TLR 7/8 agonist is resiquimod,

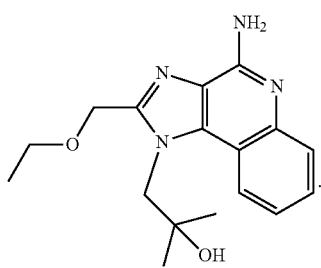

R-848

Covalent attachment of the TLR 7/8 agonist to the multi-armed polymer may take place via attachment to any suitable functional group or atom on the TLR 7/8 agonist compound. Illustrative functional groups suitable for attachment to the multi-armed polymer include amino, hydroxyl, carboxy, and thiol, and the like. In certain preferred embodiments, covalent attachment to imiquimod takes place at the aromatic —$NH_2$ group. In other preferred embodiments, covalent attachment to resiquimod takes place at the aromatic —$NH_2$ group. Exemplary structures are provided below.

The conjugates described herein may be prepared in a variety of methods, and exemplary syntheses are provided in the examples which follow.

In an example, the multi-arm polymer TLR7/8 agonist conjugates are prepared by a method comprising covalently attaching a multi-arm water-soluble, non-peptidic reactive polymer to a TLR 7/8 agonist. Many TLR 7/8 agonists may be obtained commercially or may be synthesized by methods known to those of skill in the art.

Certain features of a multi-arm polymer conjugate of a TLR 7/8 agonist are preferred and each of these features as described below is to be considered individually and explicitly in combination. In some preferred embodiments, each of the polymer arms emanating from the central core is the same. That is to say, for example, in reference to Formula I, emanating from R, each Q, POLY, Xr and TLR 7/8 agonist is the same. In certain preferred embodiments, q is 4. In other preferred embodiments, the multi-arm polymer conjugate comprises a pentaerythritol core. In yet some further embodiments, the TLR 7/8 agonist is resiquimod. In yet some additional embodiments, POLY is a polyethylene glycol and POLY-Xr comprises —$CH_2$—C(O)-amino acid-, where the amino acid is selected from beta-alanine, glycine, L-alanine, L-valine, leucine, $H_2NCH_2CHFCOOH$, and dimethylglyine, and the amino group of the amino acid is directly attached to the carbonyl group. In yet some further embodiments of the foregoing, the amino acid is glycine. In yet some further embodiments, the multi-arm polymer conjugate is Compound 6.

Among other advantages, the multi-arm polymer TLR 7/8 conjugates provided herein allow local administration of the conjugate, e.g., to a tumor site, wherein the conjugate is effective to preferentially initiate anti-tumor immunity locally during residence at the tumor site. The architecture of the multi-armed conjugate, along with the particular TLR 7/8 agonist, attachment chemistry, and mode of administration are effective to result in a conjugate that remains for an extended period of time within a tumor, and is effective to increase tumor antigen presentation and T-cell stimulation (i.e., to result in enhanced CD8 T cell priming), that is, to elicit an innate immune response, while accompanied by minimal toxic side effects due to localized activity.

Representative conjugates having features as described above are provided below. For example, a conjugate may have a structure as defined by Formula III:

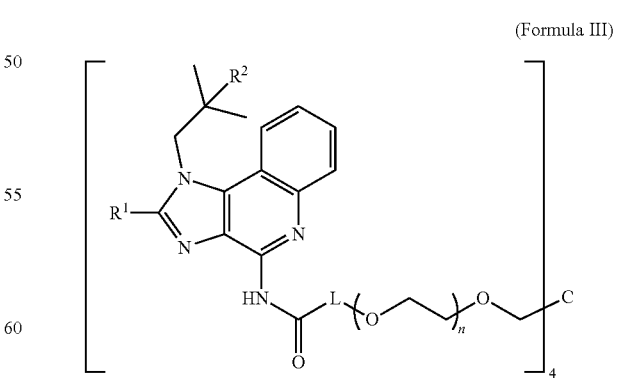

(Formula III)

or a pharmaceutically acceptable salt or stereoisomer thereof, wherein:

L is —$(CH_2)_m$—, —$(CH_2)_m$—NH—C(O)—$(CH_2)_m$—, —$CHF(CH_2)_m$—NH—C(O)—$(CH_2)_m$—, —$CH(CH_3)_m$—

—NH—C(O)—(CH$_2$)$_m$—, —(CH$_2$)$_m$—CH(CH(CH$_3$)$_2$)$_m$—
—NH—C(O)—(CH$_2$)$_m$—, —(CH$_2$)$_m$—CH(CH$_2$CH(CH$_3$)$_2$)$_m$
—NH—C(O)—(CH$_2$)$_m$—, —C(CH$_3$)$_2$—NH—C(O)—
(CH$_2$)$_m$—, a single bond, or —NH—(CH$_2$)$_m$—, each m is independently an integer from 1 to 5, inclusive;
each n is independently an integer from 40 to 350, inclusive;
R$^1$ is hydrogen or —CH$_2$—O—CH$_2$—CHs; and
R$^2$ is hydrogen or hydroxyl.

In particular conjugates of Formula III, L is selected from, for example, —CH$_2$—, —CH$_2$—CH$_2$—NH—C(O)—CH$_2$—, —CH$_2$—CH$_2$—CH$_2$—, —CHFCH$_2$—NH—C(O)—CH$_2$—, CH$_2$—NH—C(O)—CH$_2$—, —CH(CH$_3$)—NH—C(O)—CH$_2$—, CH$_2$—CH(CH(CH$_3$)$_2$)—NH—C(O)—CH$_2$—, —CH$_2$—CH(CH$_2$CH(CH$_3$)$_2$)—NH—C(O)—CH$_2$—, C(CH$_3$)$_2$—NH—C(O)—CH$_2$—, a single bond, and —NH—CH$_2$—CH$_2$—.

Some specific embodiments of Formula III are as follows.

For example, in some embodiments, each n is independently an integer from 100 to 250, inclusive.

In some embodiments, R$^1$ is hydrogen and R$^2$ is hydrogen.

In yet further embodiments, R$^1$ is —CH$_2$—O—CH$_2$—CH$_3$ and R$^2$ is hydroxyl.

In one or more embodiments, the TLR 7/8 agonist is a 20,000 dalton 4-arm-pentaerythritolyl-based polyethylene glycol conjugate having a TLR agonist molecule such as resiquimod or imiquimod covalently linked, either stably or releasably, at the terminus of each of its four polymer arms. In yet one or more embodiments, the TLR 7/8 agonist molecule is resiquimod.

In certain embodiments, the long-acting TLR agonist is a 4-arm-pentaerythritolyl-based polyethylene glycol conjugate having resiquimod (R848) releasably covalently linked at the terminus of each of its four polymer arms and having the following structure.

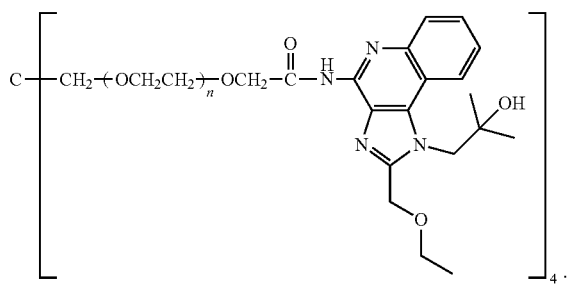

The foregoing TLR agonist multi-arm polymer conjugate is referred to herein as "4-arm-PEG-CM-N-R848", where N-indicates linkage to an amino group of the TLR agonist molecule, R848; its preparation is described in Example 3.

Particular multi-armed conjugates have structures as follows. That is to say, in some embodiments, a multi-armed polymer conjugate (e.g. a long-acting TLR agonist has the structure any of Compounds 1-10 or 12-16:

Compound 1

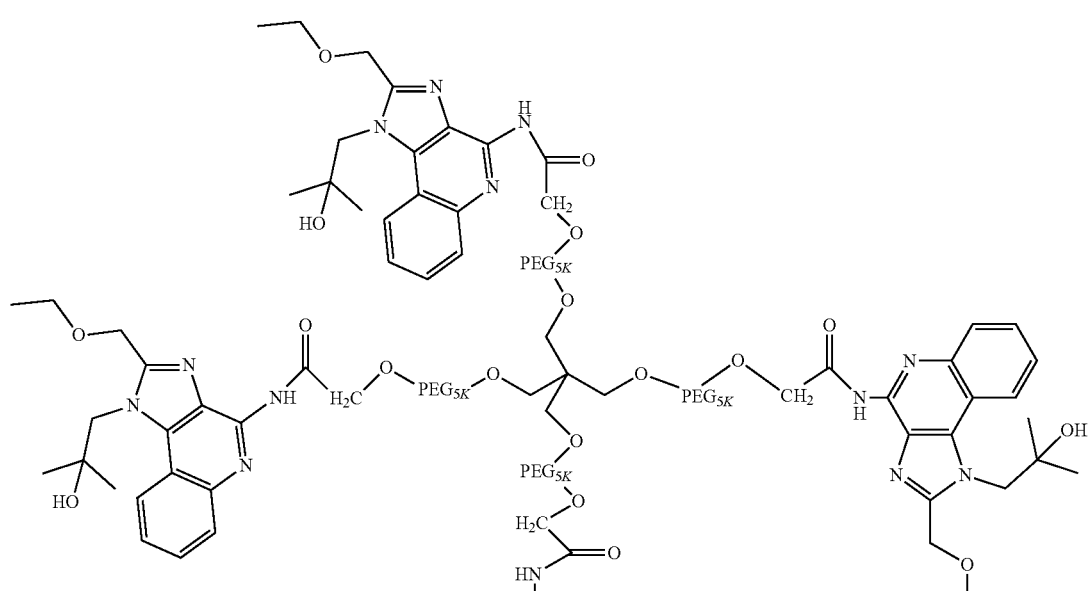

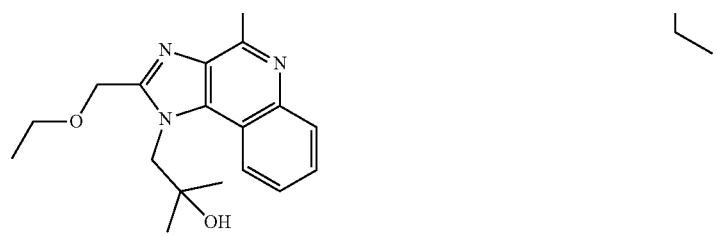

-continued
Compound 2
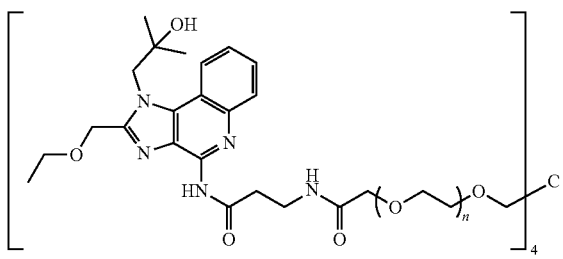
Compound 3
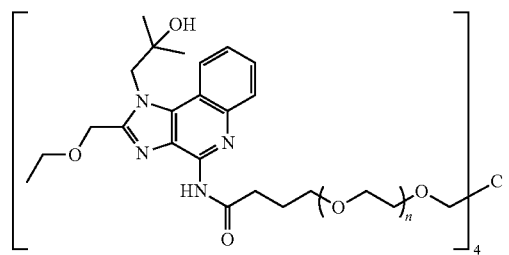
Compound 4
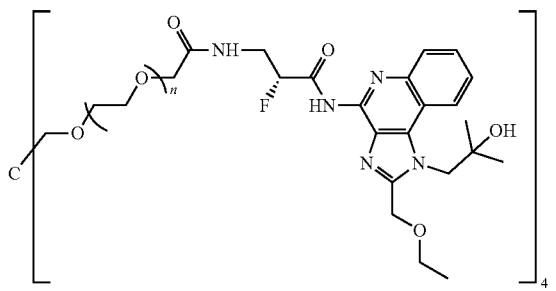
Compound 5
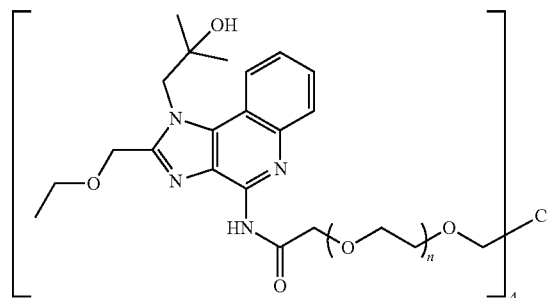
Compound 6
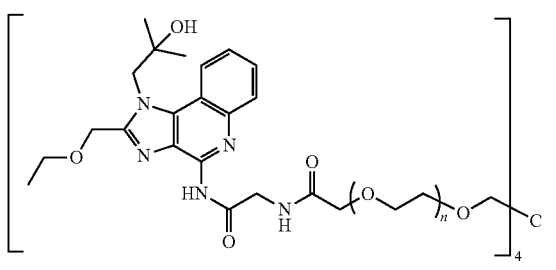
Compound 7
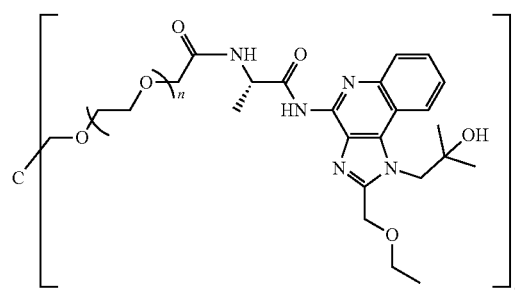
Compound 8
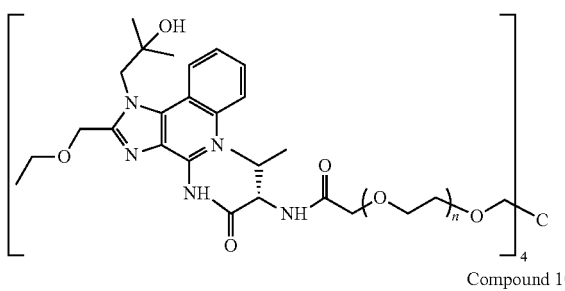
Compound 9
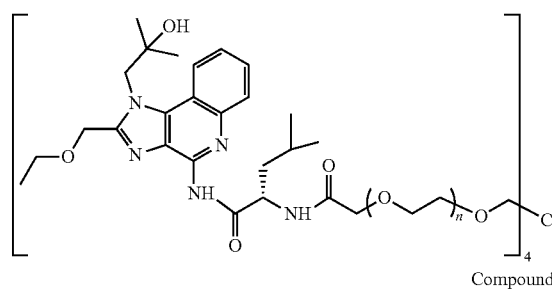
Compound 10
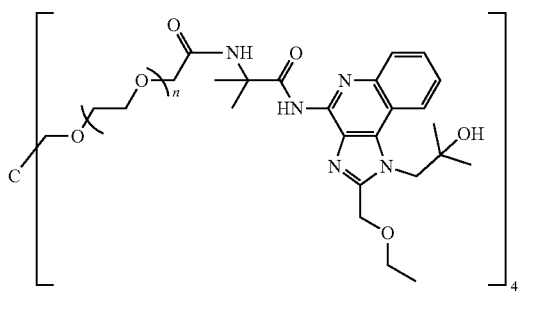
Compound 12
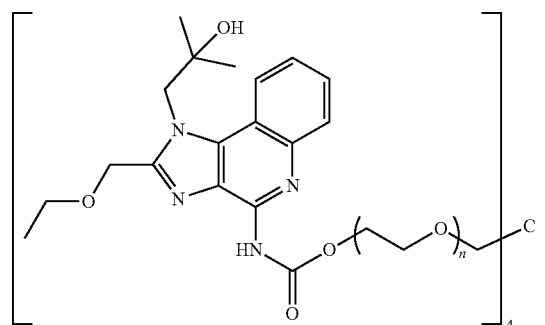

-continued

Compound 13

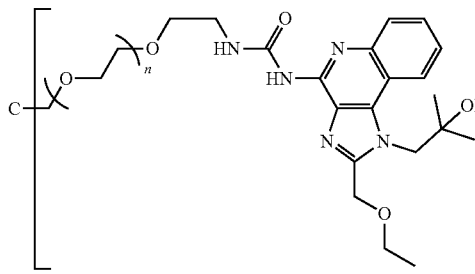

Compound 14

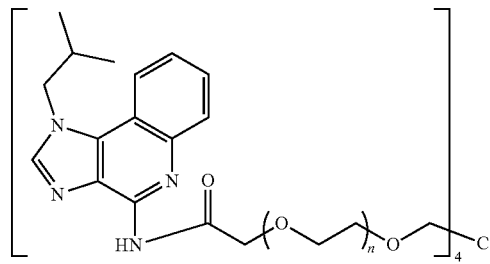

Compound 15

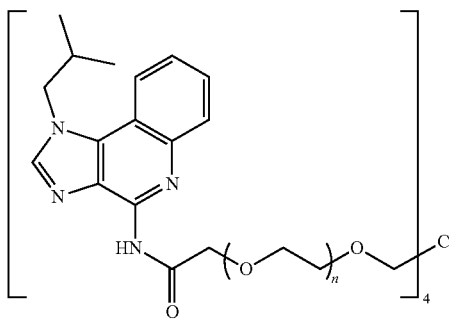

Compound 16

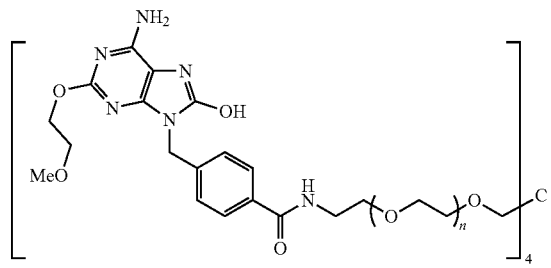

or a pharmaceutically acceptable salt or stereoisomer thereof.

In certain embodiments, the TLR agonist is Compound 11 having the structure shown below where n is any suitable number of repeat units as described herein.

Compound 11

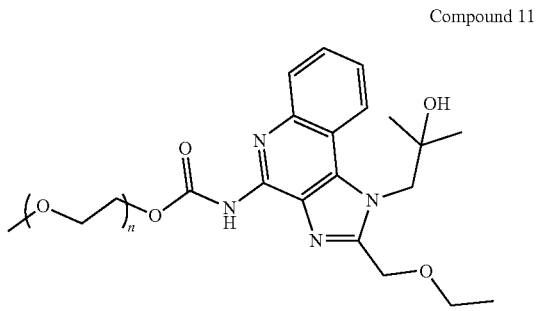

In yet some other preferred embodiments, the TLR agonist compound is Compound 6, having the structure shown below, where n is any suitable number of repeat units as described herein:

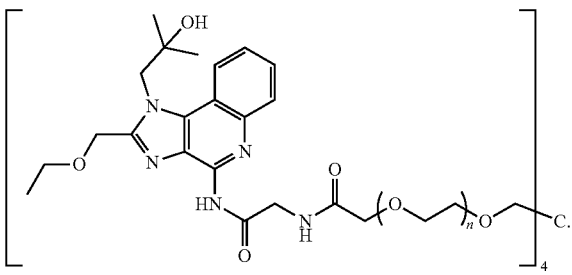

In some embodiments of Compounds 1-10 or 12-16, the overall multi-arm PEG portion of the compound has a weight average molecular weight of about 10,000 daltons. In yet some other embodiments of Compounds 1-10 or 12-16, the overall multi-arm PEG portion of the compound has a weight average molecular weight of about 20,000 daltons. In yet some other embodiments of Compounds 1-10 or 12-16, the overall multi-arm PEG portion of the compound has a weight average molecular weight of about 30,000 daltons. In yet some additional embodiments of Compounds 1-10 or 12-16, the overall multi-arm PEG portion of the compound has a weight average molecular weight of about 40,000 daltons. In some preferred embodiments of Compounds 1-10 or 12-16, the overall multi-arm PEG portion of the compound has a weight average molecular weight of about 20,000 daltons.

In some embodiments, due to incomplete chemical conversion (i.e., covalent coupling to a TLR 7/8 agonist), less than 100% yields, and/or other unavoidable complications routinely encountered during chemical syntheses, exemplary compositions comprising a multi-arm polymer conjugate will comprise fewer than the idealized number of TLR 7/8 agonist compounds attached to each of the number of "q" polymer arms. Such number is typically referred as degree of polymer loading, wherein 100% loading represents complete loading such that a TLR 7/8 agonist compound is covalently attached to the terminus of each of "q" polymer arms. For instance, an exemplary "4-arm-PEG" conjugate may be characterized as a mixture comprising four-arm conjugates, wherein at least 50 area percent (a/a, as measured by HPLC) of the four-arm conjugates in the composition have each of the four arms conjugated to a TLR 7/8 agonist. Further exemplary compositions comprising an exemplary "4-arm-PEG" conjugate may be characterized as compositions comprising four-arm conjugates, wherein at least 65-90, 70-85, or 70-75 area percent (a/a, as measured by HPLC) of the four-arm conjugates in the composition have each of the four arms conjugated to a TLR 7/8 agonist.

The conjugates may be administered per se or in the form of a pharmaceutically acceptable salt, and any reference to the any one or more of the multi-arm polymer conjugates herein is intended to include its pharmaceutically acceptable salts. If used, a salt of a conjugate as described herein should be both pharmacologically and pharmaceutically acceptable. Such pharmacologically and pharmaceutically acceptable salts may be prepared by reaction of the conjugate with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, malonic, succinic, naphthalene-2-sulphonic and benzenesulphonic, trifluoracetic acid, and the like. Also, pharmaceutically acceptable salts may be prepared as alkaline metal or alkaline earth salts, such as sodium, potassium, or calcium salts of a carboxylic acid group.

The conjugates, and in particular, the TLR 7/8 agonist portions of the conjugates, may contain one or more chiral centers. For each chiral center comprised therein, the instant compounds and structures are intended to encompass each optical isomer as well as any combination or ratio of or an optically active form, for example, a single optically active enantiomer, or any combination or ratio of enantiomers (e.g., scalemic and racemic mixtures).

Also provided herein are pharmaceutical preparations and compositions comprising a multi-arm polymer conjugate of a TLR 7/8 agonist as described herein. In one or more embodiments, the multi-arm TLR 7/8 agonist conjugate itself will be in a solid form (e.g., a precipitate).

The TLR agonist may be administered by any suitable administration route, for example, intradermal, intravenous, subcutaneous, intranodel, intralymphatic, intratumoral, and the like. In one or more particular embodiments of the method, the TLR agonist is administered directly to the tumor, for example, by injection, in an amount effective to activate innate immunity in a subject.

Long-Acting, IL-2Rβ-Biased Agonist

The methods, formulations, systems, kits, compositions, combinations and the like described herein may additionally involve the administration of a long-acting, IL-2Rβ-biased agonist. In this regard, the disclosure is not limited to any particular long-acting, IL-2Rβ-biased agonist so long as the agonist exhibits an in vitro binding affinity for IL-2Rβ that is at least 5 times greater (more preferably at least 10 times greater) than the binding affinity for IL-2Rαβ in the same in vitro model, and has at least an effective 10-fold in vivo half-life greater than IL-2 (half-life based on the in-vivo disappearance of IL-2). By way of example, it is possible to measure binding affinities against IL-2 as a standard. In this regard, the exemplary long-acting, IL-2Rβ-biased agonist, multi(2,7-(bis-methoxyPEG-carboxyamide)(9H-fluorene-9-yl)methyl N-carbamate)interleukin-2 (also referred to herein as "RSLAIL-2") referenced in Example 1 exhibits about a 60-fold decrease in affinity to IL-2Rαβ relative to IL-2, but only about a 5-fold decrease in affinity IL-2Rβ relative to IL-2.

Non-limiting examples of long-acting, IL-2Rβ-biased agonists are described in International Patent Publication No. WO 2012/065086 and in WO 2015/125159, incorporated herein by reference. An exemplary long-acting, IL-2Rβ-biased agonist is multi(2,7-(bis-methoxyPEG-carboxyamide)(9H-fluorene-9-yl)methyl N-carbamate)interleukin-2 ("RSLAIL-2") referenced in Example 1 below, where the releasable PEG is based upon a 2,7,9-substituted fluorene as shown below, with poly(ethylene glycol) chains extending from the 2- and 7-positions on the fluorene ring via amide linkages (fluorene-C(O)—NH~), and releasable covalent attachment to IL-2 (interleukin-2) via attachment to a carbamate nitrogen atom attached via a methylene group (—CH$_2$—) to the 9-position of the fluorene ring. In this regard, RSLAIL-2 is a composition comprising compounds encompassed by the following formula:

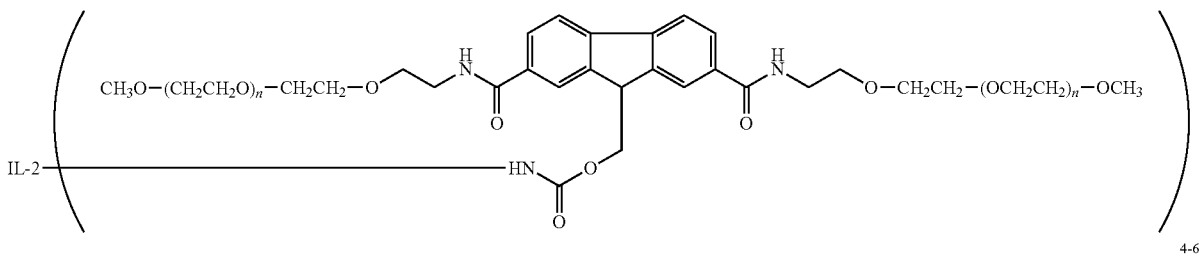

wherein IL-2 is an interleukin-2 (such as, for example, aldesleukin), including pharmaceutically acceptable salts thereof, where "n" is independently an integer from about 3 to about 4000. RSLAIL-2 is also referred to as 2,7-(bis-methoxyPEG-carboxyamide)(9H-fluorene-9-yl)methyl N-carbamate)$_{4-6}$interleukin-2.

In one or more embodiments, the 2,7-(bis-methoxyPEG-carboxyamide)(9H-fluorene-9-yl)methyl N-carbamate)$_{4-6}$interleukin-2 composition described above contains no more than 10% (based on a molar amount), and preferably no more than 5% (based on a molar amount), of compounds encompassed by the following formula

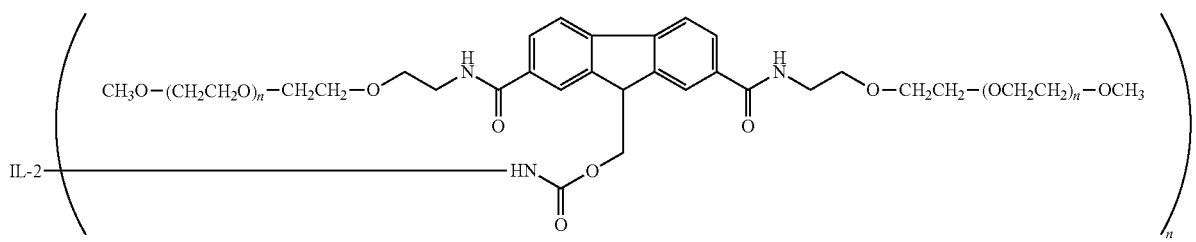

wherein IL-2 is an interleukin-2, (n) (referring to the number of polyethylene glycol moieties attached to IL-2) is an integer selected from the group consisting of 1, 2, 3, 7 and >7; and pharmaceutically acceptable salts thereof.

In yet some further embodiments, RSLAIL-2 possesses on average about six polyethylene glycol moieties attached to IL-2 (also referred to as 2,7-(bis-methoxyPEG-carboxy-amide)(9H-fluorene-9-yl)methyl N-carbamate)$_{6avg}$interleukin-2. In some further embodiments, RSLAIL-2 is generally considered to be an inactive prodrug, i.e., inactive upon administration, and by virtue of slow release of the polyethylene glycol moieties in vivo, providing active conjugated forms of interleukin-2, effective to achieve sustained concentrations at a tumor site.

In reference to the structures in this section, representative ranges for each "n" include, for example, an integer from about 40 to about 550, or an integer from about 60 to about 500, or an integer from about 113 to about 400, or from 200-300. In certain embodiments, "n" in each of the polyethylene glycol chains is about 227 (i.e., where each polyethylene glycol chain extending from the central fluorenyl core has a weight average molecular weight of about 10,000 Daltons, such that the weight average molecular weight of the overall branched PEG moiety is about 20,000 Daltons), i.e., referred to herein as multi(2,7-(bis-methoxyPEG$_{10kD}$-carboxyamide)(9H-fluorene-9-yl)methyl N-carbamate)interleukin-2 or as (2,7-(bis-methoxyPEG$_{10kD}$-carboxyamide)(9H-fluorene-9-yl)methyl N-carbamate)$_{4-6}$interleukin-2, having structures as shown below:

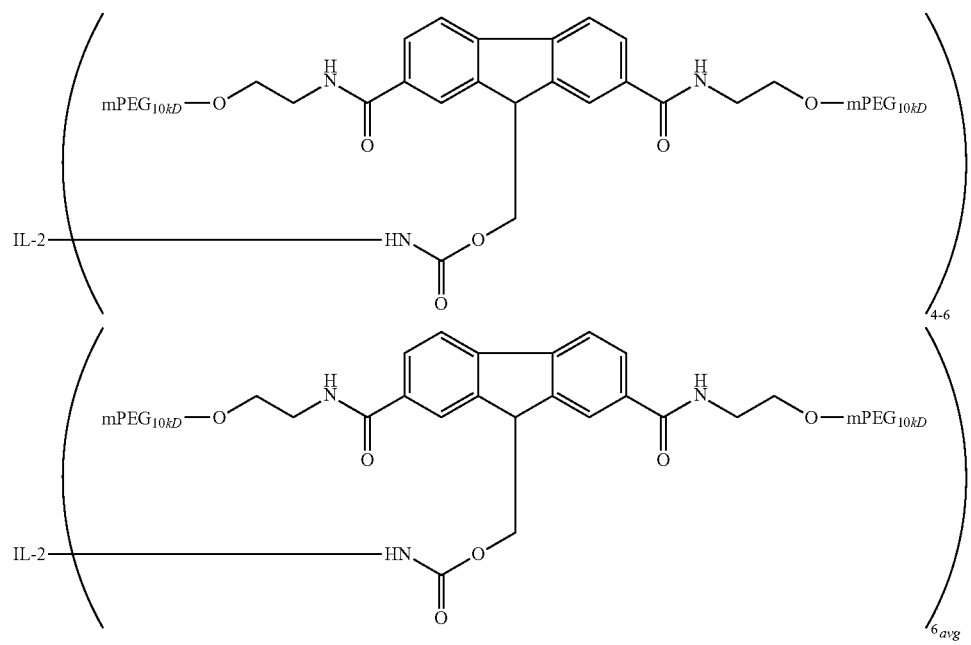

Additional exemplary compositions of RSLAIL-2 comprise compounds in accordance with the above formulae wherein the overall polymer portion of the molecule has a weight average molecular weight in a range of from about 250 daltons to about 90,000 daltons. Additional suitable ranges include weight average molecular weights in a range selected from about 1,000 daltons to about 60,000 daltons, in a range of from about 5,000 daltons to about 60,000 daltons, in a range of about 10,000 daltons to about 55,000 daltons, in a range of from about 15,000 daltons to about 50,000 daltons, and in a range of from about 20,000 daltons to about 50,000 daltons.

Additional illustrative weight-average molecular weights for the polyethylene glycol polymer portion include about 200 daltons, about 300 daltons, about 400 daltons, about 500 daltons, about 600 daltons, about 700 daltons, about 750 daltons, about 800 daltons, about 900 daltons, about 1,000 daltons, about 1,500 daltons, about 2,000 daltons, about 2,200 daltons, about 2,500 daltons, about 3,000 daltons, about 4,000 daltons, about 4,400 daltons, about 4,500 daltons, about 5,000 daltons, about 5,500 daltons, about 6,000 daltons, about 7,000 daltons, about 7,500 daltons, about 8,000 daltons, about 9,000 daltons, about 10,000 daltons, about 11,000 daltons, about 12,000 daltons, about 13,000 daltons, about 14,000 daltons, about 15,000 daltons, about 20,000 daltons, about 22,500 daltons, about 25,000 daltons, about 30,000 daltons, about 35,000 daltons, about 40,000 daltons, about 45,000 daltons, about 50,000 daltons, about 55,000 daltons, about 60,000 daltons, about 65,000 daltons, about 70,000 daltons, and about 75,000 daltons. In some embodiments, the weight-average molecular weight of the polyethylene glycol polymer is about 20,000 daltons.

As described above, the long-acting, IL-2Rβ-biased agonist may be in the form of a pharmaceutically-acceptable salt (as is the case for the TLR agonist). Typically, such salts are formed by reaction with a pharmaceutically-acceptable acid or an acid equivalent. The term "pharmaceutically-acceptable salt" in this respect, will generally refer to the relatively non-toxic, inorganic and organic acid addition salts. These salts may be prepared in situ in the administration vehicle or the dosage form manufacturing process, or by separately reacting a long-acting interleukin-2 as described herein with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, oxylate, mesylate, glucoheptonate, lactobionate, and laurylsulphonate salts and the like. (See, for example, Berge et al. (1977) "*Pharmaceutical Salts*", *J. Pharm. Sci.* 66:1-19). Thus, salts as described may be derived from inorganic acids such as hydrochloride, hydrobromic, sulfuric, sulfamic, phosphoric, nitric, and the like; or prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In reference to the foregoing IL-2Rβ-biased agonist, the term "IL-2" as used herein, refers to a moiety having human IL-2 activity. The term, 'residue', in the context of residue of IL-2, means the portion of the IL-2 molecule that remains following covalent attachment to a polymer such as a polyethylene glycol, at one or more covalent attachment sites, as shown in the formula above. It will be understood that when the unmodified IL-2 is attached to a polymer such as polyethylene glycol, the IL-2 is slightly altered due to the presence of one or more covalent bonds associated with linkage to the polymer(s). This slightly altered form of the IL-2 attached to another molecule may, in some instances, be referred to a "residue" of the IL-2.

For example, proteins having an amino acid sequence corresponding to any one of SEQ ID NOs: 1 through 4 described in International Patent Publication No. WO 2012/065086 are exemplary IL-2 proteins, as are any proteins or polypeptides substantially homologous thereto. The term substantially homologous means that a particular subject sequence, for example, a mutant sequence, varies from a reference sequence by one or more substitutions, deletions, or additions, the net effect of which does not result in an adverse functional dissimilarity between the reference and subject sequences. For the purposes herein, sequences having greater than 95 percent homology, equivalent biological activity (although not necessarily equivalent strength of biological activity), and equivalent expression characteristics are considered substantially homologous. For purposes of determining homology, truncation of the mature sequence should be disregarded. As used herein, the term "IL-2" includes such proteins modified deliberately, as for example, by site directed mutagenesis or accidentally through mutations. These terms also include analogs having from 1 to 6 additional glycosylation sites, analogs having at least one additional amino acid at the carboxy terminal end of the protein wherein the additional amino acid(s) includes at least one glycosylation site, and analogs having an amino acid sequence which includes at least one glycosylation site. The term includes both natural and recombinantly produced moieties. In addition, the IL-2 may be derived from human sources, animal sources, and plant sources. One exemplary IL-2 is recombinant IL-2 referred to as aldesleukin.

Conventional approaches, such as those involving radiolabeling a compound, administering it in vivo, and determining its clearance, may be used to determine whether a compound proposed to be a long-acting IL-2Rβ biased agonist is "long-acting". For the purposes herein, the long-acting nature of an IL-2Rβ biased agonist is typically determined using flow cytometry to measure STAT5 phosphorylation in lymphocytes at various time points after administration of the agonist to be evaluated in mice. As a reference, the signal is lost by around 24 hours with IL-2, but is sustained for a period greater than that for a long-acting IL-2Rβ-biased agonist. As an illustration, the signal is sustained over several days for the RSLAIL-2 compositions.

Considering now the IL-2Rβ bias of a long-acting agonist as described herein, Example 2 provides both in-vitro and in-vivo data related to receptor bias for exemplary compositions of RSLAIL-2. As described in Example 2, in a murine melanoma tumor model, the ratio of CD8/regulatory T cells for RSLAIL-2 when compared to IL-2 supports preferential activation of the IL-2 receptor beta over IL2 receptor alpha. Exemplary long-acting IL-2Rβ biased agonists such as RSLAIL-2 are, for example, effective to preferentially activate and expand effector CD8+ T- and NK-cells over Tregs.

Moreover, representative long-acting IL-2Rβ-biased agonists such as RSLAIL-2 provide increased tumor exposure, and preferably significantly enhanced tumor exposure relative to IL-2, for example, at least a 50-fold increased exposure, or at least a 100-fold increased exposure, or at least a 200-fold increased exposure, or at least a 300-fold increased exposure, or at least a 400-fold increased exposure, or at least a 500-fold increased exposure when normalized for equivalents of IL-2.

Methods, Compositions, and Kits

In accordance with the methods, combinations, compositions, formulations, systems and kits described herein, the long-acting, IL-2Rβ-biased agonist is provided in an IL-2Rβ-activating amount. One of ordinary skill in the art may determine how much of a given long-acting, IL-2Rβ-biased agonist is sufficient to provide clinically relevant agonistic activity at IL-2Rβ. For example, one of ordinary skill in the art may refer to the literature and/or administer a series of increasing amounts of the long-acting, IL-2Rβ-biased agonist and determine which amount or amounts provide clinically effective agonistic activity of IL-2Rβ. Alternatively, an activating amount of the long-acting IL-2Rβ-biased agonist may be determined using the in vivo STAT5 phosphorylation assay described above and known in the art (determined in vivo following administration)

where an amount sufficient to induce STAT5 phosphorylation in greater than 10% of NK cells at peak is considered to be an activating amount.

In one or more instances, however, the IL-2Rβ-activating amount is an amount encompassed by one or more of the following ranges expressed in amount of protein: from about 0.01 to 100 mg/kg; from about 0.01 mg/kg to about 75 mg/kg; from about 0.02 mg/kg to about 60 mg/kg; from about 0.03 mg/kg to about 50 mg/kg; from about 0.05 mg/kg to about 40 mg/kg; from about 0.05 mg/kg to about 30 mg/kg; from about 0.05 mg/kg to about 25 mg/kg; from about 0.05 mg/kg to about 15 mg/kg; from about 0.05 mg/kg to about 10 mg/kg; from about 0.05 mg/kg to about 5 mg/kg; from about 0.05 mg/kg to about 1 mg/kg. In some embodiments, the long-acting IL-2Rβ-biased agonist is administered at a dose that is less than or equal to 0.7 mg/kg. Particular illustrative dosing ranges include for example, from about 0.1 mg/kg to about 10 mg/kg, or from about 0.2 mg/kg to about 7 mg/kg, or from about 0.2 mg/kg to less than about 0.7 mg/kg.

In certain embodiments, a dose of long acting IL-2Rβ-biased agonist, multi(2,7-(bis-methoxyPEG-carboxyamide)(9H-fluorene-9-yl)methyl N-carbamate)interleukin-2, used in the compositions and methods provided herein, is administered about once every 3 weeks.

In certain additional embodiments, the amount of the long acting IL-2Rβ-biased agonist, multi(2,7-(bis-methoxyPEG-carboxyamide)(9H-fluorene-9-yl)methyl N-carbamate)interleukin-2, used in the compositions, combinations and methods provided herein is from about 0.0005 to 0.3 mg/kg; from about 0.001 mg/kg to about 0.3 mg/kg; from about 0.001 mg/kg to about 0.25 mg/kg; from about 0.001 mg/kg to about 0.15 mg/kg; from about 0.001 mg/kg to about 0.05 mg/kg; from about 0.001 mg/kg to about 0.01 mg/kg; from about 0.001 mg/kg to about 0.008 mg/kg; from about 0.001 mg/kg to about 0.005 mg/kg; from about 0.002 mg/kg to about 0.005 mg/kg; from about 0.002 mg/kg to about 0.004 mg/kg.

In some embodiments, the long acting IL-2Rβ-biased agonist, multi(2,7-(bis-methoxyPEG-carboxyamide)(9H-fluorene-9-yl)methyl N-carbamate) interleukin-2, is administered at a dose that is less than or equal to 0.003 mg/kg. In certain embodiments, the dosing ranges include for example, from about 0.001 mg/kg to about 0.01 mg/kg, or from about 0.002 mg/kg to about 0.008 mg/kg, or from about 0.002 mg/kg to less than about 0.006 mg/kg. In yet some other embodiments of the method, multi(2,7-(bis-methoxyPEG-carboxyamide)(9H-fluorene-9-yl)methyl N-carbamate)interleukin-2 is administered at a dose of from about 0.006 mg/kg to about 0.010 mg/kg. In certain embodiments, a dose of long acting IL-2Rβ-biased agonist, multi(2,7-(bis-methoxyPEG-carboxyamide)(9H-fluorene-9-yl)methyl N-carbamate)interleukin-2, used in the compositions and methods provided herein is administered once every 3 weeks, e.g., within a dosage range selected from the above.

For confirmation, with respect to the long-acting, IL-2Rβ-biased agonist, the amount and extent of the activation can vary widely and still be effective when coupled with administration of a PD-1/PD-L1 axis inhibitor alone or in combination with a TLR agonist. That is to say, an amount of a long-acting, IL-2Rβ-biased agonist that exhibits only minimal agonist activity at IL-2Rβ for a sufficiently extended period of time can still be a long-acting, IL-2Rβ-biased agonist so long as when administered with a PD-1/PD-L1 axis inhibitor and, optionally, a TLR agonist, the methods, compositions, and kits described herein enable a clinically meaningful response. In some instances, due to (for example) synergistic interactions and responses, only minimal agonist activity of IL-2Rβ may be required when accompanied by administration of a PD-1/PD-L1 axis inhibitor and, optionally, a TLR agonist (e.g., a long-acting TLR agonist). Similarly, the dosage amount of the PD-1/PD-L1 axis inhibitor and/or the TLR agonist when used in the combinations described herein may be considered to be a "sub-therapeutic" dose when the agent is administered singly, however, when used as part of a bi-modal or tri-modal therapeutic strategy as provided herein, such doses may result in a clinically meaningful response.

The treatment methods described herein may continue for as long as the clinician overseeing the patient's care deems the treatment method to be effective. Non-limiting parameters that indicate the treatment method is effective include any one or more of the following: tumor shrinkage (in terms of weight and/or volume); a decrease in the number of individual tumor colonies; tumor elimination; and progression-free survival. Change in tumor size may be determined by any suitable method such as imaging. Various diagnostic imaging modalities may be employed, such as computed tomography (CT scan), dual energy CDT, positron emission tomography and MRI.

The actual doses of the PD-1/PD-L1 axis inhibitor, the long-acting, IL-2Rβ-biased agonist, and the TLR agonist to be administered, as well as the dosing regimen associated with the methods, compositions, formulations, systems, and kits described herein will vary depending upon the age, weight, and general condition of the subject as well as the type and severity of the condition being treated (e.g., progression of the cancer being treated), the judgment of the health care professional, and the particular PD-1/PD-L1 axis inhibitor, long-acting, IL-2Rβ-biased agonist, and TLR agonist to be administered. Therapeutically effective amounts are known to those skilled in the art and/or are described in the pertinent reference texts and literature, or can be determined. Generally, a therapeutically effective amount of a TLR agonist (based on active molecule) will range from about 0.001 mg to 1000 mg, preferably in doses from 0.01 mg/day to 750 mg/day, and more preferably in doses from 0.10 mg/day to 500 mg/day.

Generally, a therapeutically effective amount of a PD-1/PD-1L axis inhibitor may be between about 1 mg/kg body weight to about 1000 mg/kg body weight, from about 1 to 800 mg/kg, from about 1 to 500 mg/kg, from about 1 to 250 mg/kg, from about 1 to 200 mg/kg, from about 1 to 150 mg/kg, from about 1 to 100 mg/kg, from about 1 to 50 mg/kg, from about 1 to 25 mg/kg, from about 1 to 20 mg/kg, from about 1 to 15 mg/kg, from about 1 to 10 mg/kg, from about 1 to 5 mg/kg, from about 2 mg/kg body weight to about 1000 mg/kg body weight, from about 2 to 800 mg/kg, from about 2 to 500 mg/kg, from about 2 to 250 mg/kg, from about 2 to 200 mg/kg, from about 2 to 150 mg/kg, from about 2 to 100 mg/kg, from about 2 to 50 mg/kg, from about 2 to 25 mg/kg, from about 2 to 20 mg/kg, from about 2 to 15 mg/kg, from about 2 to 10 mg/kg, from about 2 to 5 mg/kg, from about 3 mg/kg body weight to about 1000 mg/kg body weight, from about 3 to 800 mg/kg, from about 3 to 500 mg/kg, from about 3 to 250 mg/kg, from about 3 to 200 mg/kg, from about 3 to 150 mg/kg, from about 3 to 100 mg/kg, from about 3 to 50 mg/kg, from about 3 to 25 mg/kg, from about 3 to 20 mg/kg, from about 3 to 15 mg/kg, from about 3 to 10 mg/kg, from about 3 to 5 mg/kg, from about 5 mg/kg body weight to about 1000 mg/kg body weight, from about 5 to 800 mg/kg, from about 5 to 500 mg/kg, from about 5 to 250 mg/kg, from about 5 to 200 mg/kg, from about 5 to 150 mg/kg, from about 5 to 100 mg/kg, from about 5 to 50 mg/kg, from about 5 to 25 mg/kg, from about 5 to 20 mg/kg, from about 5 to 15 mg/kg, from about 5 to 10 mg/kg, from about 10 mg/kg body weight to about 1000 mg/kg body weight, from about 10 to 800 mg/kg, from about 10 to 500 mg/kg, from about 10 to 250 mg/kg, from about 10 to 200 mg/kg, from about 10 to 150 mg/kg, from about 10 to 100 mg/kg, from about 10 to 50 mg/kg, from about 10 to 25 mg/kg, from about 10 to 20 mg/kg, from about 10 to 15 mg/kg, from about 100 to 1000 mg/kg, from about 100 to 500 mg/kg, from about 100 to 250 mg/kg, from about 100 to 200 mg/kg, from about 150 to 1000 mg/kg, from about 150 to 500 mg/kg, from about 150 to 250 mg/kg, from about 150 to 200 mg/kg, from about 200 to 1000 mg/kg, from about 200 to 500 mg/kg, from about 200 to 250 mg/kg, from about 250 to 1000 mg/kg, from about 250 to 500 mg/kg, or from about 500 to 1000 mg/kg. In embodiments, a pharmacologically effective amount may be about 100 to 1000 mg, about 100 to 500 mg, about 100 to 250, about 100 to 200, about 200 to 1000 mg, about 200 to 500 mg, about 200 to 250, about 250 to 1000 mg, about 250 to 500 mg, or about 500 to 1000 mg. In some embodiments, the PD-1/PD-L1 axis inhibitor is nivolumab administered at a dose of from about 100 my to about 500 mg.

The unit dosage of any of a PD-1/PD-L1 axis inhibitor, TLR agonist and/or long-acting, IL-2Rβ-biased agonist (again, preferably provided as part of a pharmaceutical preparation) may be administered in a variety of dosing schedules depending on the judgment of the clinician, needs of the patient, and so forth. The specific dosing schedule will be known by those of ordinary skill in the art or may be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted. In some embodiments, the PD-1/PD-1L axis inhibitor is administered intermittently.

With regard to the frequency and schedule of administering the PD-1/PD-L1 axis inhibitor, the long-acting, IL-2Rβ-biased agonist, and/or the TLR agonist, one of ordinary skill in the art will be able to determine an appropriate frequency. For example, in a treatment cycle, a clinician can decide to administer the TLR agonist, either as a single dose or in a series of doses, e.g., over the course of several days or weeks. The same is true for the PD-1/PD-L1 axis inhibitor and the long-acting, IL-2Rβ-biased agonist. Each of the PD-1/PD-L1 axis inhibitor, the long-acting, IL-2Rβ-biased agonist, and the TLR agonist may be administered before, with, or after administration of the other of the PD-1/PD-L1 axis inhibitor, the long-acting, IL-2Rβ-biased agonist, and the TLR agonist.

It will be appreciated that the PD-1/PD-L1 axis inhibitor may be administered together with or separate from either or both of the TLR agonist and the long-acting, IL-2Rβ-biased agonist. In embodiments, the PD-1/PD-L1 axis inhibitor may be administered together with either of the TLR agonist or the long-acting, IL-2Rβ-biased agonist, but separately from the other of the TLR agonist or the long-acting, IL-2Rβ-biased agonist. In some embodiments, the PD-1/PD-L1 axis inhibitor is administered separately from each of the TLR agonist and/or the long-acting, IL-2Rβ-biased agonist (depending on which or both are being administered). It will be appreciated that the TLR agonist and the long-acting, IL-2Rβ-biased agonist, when both are included, may be administered together. In one particular embodiment, the PD-1/PD-L1 axis inhibitor and the long-acting, IL-2Rβ-biased agonist are administered concurrently or together (either in the same formulation or in separate formulations). It will be appreciated that the PD-1/PD-L1 axis inhibitor, the TLR agonist and/or the long-acting, IL-2Rβ-biased agonist may be administered in any order. Further, administration of any or all of the PD-1/PD-L1 axis inhibitor, the TLR agonist and/or the long-acting, IL-2Rβ-biased agonist may be separated by minutes, hours, or days as needed.

In some treatment regimens, the TLR agonist is administered at least as a single dose at the commencement of treatment. The long-acting, IL-2Rβ-biased agonist and/or the PD-1/PD-L1 axis inhibitor are administered, either concurrently with the TLR agonist, prior to administration of the TLR agonist, or following administration of the TLR agonist. For example, in some treatment modalities, the long-acting, IL-2Rβ-biased agonist and/or PD-1/PD-L1 axis inhibitor are administered within 7 days (before or after) of TLR agonist administration (e.g., on any one of days 1, 2, 3, 4, 5, 6, or 7), where day 1 indicates commencement of treatment. In some treatment regimens, the long-acting, IL-2Rβ-biased agonist and/or the PD-1/PD-L1 axis inhibitor are administered within 4 days of administration of the TLR agonist, e.g., on any one of days 1, 2, 3, or 4. Based upon the long-acting nature of the IL-2Rβ-biased agonist, such compound is typically administered relatively infrequently (e.g., once every three weeks, once every two weeks, once every 8-10 days, once every week, etc.).

Exemplary lengths of time associated with the course of therapy include about one week; about two weeks; about three weeks; about four weeks; about five weeks; about six weeks; about seven weeks; about eight weeks; about nine weeks; about ten weeks; about eleven weeks; about twelve weeks; about thirteen weeks; about fourteen weeks; about fifteen weeks; about sixteen weeks; about seventeen weeks; about eighteen weeks; about nineteen weeks; about twenty weeks; about twenty-one weeks; about twenty-two weeks; about twenty-three weeks; about twenty four weeks; about seven months; about eight months; about nine months; about ten months; about eleven months; about twelve months; about thirteen months; about fourteen months; about fifteen months; about sixteen months; about seventeen months; about eighteen months; about nineteen months; about twenty months; about twenty one months; about twenty-two months; about twenty-three months; about twenty-four months; about thirty months; about three years; about four years and about five years.

The treatment methods described herein are typically continued for as long as the clinician overseeing the patient's care deems the treatment method to be effective, i.e., that the patient is responding to treatment). Non-limiting parameters that indicate the treatment method is effective may include one or more of the following: tumor shrinkage (in terms of weight and/or volume and/or visual appearance); a decrease in the number of individual tumor colonies; tumor elimination; progression-free survival; appropriate response by a suitable tumor marker (if applicable), increased number of NK (natural killer) cells, increased number of T cells, increased number of memory T cells, increased number of central memory T cells, reduced numbers of regulatory T cells such as CD4+ Tregs, CD25+ Tregs, and FoxP3+ Tregs.

The methods provided herein are useful for (among other things) treating a patient having cancer. For example, patients may be responsive to treatment with PD-1/PD-L1 axis inhibitor alone, to treatment with the TLR agonist alone, or to treatment with the long-acting, IL-2Rβ-biased agonist alone, as well as to the combination of the PD-1/PD-L1 axis inhibitor, the TLR agonist and/or the long-acting, IL-2Rβ-biased agonist—but are more responsive to a combination. By way of further example, patients may be non-responsive to any or all of the PD-1/PD-L1 axis inhibitor, the TLR agonist, or the long-acting, IL-2Rβ-biased agonist, but are responsive to a combination. By way of still further example, patients may be non-responsive to any of the PD-1/PD-L1 axis inhibitor, the TLR agonist, and the long-acting, IL-2Rβ-biased agonist when administered alone, but are responsive to a combination. In embodiments, a method of treating cancer comprises administering to a patient one or more pharmaceutical compositions comprising a PD-1/PD-L1 axis inhibitor and at least one of a TLR agonist and a long-acting, IL-2Rβ-biased agonist. In an embodiment, provided herein is a use of one or more pharmaceutical compositions as described herein in the preparation of a medicament which is useful in the treatment of cancer, such as a solid cancer.

Administration, e.g., of the PD-1/PD-L1 axis inhibitor, the TLR agonist, and/or the long-acting, IL-2Rβ-biased agonist is typically via injection. Other modes of administration are also contemplated, such as oral, pulmonary, nasal, buccal, rectal, sublingual, transdermal, intratumoral, and parenteral. As used herein, the term "parenteral" includes subcutaneous, intravenous, intra-arterial, intratumoral, intralymphatic, intraperitoneal, intracardiac, intrathecal, and intramuscular injection, as well as infusion injections. As described previously, the PD-1/PD-L1 axis inhibitor, the TLR agonist, and/or the long-acting, IL-2Rβ-biased agonist may be administered separately. Alternatively, if administration of the PD-1/PD-L1 axis inhibitor, the TLR agonist, and/or the long-acting, IL-2Rβ-biased agonist is desired to be simultaneous, either as an initial dose or throughout the course of treatment or at various stages of the dosing regimen—and the PD-1/PD-L1 axis inhibitor, the TLR agonist, and/or the long-acting, IL-2Rβ-biased agonist are compatible together and in a given formulation—then the simultaneous administration may be achieved via administration of a single dosage form/formulation (e.g., intravenous administration of an intravenous formulation that contains all of the immunological components). One of ordinary skill in the art can determine through routine testing whether such components are compatible together and in a given formulation.

The therapeutic combinations described herein, i.e., PD-1/PD-L1 axis inhibitor, the long-acting IL-2Rβ-biased agonist, and/or the TLR7/8 agonist, may be provided in the form of one or more compositions or formulations. It will be appreciated that the PD-1/PD-L1 axis inhibitor and at least one of the long-acting IL-2Rβ-biased agonist, and/or the TLR agonist may be provided in the same composition. In other embodiments, the PD-1/PD-L1 axis inhibitor and the long-acting IL-2Rβ-biased agonist, and/or the TLR agonist may each be provided in a separate composition. Generally, the compositions include one or more of the PD-1/PD-L1 axis inhibitor, the long-acting IL-2Rβ-biased agonist, and/or the TLR agonist in combination with a pharmaceutical excipient. The compositions described herein may be in solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient may also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Non-limiting examples of suitable antimicrobial agents include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant may be present in the preparation as well. Antioxidants are used to prevent oxidation, thereby preventing the deterioration of the conjugate or other components of the preparation. Suitable antioxidants include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as TWEEN® 20 and TWEEN® 80, and pluronics such as F68 and F88 (both of which are available from BASF, Mount Olive, NJ); sorbitan esters; lipids, such as phospholipids such as lecithin and other phosphatidylcholines, phosphatidylethanolamines, fatty acids and fatty esters; steroids, such as cholesterol; and chelating agents, such as ethylenediaminetetraacetic acid (EDTA), zinc and other such suitable cations.

Pharmaceutically acceptable acids or bases may be present as an excipient in the preparation. Non-limiting examples of acids that may be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

Other pharmaceutical excipients and/or additives suitable for use in the compositions according to the disclosure and related methods for formulation may be found in, for example, "Remington: The Science & Practice of Pharmacy", 22nd Ed., Remington: The Essentials of Pharmaceutics (2009); and in the "Physician's Desk Reference", 2017, and in "Handbook of Pharmaceutical Excipients", $7^{th}$ edition.

The amount of the PD-1/PD-L1 axis inhibitor, the long-acting IL-2n-biased agonist, and/or the TLR agonist in the composition will vary depending on a number of factors, but will optimally be a therapeutically effective dose when the composition is stored in a unit dose container. A therapeutically effective dose may be determined experimentally by repeated administration of increasing amounts of the PD-1/PD-L1 axis inhibitor, the long-acting IL-2Rβ-biased agonist, and/or the TLR agonist in order to determine which amount produces a clinically desired endpoint.

The amount of any individual excipient in the composition will vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

The pharmaceutical compositions can take any number of forms and the composition is not limited in this regard. Exemplary preparations may be in a form suitable for oral administration such as a tablet, caplet, capsule, gel cap, troche, dispersion, suspension, solution, elixir, syrup, lozenge, transdermal patch, spray, suppository, and powder. In preferred embodiments, the composition is a form suitable for intratumoral administration.

Oral dosage forms include tablets, caplets, capsules, gel caps, suspensions, solutions, elixirs, and syrups, and may also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, may be manufactured using standard tablet processing procedures and equipment. Direct compression and granulation techniques are generally preferred when preparing tablets or caplets containing the conjugates described herein. In addition to the PD-1/PD-L1 axis inhibitor, the long-acting IL-2Rβ-biased agonist, and/or the TLR agonist, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pre-gelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and magnesium aluminum silicate (e.g. VEEGUM®). Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or cross-linked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the composition containing the PD-1/PD-L1 axis inhibitor, the long-acting IL-2Rβ-biased agonist, and/or the TLR agonist may be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which may be in the form of a powder or cake), as well as formulations prepared for injection, which are liquid and require the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of non-aqueous solutions, suspensions, or emulsions, normally being sterile. Examples of non-aqueous solvents or vehicles are propylene glycol, polyethylene glycol, vegetable oils, such as olive oil and corn oil, gelatin, and injectable organic esters such as ethyl oleate.

The parenteral formulations described herein may also contain adjuvants such as preserving, wetting, emulsifying, and dispersing agents. The formulations are rendered sterile by incorporation of a sterilizing agent, filtration through a bacteria-retaining filter, irradiation, or heat.

The compositions or formulations may also be administered through the skin using conventional transdermal patch or other transdermal delivery system, wherein the PD-1/PD-L1 axis inhibitor, the long-acting IL-2Rβ-biased agonist, and/or the TLR agonist is contained within a laminated structure that serves as a drug delivery device to be affixed to the skin. In such a structure, the PD-1/PD-L1 axis inhibitor, the long-acting IL-2Rβ-biased agonist, and/or the TLR agonist is contained in a layer, or "reservoir," underlying an upper backing layer. The laminated structure may contain a single reservoir, or it may contain multiple reservoirs.

The PD-1/PD-L1 axis inhibitor, the long-acting IL-2Rβ-biased agonist, and/or the TLR agonist may also be formulated into a suppository for rectal administration. With respect to suppositories, the PD-1/PD-L1 axis inhibitor, the long-acting IL-2Rβ-biased agonist, and/or the TLR agonist is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories may be prepared by, for example, performing the following steps (not necessarily in the order presented): melting the suppository base material to form a melt; incorporating the PD-1/PD-L1 axis inhibitor, the long-acting IL-2Rβ-biased agonist, and/or the TLR agonist (either before or after melting of the suppository base material); pouring the melt into a mold; cooling the melt (e.g., placing the melt-containing mold in a room temperature environment) to thereby form suppositories; and removing the suppositories from the mold.

In some preferred embodiments, at least one combination and/or composition comprising at least one of the PD-1/PD-L1 axis inhibitor, the long-acting IL-2Rβ-biased agonist, and/or the TLR agonist is administered intratumorally, e.g., administered directly into a tumor, e.g., by injection. Such administration provides for a high concentration of, for example, the TLR agonist to be achieved in the tumor, with delayed release of the TLR agonist into the systemic circulation, and in the case of a conjugate comprising releasable linkages, into the tumor itself. An exemplary formulation for intratumoral administration of a multi-arm polymer conjugate of a TLR 7/8 agonist comprises Na/K phosphate buffer at pH 7.4.

In some embodiments, the compositions comprising the PD-1/PD-L1 axis inhibitor, the long-acting IL-2Rβ-biased agonist, and/or the TLR agonist may further be incorporated into a suitable delivery vehicle. Such delivery vehicles may provide controlled and/or continuous release of the conjugates and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodotorula* yeast cell particles (YCP). Yeast cells such as *S. cerevisiae* and *Rhodotorula* species are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495, 4,810,646, 4,992,540, 5,028,703, 5,607,677 and U.S. Patent Application Publication Nos. 2005/0281781 and 2008/0044438.

The therapeutic combinations described herein, i.e., the PD-1/PD-L1 axis inhibitor, the long-acting IL-2Rβ-biased agonist, and/or the TLR agonist, may be provided in the form of a kit. As described above, the components may be comprised in a single composition, optionally accompanied by one or more pharmaceutically acceptable excipients, or may be provided in separate containers, where the kit typically includes instructions for use. Suitable pharmaceutically acceptable excipients include those described, for example, in the Handbook of Pharmaceutical Excipients, 7th ed., Rowe, R. C., Ed., Pharmaceutical Press, 2012. The kit components, e.g., compositions comprising the PD-1/PD-L1 axis inhibitor, the TLR agonist and/or the long-acting IL-2Rβ-biased agonist, can be in either liquid or in solid form. In certain embodiments, the PD-1/PD-L1 axis inhibitor, the TLR agonist and/or the long-acting IL-2Rβ-biased agonist are in solid form. Representative solid forms are those that are solid dry forms, e.g., containing less than about 5 percent by weight water, or preferably less than 2 percent by weight water. The solid forms are generally suitable for reconstitution in an aqueous diluent.

Also provided is a method for administering a PD-1/PD-L1 axis inhibitor and at least one of a multi-arm polymer conjugate of a TLR agonist (e.g., a TLR 7/8 agonist) and a long-acting IL-2Rβ-biased agonist as provided herein to a patient suffering from a condition that is responsive to at least one of the PD-1/PD-L1 axis inhibitor, the multi-arm polymer conjugate of a TLR agonist (e.g., a TLR 7/8 agonist) and/or the long-acting IL-2Rβ-biased agonist, such as for example, a patient having cancer. The method comprises administering a therapeutically effective amount of the composition or compositions (preferably provided as part of a pharmaceutical preparation).

The presently described methods, kits and related compositions may be used to treat a patient suffering from any condition that can be remedied or prevented by the methods provided herein, such as cancer. In embodiments, the cancer is a solid cancer. Exemplary conditions are cancers, such as, for example, sarcomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, brain cancer, breast cancer, ovarian cancer, prostate cancer, squamous cell cancer, head and neck cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, Hodgkin lymphoma, non-Hodgkin lymphoma, testicular cancer, lung cancer, small cell lung cancer, brain cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma (including advanced and/or metastatic), multiple myeloma, neuroblastoma, retinoblastoma and leukemias. In some particular embodiments, the cancer to be treated is a solid cancer, such as for example, breast cancer, ovarian cancer, colon cancer, prostate cancer, bone cancer, colorectal cancer, urothelial carcinoma, gastric cancer, lymphoma, malignant melanoma, liver cancer, small cell lung cancer, non-small cell lung cancer, pancreatic cancer, thyroid cancers, kidney cancer, cancer of the bile duct, brain cancer, cervical cancer, maxillary sinus cancer, bladder cancer, esophageal cancer, Merkel cell carcinoma, Hodgkin's disease and adrenocortical cancer. In some embodiments, the cancer is a locally advanced or a metastatic solid tumor malignancy. In some particular embodiments, the cancer is selected from melanoma (locally advanced or metastatic), Merkel Cell carcinoma, breast cancer including triple negative breast cancer, ovarian cancer, renal cell carcinoma, sarcoma, urothelial carcinoma, and colorectal cancer.

The present methods, kits and compositions are useful for enhancing the therapeutic effectiveness of administration of the TLR agonist, the PD-1/PD-L1 axis inhibitor, and/or the long-acting IL-2Rβ-biased agonist as a single agent. An enhanced response may be evaluated at any suitable time point during treatment, after a single round of treatment, after 2-3 cycles of treatment, etc., and by any of a number of suitable methods, including shrinkage of a tumor (partial response), i.e., an evaluation of tumor size or volume, disappearance of a tumor, a reduction in disease progression (cancer has not progressed), and analysis of one or more tumor test markers if appropriate. Particularly effective treatments will prolong survival, when evaluated at 50% maximum tumor growth, by at least 5 days, or at least 10 days, or at least 12 days, or at least 15 days, or by at least 20 days, or by at least 30 days or more.

The methods, kits, compositions, formulations, combinations, systems and the like provided herein are also useful for reducing tumor growth or size (or volume) in a subject undergoing treatment. For example, in some embodiments, one or more cycles of treatment is effective to reduce tumor size by about 25%, or by about 30%, or by about 40%, or by about 50%, or even by about 60%, or by about 70% or more, for example by about 90% or more, when compared to the size of the tumor prior to treatment.

EXAMPLES

It is to be understood that the foregoing description as well as the examples that follow are intended to illustrate and not limit the scope of the invention(s) provided herein. Other aspects, advantages and modifications within the scope of the invention will be apparent to those skilled in the art to which the invention pertains.

Materials and Methods

Recombinant human IL-2 having an amino acid sequence identical to that of aldesleukin was cloned and expressed and used to prepare the exemplary long-acting IL-2Rαβ-biased agonist referred to herein as RSLAIL-2.

RSLAIL-2 refers to a composition obtainable upon following the procedures of Example 1 in PCT Int. Pat. Appl. Pub. No. WO 2015/125159, and generically refers to a composition comprising multiPEGylated forms of IL-2, wherein attachment of the PEG reagent used to form the conjugates is releasable following administration to a subject.

4-arm-20kD-PEG-SCM corresponds to the structure:

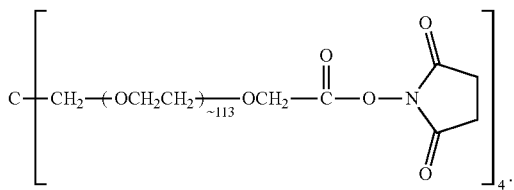

R848 (Resiquimod) has the following structure (shown as the free base):

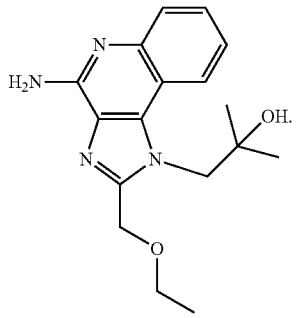 [SMILES: CCOCc1nc2c(N)nc3ccccc3c2n1CC(C)(C)O]

4-arm-PEG20kD-SCM and 4-arm-PEG40kD-SCM can be synthesized according to Example 3 of PCT Int. Pat. Appl. Pub. No. WO 2010/019233 A1.

4-arm-PEG20kD-BA can be synthesized according to Example 1 of PCT Int. Pat. Appl. Pub. No. WO 2010/019233 A1.

mPEG5kD-SC is available from NOF America Corporation, Irvine, California, USA.

4-arm-PEG20kD-SC is available from Biochempeg Scientific Inc., Watertown, Massachusetts, USA.

4-arm-PEG20kD-NCO is available from JenKem Technology, Plano, Texas, USA.

4-arm-PEG20kD-amine is available from Laysan Bio, Arab, Alabama, USA.

RMP1-14 is a purified rat immunoglobulinG2aK monoclonal antibody specific for mouse PD-1. RMP1-14 reacts with mouse PD-1 and blocks the binding of PD-1 with both of PD-L1 and PD-L2.

All non-PEG chemical reagents referred to in the examples are commercially available unless otherwise indicated. The preparation of water-soluble polymer reagents can be prepared using art-known techniques described in the literature unless otherwise indicated, or can be obtained from commercially-available sources.

Example 1

Reaction of rIL-2 with mPEG2-C2-Fmoc-20kD-NHS

Purified rIL-2 (106.4 mL) at 1.44 mg/ml was charged into a first vessel followed by the addition of 53.6 mL of formulation buffer (10 mM sodium acetate, pH 4.5, 5% trehalose). The pH was measured at 4.62 the temperature was measured at 21.2° C. The PEG reagent, C2-PEG2-FMOC-NHS-20kD (available as described in WO 2006/138572) (13.1 g), was charged into a second vessel followed by the addition of 73.3 mL of 2 mM HCl. The resulting solution was swirled by hand for 25 minutes. Sodium borate (0.5 M, pH 9.8) was added to the first vessel to raise the pH to about 9.1 and then the contents of the second vessel containing the PEG reagent was added to the first vessel over a period of from one to two minutes. A rinse step was then performed by charging 8.1 mL of 2 mM HCl into the second vessel and adding the contents to the first vessel. For the conjugation reaction, the final rIL-2 concentration was 0.6 mg/mL, the sodium borate concentration was 120 mM, the pH was 9.1+/−0.2, the temperature was 20-22° C., and the molar ratio of PEG reagent to rIL-2, after adjustment for activity of the reagent (substitution level) was 35:1. The conjugation reaction was allowed to proceed for thirty minutes and quenched by acidification by addition of 75 mL of 2N acetic acid (to bring the pH down to approximately to 4). The product was purified by ion exchange chromatography as previously described to provide a composition of primarily 4-mers, 5-mers and 6-mers (referring to the number of PEG reagents releasably covalently attached to r-IL-2 (wherein 8-mers and higher degrees of PEGylation were removed during a washing step associated with chromatography). This composition is referred to herein as "RSLAIL-2", and more particularly, as (2,7-(bis-methoxyPEG$_{10kD}$-carboxyamide)(9H-fluorene-9-yl)methyl N-carbamate)$_{4-6}$ interleukin-2.

Example 2

Receptor-Bias of RSLAIL-2 and Related Immunotherapeutic Properties

Binding Affinity to IL-2 Receptors and Receptor Bias Related to Immunostimulatory Profile: The affinity of RSLAIL-2 to IL-2Rα and IL-2Rβ was measured directly by surface plasmon resonance (Biacore T-100) and compared to that of clinically available IL-2 (aldesleukin). Antihuman antibody (Invitrogen) was coupled to the surface of a CM-5 sensor chip using EDC/NHS chemistry. Then either human IL-2Rα-Fc or IL-2Rβ-Fc fusion protein was used as the captured ligand over this surface. Serial dilutions of RSLAIL-2 and its active IL-2 conjugates metabolites (1-PEG- and 2-PEG-IL-2) were made in acetate buffer pH 4.5, starting at 5 mM. These dilutions were allowed to bind to the ligands for 5 minutes, and the response units (RU) bound was plotted against concentration to determine EC50 values. The affinities of each isoform to each IL-2 receptor subtype were calculated as fold change relative to those of IL-2.

The in vitro binding and activation profiles of RSLAIL-2 suggested that PEGylation interferes with the interaction between 1L2 and IL2Rα relative to aldesleukin; an investigation was carried out to determine whether these effects bias the profile of immune cell subtypes in vivo. The number of CD8 T and Treg cells in a tumor following administration of either RSLAIL-2 or IL2 is an important measure of whether pleiotropic effects of IL2 have been shifted due to conjugation of IL2 to poly(ethylene glycol) (as in RSLAIL-2) at the IL2/IL2Rα interface. To address the question, mice bearing subcutaneous B16F10 mouse melanoma tumors were treated with a single dose of RSLAIL-2 or 5 doses of aldesleukin, and immune cells in the tumor microenvironment were quantified by flow cytometry.

In tumors of aldesleukin-treated mice, total and memory CD8 cells were increased as a percentage of tumor-infiltrating lymphocytes; however, these effects were transient, reaching significance relative to vehicle on day 5. In contrast, significant (P<0.05) and sustained total and memory CD8 T-cell stimulation was achieved following a single RSLAIL-2 administration, with superior percentages of memory CD8 (day 7) and total CD8 (days 7 and 10) relative to aldesleukin. Both RSLAIL-2 and aldesleukin treatment resulted in increased activated natural killer (NK) cells 5 and 7 days after treatment initiation, though this effect was diminished by day 10. CD4 cell percentages of tumor-infiltrating lymphocytes were diminished following RSLAIL-2 treatment relative to vehicle on day 5. On day 10, RSLAIL-2 resulted in fewer CD4 cell percentages compared with vehicle and aldesleukin. The CD4 cell population was further analyzed for the FoxP3+ subset, which defines the Treg population. RSLAIL-2 administration reduced percentage of Tregs at every time point, consistent with reduced access to the IL2Rα subunit arising from the PEG chains. In contrast, Treg reduction with aldesleukin was modest achieving significance on day 5. The increase of CD8 T cells and reduction of Tregs led to a marked elevation of the CD8/Treg ratio in the tumor by day 7. The ratio of CD8/Treg for RSLAIL-2, aldesleukin, and vehicle was 449, 18, and 4, respectively, supporting preferential activation of the IL2 receptor beta over IL2 receptor alpha for RSLAIL-2.

Immunohistochemical staining was performed and confirmed that CD8 T cells were not only increased in number but were interspersed with tumor cells. These results indicate RSLAIL-2 is effective to induce a more robust in vivo memory effector CD8 T-cell response than seen with unmodified IL-2 (aldesleukin), without a commensurate stimulation of Tregs in tumor, consistent with an in vitro IL2Rβ-biased binding profile. That is to say, RSLAIL-2 is effective to preferentially activate and expand effector CD8+ T- and NK-cells over Tregs.

Example 3

Synthesis of an Exemplary Long-Acting TLR Agonist, 4-arm-PEG20kD-CM-N-R848 (Resiquimod) (Compound 1)

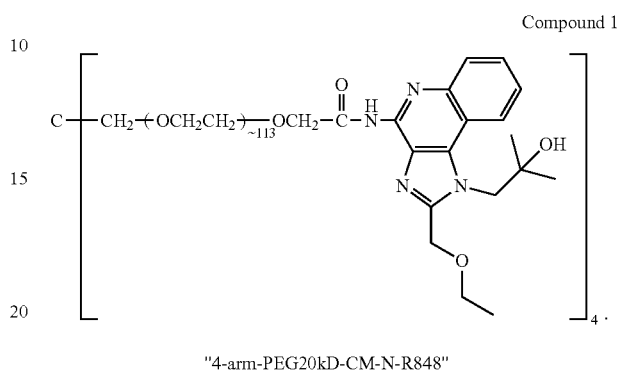

"4-arm-PEG20kD-CM-N-R848"

At 20° C., 4-arm-20kD-PEG-SCM (5.0 g, 1.0 mmol of SCM) and R848 (377 mg, 1.2 mmol) were dissolved in anhydrous DMF (25 ml). The reaction solution was stirred at 50° C. for 18 hours. The reaction solution was poured into 1 liter ethyl ether while it was being stirred. The formed precipitate was collected by filtration and washed with ethyl ether (50 ml). The obtained solid was added into isopropyl alcohol (IPA) (300 ml) and the suspension was heated up to 60° C. to form a clear solution. The solution was cooled to room temperature while being stirred. The formed precipitate was collected by filtration and washed with ethyl ether (50 ml). The purification by precipitation in IPA was repeated once and followed by drying in high vacuum overnight to give pure conjugate as a white solid (4.24 g with 5.1% wt. R848 loading). $^1$H NMR (500 MHz, Chloroform-d) δ 9.4 (broad, 0.9H), 8.22-8.14 (t, 1.8H), 7.61 (ddd, J=8.3, 7.0, 1.3 Hz, 0.9H), 7.49 (ddd, J=8.2, 7.0, 1.4 Hz, 0.9H), 4.94 (s, 1.8H), 4.80 (s, 1.8H), 3.7-3.9 (m, 460H), 1.32 (s, 5.1H), 1.25 (t, J=7.0 Hz, 2.7H).

Example 4

Synthesis of 4-arm-PEG20kD-CM-β-alanine-N-R848 (Compound 2)

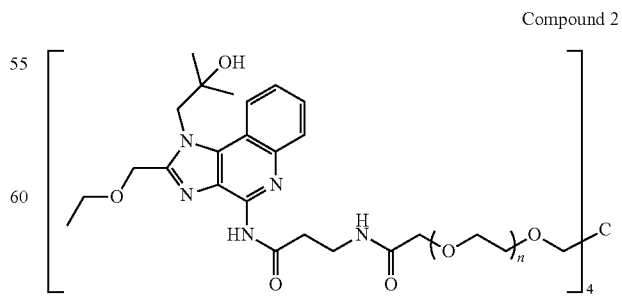

The title compound was synthesized according to the following reaction scheme.

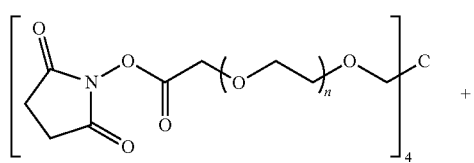

4-arm-PEG20kD-SCM

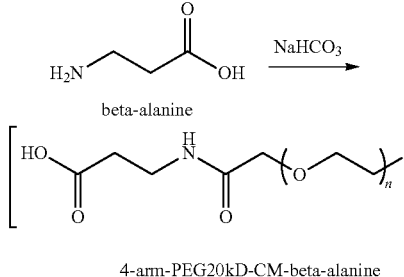

beta-alanine 4-arm-PEG20kD-CM-beta-alanine

4-arm-PEG20kD-CM-β-alanine

Beta-alanine (7.100 g, 10 equiv.) and sodium bicarbonate (6.720 g, 10 equiv.) were added into deionized water (800 ml) and the mixture was stirred to form a clear solution. 4-arm-PEG20kD-SCM (40.020 g, 1 equiv.) was added into the solution. The reaction solution was stirred at room temperature for 3 hours. 5N HCl was added into the solution to adjust the pH to 4.0. The solution was extracted with dichloromethane (150 ml) two times and the organic phase was combined and dried with anhydrous sodium sulfate. The solid was removed by running through a frit. The filtrate was condensed to 50 ml and then added to 500 ml ethyl ether to get precipitation. The product (35.050 g, yield 87%) as white powder was obtained by filtering and drying under high vacuum overnight.

$^1$H NMR (500 MHz, CDCl$_3$) δ 3.98 (s, 7.11H), 3.64 (t, 7.11H), 3.58-3.33 (m, 1818H), 3.27 (s, 7.90H), 2.40 (t, 7.11H).

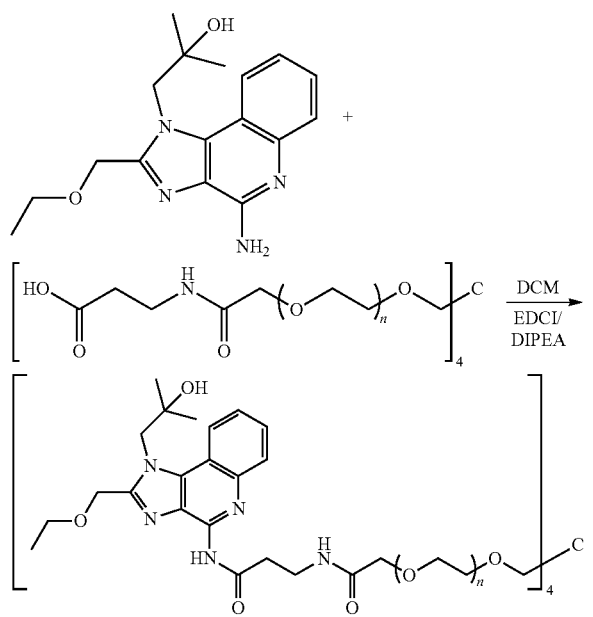

4-arm-PEG20kD-CM-β-alanine-N-R848

At 20° C., 4-arm-PEG20kD-CM-β-alanine (4.012 g, 0.8 mmol of —COOH), hydroxybenzotriazole (216 mg, 1.6 mmol), N-(3-dimethylaminopropyl)-N'-ethylcarbodiimide hydrochloride (307 mg, 1.6 mmol), and N,N-diisopropylethylamine (207 mg, 1.6 mmol) were dissolved in dichloromethane (25 ml). The mixture was stirred at room temperature for 30 minutes. R848 (302 mg, 0.96 mmol) was added and the reaction solution was stirred at 20° C. for 24 hours. The reaction solution was added into 1 liter of ethyl ether while it was being stirred. The formed precipitate was collected by filtration and washed with ethyl ether (50 ml). The obtained solid was added into isopropyl alcohol (300 ml) and the suspension was heated up to 60° C. to form a clear solution. The solution was cooled to room temperature while being stirred. The formed precipitate was collected by filtration and was washed with ethyl ether (50 ml). The purification by precipitation in isopropyl alcohol was repeated once followed by drying under high vacuum overnight to give pure conjugate as white solid (3.860 g with 5.6% w/w R848 loading).

$^1$H NMR (500 MHz, CDCl$_3$) δ 8.82 (s, 3.56H), 8.17 (d, J=8.0 Hz, 4.49H), 8.07 (d, J=8.0 Hz, 4.02H), 7.49 (t, J=7.8 Hz, 4.17H), 7.49 (t, J=7.8 Hz, 7.55H), 4.93 (s, 8.39H), 4.79 (s, 9.0H), 3.99 (s, 7.60H), 3.80-3.44 (m, 1818H), 1.33 (s) and 1.26 (t, J=7.1 Hz) (in total 34.18H).

Example 5

Synthesis of 4-arm-PEG20kD-BA-N-R848 (Compound 3)

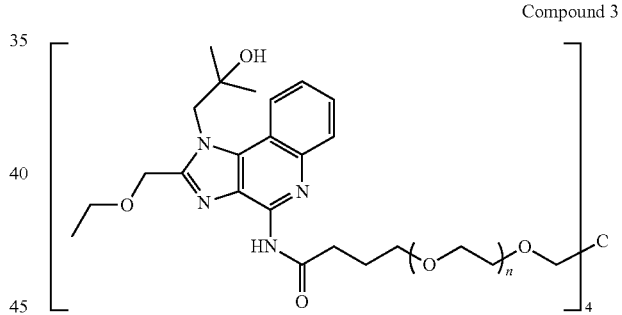

Compound 3

The title compound was synthesized according to the following reaction scheme.

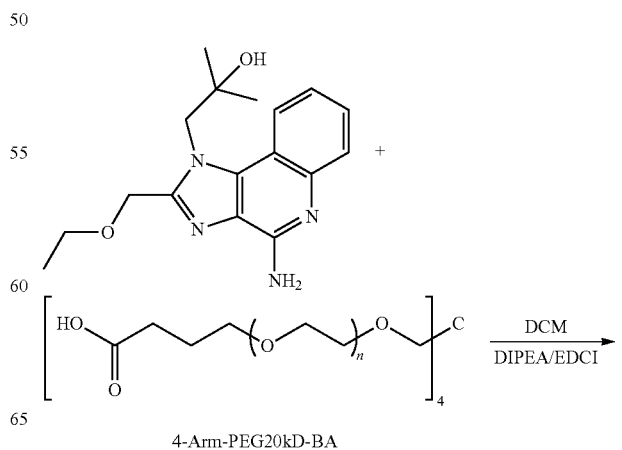

4-Arm-PEG20kD-BA

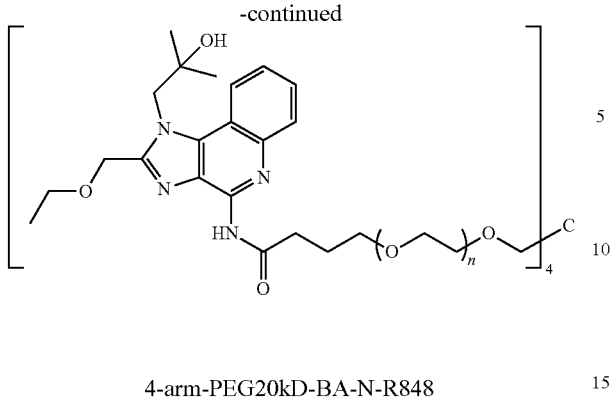

4-arm-PEG20kD-BA-N-R848

At 20° C., 4-arm-PEG20kD-BA (4.020 g, 0.8 mmol of —COOH), hydroxybenzotriazole (216 mg, 1.6 mmol), N-(3-dimethylaminopropyl)-N'-ethylcarbodiimide hydrochloride (307 mg, 1.6 mmol), and N,N-diisopropylethylamine (207 mg, 1.6 mmol) were dissolved in dichloromethane (15 ml). The mixture was stirred at room temperature for 30 minutes. R848 (302 mg, 0.96 mmol) was added and the reaction solution was stirred at 20° C. for 24 hours. The reaction solution was added into 1 liter of ethyl ether while it was being stirred. The formed precipitate was collected by filtration and was washed with ethyl ether (50 ml). The obtained solid was added into isopropyl alcohol (300 ml) and the suspension was heated up to 60° C. to form clear solution. The solution was cooled to room temperature while being stirred. The formed precipitate was collected by filtration and was washed with ethyl ether (50 ml). The purification by precipitation in isopropyl alcohol was repeated once followed by drying under high vacuum overnight to give pure conjugate as white solid (3.805 g with 5.2% w/w R848 loading).

$^1$H NMR (500 MHz, CDCl$_3$) δ 8.16 (d, J=8.5 Hz, 3.45H), 8.07 (d, J=8.5 Hz, 3.43H), 7.59 (t, J=7.8 Hz, 3.63H), 7.47 (t, J=7.8 Hz, 3.71H), 4.91 and 4.78 (s, 15.86H), 3.77-3.40 (m, 1818H), 2.10 (t, 7.30H), 1.33 (s) and 1.26 (t, J=7.1 Hz) (in total 31.34H).

Example 6

Synthesis of 4-arm-PEG20kD-CM-α-(R)-fluoro-propanamide-N-R848 (Compound 4)

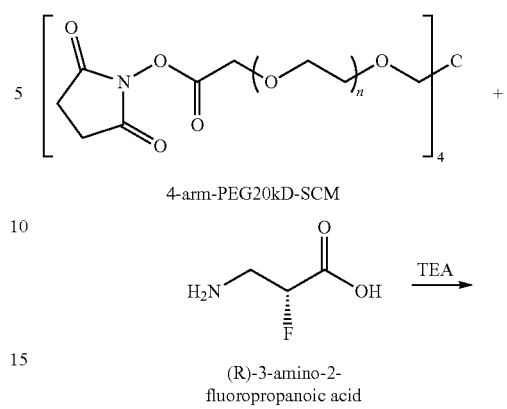

4-arm-PEG20kD-SCM (R)-3-amino-2-fluoropropanoic acid

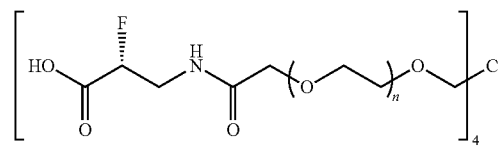

4-arm-PEG20kD-CM-α-(R)-fluoro-propanoic Acid 4-arm-PEG20kD-SCM (5.140 g, 1.03 mmol) was dissolved in dichloromethane (50 ml). (R)-3-amino-2-fluoropropanoic acid (440 mg, 4.11 mmol), and triethylamine (416 mg, 4.11 mmol) were added into N,N-dimethylformamide (5 ml) to form a suspension. The suspension was added to the 4-arm-PEG20kD-SCM in DCM solution. The reaction was stirred at 20° C. for 10 days and then diluted with water (200 ml). The aqueous solution was extracted with dichloromethane (3×100 ml). Organic phase was combined, dried with anhydrous magnesium sulfate and filtered. The filtrate was concentrated to 50 ml, which was added into ethyl ether (1 liter) to form precipitate. The precipitate was collected by filtration, which was dried under high vacuum to give 4.638 g white solid 4-arm-PEG20kD-CM-α-(R)-fluoro-propanoic acid with 70% substitution.

$^1$H NMR (500 MHz, CDCl$_3$) δ 7.49 (s, 2.77H), 5.02 (d, J=48.5 Hz, 2.77H), 4.15 (s, 3.95H), 3.65 (br, 1818H), 3.11 (q, J=7.3 Hz, 2.92H), 1.35 (t, J=7.3 Hz, 3.95H).

Compound 4

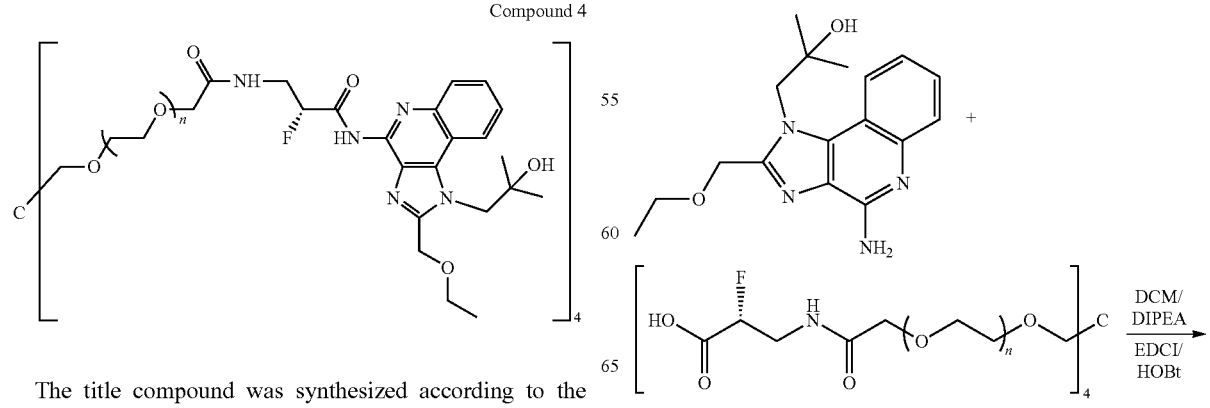

The title compound was synthesized according to the following reaction scheme.

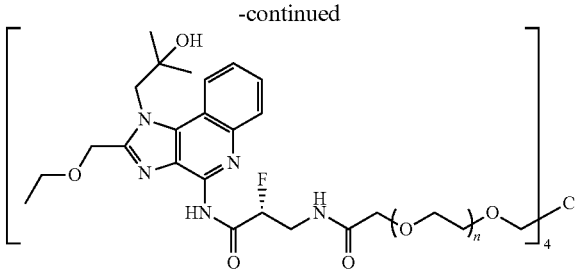

4-arm-PEG20kD-CM-α-(R)-fluoro-propanamide-N-R848

4-arm-PEG20kD-CM-α-(R)—F-propanoic acid (2.004 g, 0.4 mmol of COOH), N,N-diisopropylethylamine (207 mg, 1.6 mmol), N-(3-dimethylaminopropyl)-N'-ethylcarbodiimide hydrochloride (153 mg, 0.8 mmol), and hydroxybenzotriazole (108 mg, 0.9 mmol) were dissolved in anhydrous dichloromethane (15 ml). R848 (113 mg, 0.36 mmol) was added in 30 minutes. The reaction solution was stirred at 20° C. for 18 hours. The reaction solution was added into 1 liter of ethyl ether while being stirred. The formed precipitate was collected by filtration and was washed with ethyl ether (50 ml). The obtained solid was added into isopropyl alcohol (300 ml) and the suspension was heated up to 60° C. to form a clear solution. The solution was cooled to room temperature while being stirred. The formed precipitate was collected by filtration and was washed with ethyl ether (50 ml). The purification by precipitation in isopropyl alcohol was repeated once more and followed by drying under high vacuum overnight to give pure conjugate 1.602 g as white solid with 4.1 (w/w) % R848 loading.

$^1$H NMR (500 MHz, CDCl$_3$) δ 8.17 (s, 5.53H), 7.54 (d, J=57.7 Hz, 6.72H), 4.92 (s, 4.74H), 4.79 (s, 4.74H), 3.62 (br, 1818H), 1.5-1.0 (br., 30.0H).

Example 7

Synthesis of 4-arm-PEG40kD-CM-N-R848 (Compound 5)

Compound 5

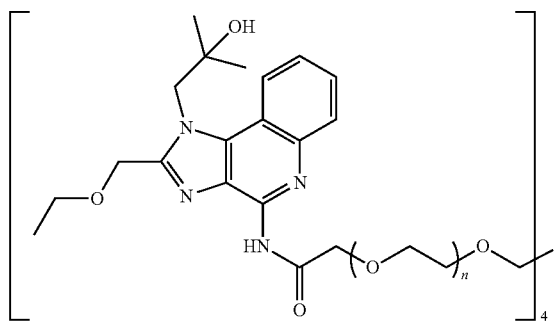

The title compound was synthesized according to the following reaction scheme.

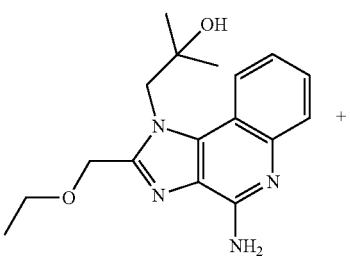

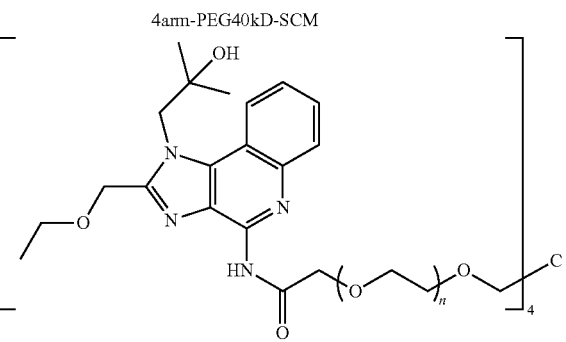

4-arm-PEG40kD-CM-N-R848

4-arm-PEG40kD-SCM (4.410 g, 0.44 mmol of SCM) was dissolved in anhydrous dichloromethane (33 ml). R848 (116 mg, 0.53 mmol) was added at room temperature. The resulting mixture solution was stirred at room temperature for 4 days. The reaction mixture was concentrated to remove the solvent. The residue was recrystallized twice with isopropyl alcohol (300 ml) as mentioned above to afford 4.262 g of product as white solid. The product contained 2.0% (w/w) R848 based on NMR analysis.

$^1$H NMR (500 MHz, CDCl$_3$) δ 8.16 (m, 5.4H), 7.58 (t, 2.8H), 7.47 (t, 2.8H), 4.92-4.70 (m, 10.6H), 4.07 (s, 1.5H), 3.88-3.45 (m, 3636H), 1.23 (s) and 1.21 (t) (total 23.6H).

Example 8

Synthesis of 4-arm-PEG20kD-CM-glycine-N-R848 (Compound 6)

Compound 6

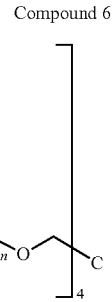

The title compound was synthesized according to the following reaction scheme.

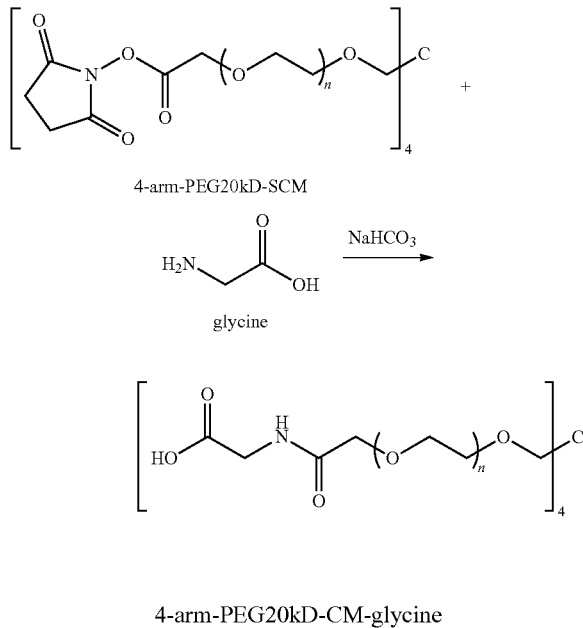

4-arm-PEG20kD-SCM glycine 4-arm-PEG20kD-CM-glycine

Glycine (6.003 g, 10 equiv.) and sodium bicarbonate (6.720 g, 10 equiv.) were added into deionized water (800 ml) and the solution was stirred until it was clear. 4-arm-PEG20kD-SCM (40.020 g, 1 equiv.) was added into the solution. The reaction solution was stirred at room temperature for 3 hours. 5N HCl solution was added into the solution to adjust the pH to 4.0. The solution was extracted with dichloromethane (2×150 ml). The organic phase was combined and dried with anhydrous sodium sulfate. The solid was removed by running through a frit. The filtrate was condensed to 50 ml and then added to 500 ml ethyl ether to obtain a precipitate. The product as white solid powder (35.050 g) was obtained by filtering and drying under high vacuum overnight.

$^1$H NMR (500 MHz, CDCl$_3$) δ 4.01 (d, 7.1H), 3.99 (s, 7.1H), 3.74-3.48 (m, 1818H), 3.35 (s, 7.1H).

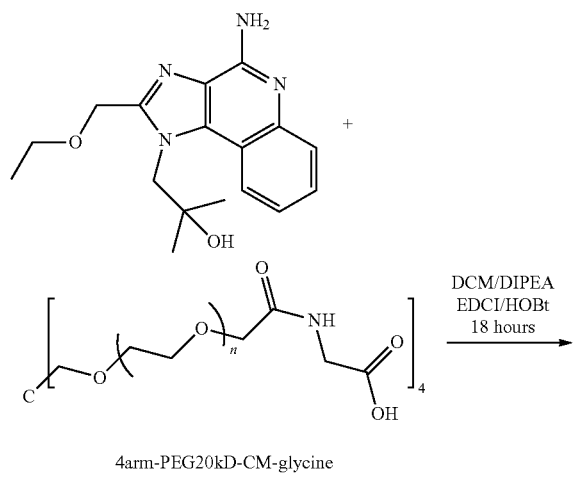

4arm-PEG20kD-CM-glycine

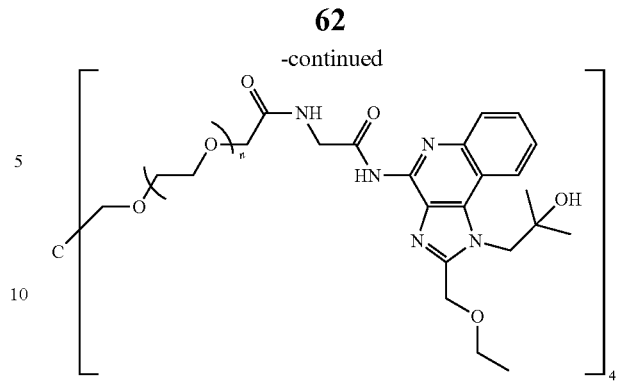

4-arm-PEG20kD-CM-Glycine-N-R848

At 20° C., 4-arm-PEG20kD-CM-Glycine (2.520 g, 0.5 mmol COOH), hydroxybenzotriazole (135 mg, 1 mmol), N-(3-dimethylaminopropyl)-N'-ethylcarbodiimide hydrochloride (192 mg, 1 mmol), and N,N-diisopropylethylamine (258 mg, 2 mmol) were dissolved in dichloromethane (15 ml). The mixture was stirred at 20° C. for 30 minutes. R848 (189 mg, 0.6 mmol) was added. The reaction solution was stirred at 20° C. for 18 hours. The reaction solution was poured into 1 liter of ethyl ether while it was being stirred. The formed precipitate was collected by filtration and was washed with ethyl ether (50 ml). The obtained solid was added into isopropyl alcohol (300 ml) and the suspension was heated up to 60° C. to form clear solution. The solution was cooled to room temperature while being stirred. The formed precipitate was collected by filtration and was washed with ethyl ether (50 ml). The purification by precipitation in isopropyl alcohol was repeated one more time followed by drying under high vacuum overnight to give pure conjugate as white solid (1.823 g with 5.1% w/w R848 loading).

$^1$H NMR (500 MHz, CDCl$_3$) δ 8.97 (s, 3.56H), 8.18 (d, J=8.5 Hz, 3.52H), 8.16-8.11 (m, 2.77H), 7.81 (s, 2.92H), 7.63 (t, J=7.8 Hz, 3.06H), 7.51 (t, J=7.8 Hz, 3.48H), 4.98 (d, J=39.6 Hz, 13.32H), 4.81 (s, 6.64H), 4.13 (s, 6.20H), 3.65 (s, 1818H), 1.34 (s, 23.63H), 1.27 (t, J=7.1 Hz, 10.59H).

Example 9

Synthesis of 4-arm-PEG20kD-CM-(L)-alanine-N-R848 (Compound 7)

Compound 7

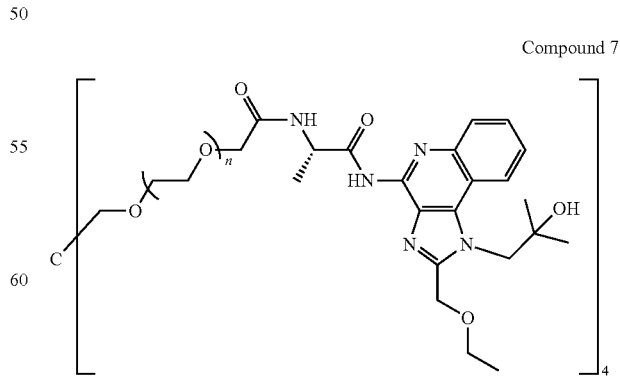

The title compound was synthesized according to the following reaction scheme.

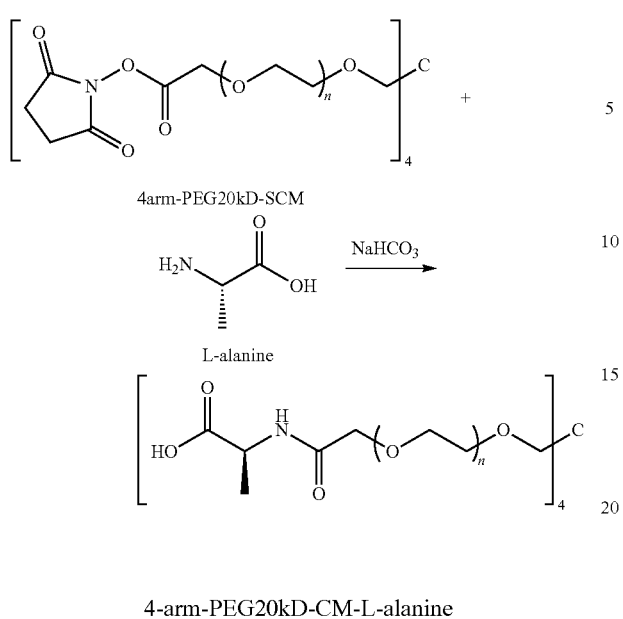

4-arm-PEG20kD-SCM

L-alanine 4-arm-PEG20kD-CM-L-alanine

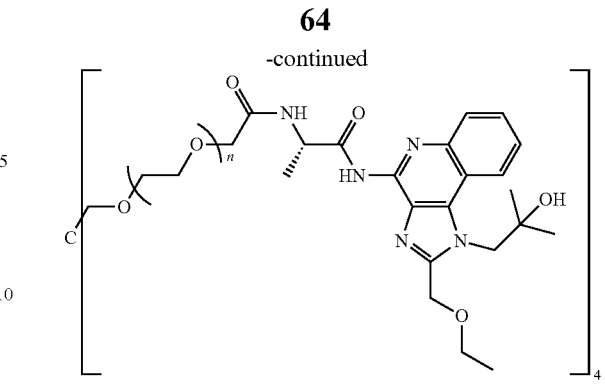

4-arm-PEG20kD-CM-L-alanine-N-R848

L-alanine (7.100 g, 10 equiv.) and sodium bicarbonate (6.720 g, 10 equiv.) were added into deionized water (800 ml) and the solution was stirred until it was clear. Then 4-arm-PEG20kD-SCM (40.030 g, 1 equiv.) was added into the solution. The reaction solution was stirred at 20° C. for 3 hours. 5N HCl solution was added into the solution to adjust pH to 4.0. The solution was extracted with dichloromethane (2×150 ml). The organic phase was combined and dried with anhydrous sodium sulfate. The solid was removed by running through a frit. The filtrate was condensed to 50 ml and then added to 500 mL ethyl ether to obtain precipitate. The product (35.012 g, yield 87%) as white solid powder was obtained by filtering and drying in vacuum overnight.

$^1$H NMR (500 MHz, CDCl$_3$) δ 4.42 (m, 3.56H), 3.85 (s, 7.11H), 3.58-3.33 (m, 1818H), 3.27 (s, 7.90H), 1.30 (d, 10.28H).

At 20° C., 4-arm-PEG20kD-CM-L-alanine (2.500 g, 0.5 mmol of COOH), N,N-diisopropylethylamine (258 mg, 2.0 mmol), N-(3-dimethylaminopropyl)-N'-ethylcarbodiimide hydrochloride (192 mg, 1.0 mmol) and hydroxybenzotriazole (135 mg, 1 mmol) were dissolved in anhydrous dichloromethane (15 ml). R848 (189 mg, 0.6 mmol) was added in 30 minutes. The reaction solution was stirred at 20° C. for 18 hours. The reaction solution was poured into 1 liter of ethyl ether while being stirred. The formed precipitate was collected by filtration and was washed with ethyl ether (50 ml). The obtained solid was added into isopropyl alcohol (300 ml) and the suspension was heated to 60° C. to form a clear solution. The solution was cooled to room temperature while being stirred. The formed precipitate was collected by filtration and was washed with ethyl ether (50 ml). The purification by precipitation in isopropyl alcohol was repeated once more and followed by drying under high vacuum overnight to give pure conjugate 1.702 g as white solid with 4.2% (w/w) R848 loading.

$^1$H NMR (500 MHz, CDCl$_3$) δ 8.14 (d, J=8.4 Hz, 5.14H), 7.69-7.54 (m, 3.95H), 7.48 (d, J=8.0 Hz, 2.37H), 4.90 (s, 4.74H), 4.78 (s, 4.74H), 3.62 (br, 1818H), 1.60 (d, J=6.9 Hz, 5.93H), 1.39 (d, J=7.3 Hz, 5.93H), 1.36-1.27 (m, 21.73H), 1.24 (d, J=6.7 Hz, 15.80H).

Example 10

The Synthesis of 4-arm-PEG20kD-CM-(L)-valine-N-R848 (Compound 8)

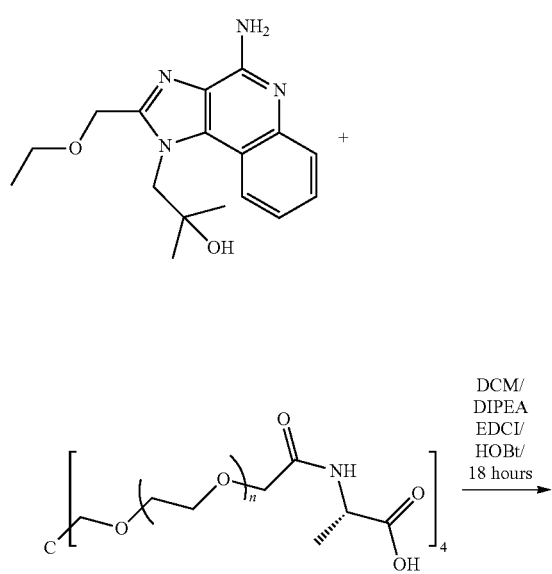

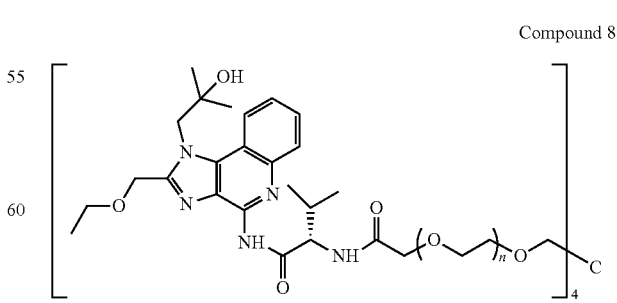

Compound 8

The title compound was synthesized according to the following reaction scheme.

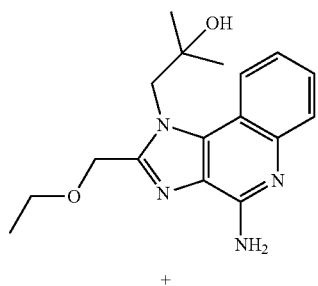

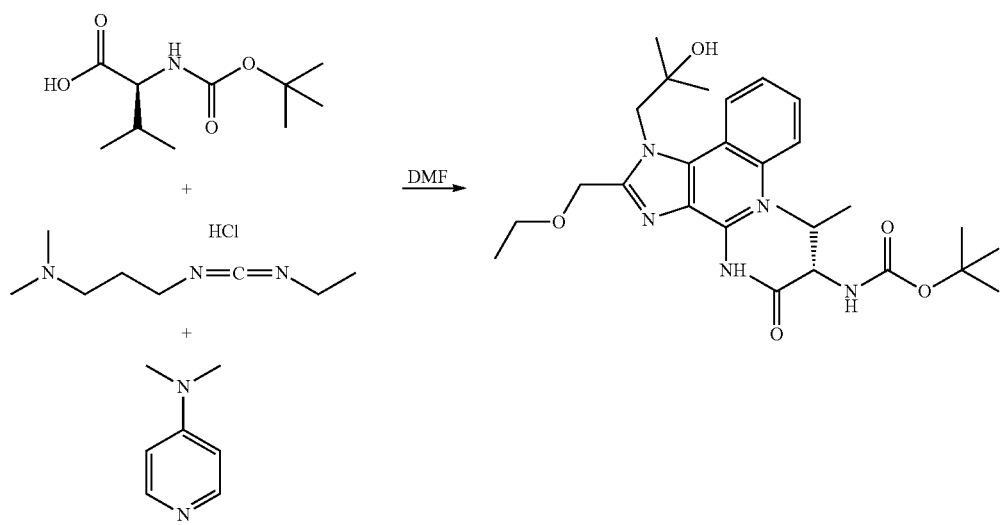

Boc-valine-R848:
1-(4-Amino-2-(ethoxymethyl)-1H-imidazo[4,5-c]quinolin-1-yl)-2-methylpropan-2-ol (R848) (237.5 mg, 0.755 mmol) was dissolved into anhydrous N,N-dimethylformamide (5 ml). Boc-L-valine (263.4 mg, 1.2 mmol) and 4-(dimethylamino)pyridine (187.4 mg, 1.534 mmol) were added. N-(3-dimethylaminopropyl)-N'-ethylcarbodiimide hydrochloride (236.1 mg, 1.232 mmol) was added. The resulting mixture was stirred at room temperature for 3 h. Water was added to quench the reaction. Brine was added. The mixture was extracted with ethyl acetate (2×50 ml). The combined organic solution was dried over anhydrous sodium sulfate, concentrated to dryness. The residue was purified with flash column chromatography on silica gel using 1-10% methanol/dichloromethane to afford product (394.7 mg) as white solid.

$^1$H-NMR (500 MHz, CDCl$_3$) δ 8.99 (br., 1H), 8.15-8.11 (m, 2H), 7.58 (t, J=7.5 Hz, 1H), 7.47 (t, J=7.5 Hz, 1H), 5.42 (m, 1H), 4.89 (br, 2H), 4.77 (s, 2H), 3.63 (q, J=7.0 Hz, 2H), 3.27 (m, 1H), 2.45 (br, 1H), 1.44 (s, 9H), 1.31 (br, 6H), 1.22 (t, J=7.0 Hz, 3H), 1.14 (br, 3H), 0.93 (d, J=6.0 Hz, 3H). LC-MS: 514 (MH$^+$/z).

Valine-R848.nTFA Salt:

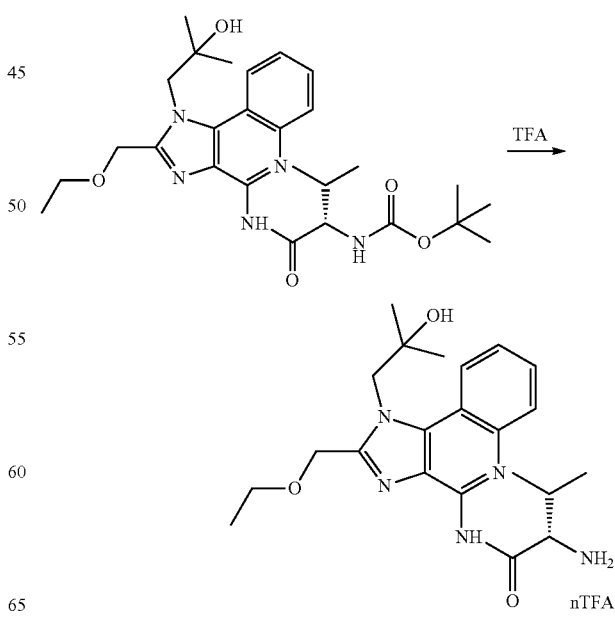

(S)-tert-butyl(1-((2-(ethoxymethyl)-1-(2-hydroxy-2-methylpropyl)-1H-imidazo[4,5-c]quinolin-4-yl)amino)-3-methyl-1-oxobutan-2-yl)carbamate (Boc-valine-R848) (377.0 mg, 0.73 mmol) was dissolved in dichloromethane (30 ml), and trifluoroacetic acid (3 ml, 38.8 mmol) was added. The resulting mixture was stirred at room temperature for 3.5 h. The mixture was concentrated to remove the solvent. The residue was dried under high vacuum to afford product (678.5 mg) as TFA salt.

LC-MS: 414 (MH+/z).

4-arm-PEG$_{20kD}$-Valine-N-R848

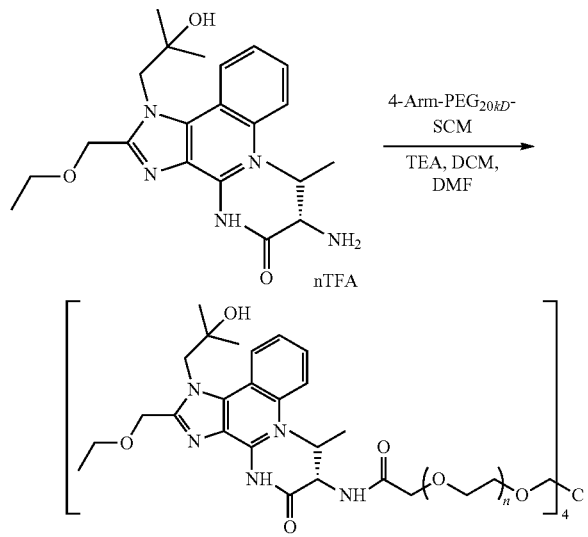

A solution of 4-arm-PEG20kD-SCM (4.170 g, 0.74 mmol of SCM) in anhydrous dichloromethane (20 ml) was added to a mixture of valine-R848.nTFA (~0.734 mmol) and triethylamine (0.3 mL, 2.15 mmol) in N,N-dimethylformamide (1.0 ml) at room temperature. Dichloromethane (~10 mL) was used to dissolve the 4-arm-PEG20kD-SCM residue in the vial and added to the reaction mixture. Triethylamine (0.15 mL, 1.076 mmol) was added. The resulting mixture was stirred at room temperature for 23 h. The reaction mixture was concentrated to remove the solvent. The residue was recrystallized with isopropyl alcohol (275 ml). The solid was washed with ethyl ether and dried under high vacuum overnight to afford 4.053 g of product as white solid. Drug loading was 4.3% (w/w).

$^1$H-NMR (500 MHz, CDCl$_3$) δ 8.99 (br), 8.10-8.09 (m, 6H), 7.54 (t, J=7.5 Hz, 3H), 7.47 (d, 3H). 7.42 (t, J=7.5 Hz, 3H), 4.840 (br, 6H), 4.712 (s, 6H), 4.07-3.95 (m, 6H), 3.72-3.42 (m, 1818H), 3.39 (m, 3H), 2.41 (br, 6H), 1.36 (br, 18H), 1.16 (t, J=6.5 Hz, 9H), 1.12 (m, 9H), 0.92 (d, J=6.0 Hz, 9H).

Example 11

Synthesis of 4-arm-PEG20kD-CM-(L)-leucine-N-R848 (Compound 9)

Compound 9

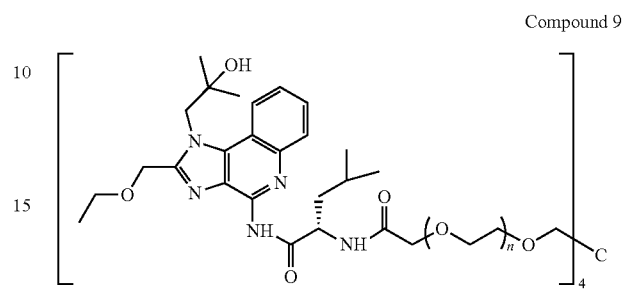

The title compound was synthesized according to the following reaction scheme.

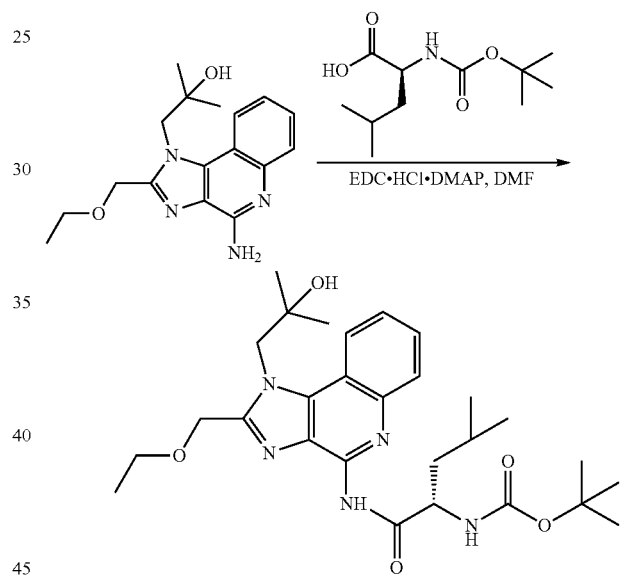

Boc-Leu-R848:

1-(4-Amino-2-(ethoxymethyl)-1H-imidazo[4,5-c]quinolin-1-yl)-2-methylpropan-2-ol (R848) (421.8 mg, 1.34 mmol) was dissolved into N,N-dimethylformamide (10 ml). Boc-Leu-OH (501.4 mg, 2.207 mmol) and 4-(dimethylamino)pyridine (344.6 mg, 2.82 mmol) were added. N-(3-dimethylaminopropyl)-N'-ethylcarbodiimide hydrochloride (438.2 mg, 2.286 mmol) was added. The resulting mixture was stirred at room temperature for 18 h. Water was added to quench the reaction. Brine was added. The mixture was extracted with ethyl acetate (2×50 ml). The combined organic solution was dried over anhydrous sodium sulfate, and concentrated to dryness. The residue was purified with flash column chromatography on silica gel using 1-10% methanol/dichloromethane to afford 494 mg of product as white solid in 70% yield.

$^1$H-NMR (500 MHz, CDCl$_3$) δ 9.03 (br, 1H), 8.16 (d, J=8.0 Hz, 1H), 8.17 (d, J=8.0 Hz, 1H), 7.57 (t, J=7.5 Hz, 1H), 7.46 (t, J=7.5 Hz, 1H), 5.26 (m, 1H), 4.85 (br, 2H), 4.77 (s, 2H), 3.63 (q, J=7.0 Hz, 2H), 3.26 (m, 1H), 1.89 (m, 2H), 1.69 (s, 3H), 1.56 (m, 1H), 1.43 (s, 9H), 1.31 (br, 3H), 1.22 (t, J=7.0 Hz, 3H), 1.08 (br, 3H), 0.94 (d, J=6.0 Hz, 3H). LC-MS: 528 (MH+/z).

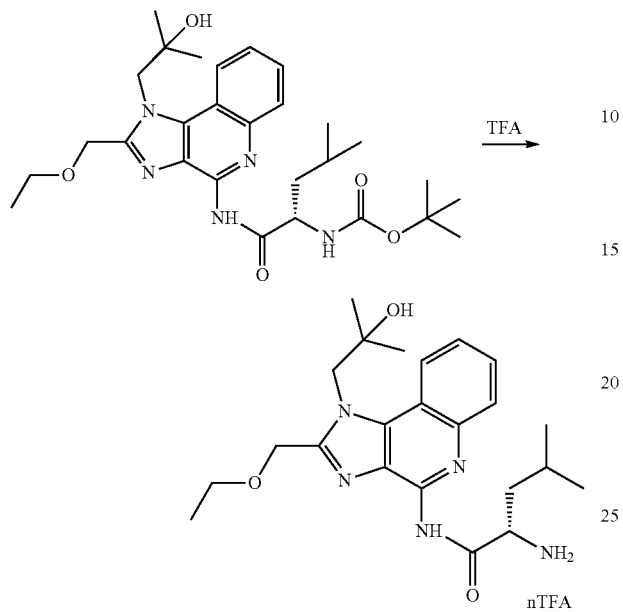

Leu-R848. nTFA salt:

(S)-tert-butyl (1-((2-(ethoxymethyl)-1-(2-hydroxy-2-methylpropyl)-1H-imidazo[4,5-c]quinolin-4-yl)amino)-4-methyl-1-oxopentan-2-yl)carbamate (Boc-Leu-R848) (494 mg, 0.936 mmol) was dissolved in dichloromethane (20 ml), and trifluoroacetic acid (3 ml, 38.8 mmol) was added. The resulting mixture was stirred at room temperature for 4 h. The mixture was concentrated to remove the solvent. The residue was dried under high vacuum to afford product (895.7 mg) as TFA salt.

LC-MS: 428 (MH+/z).

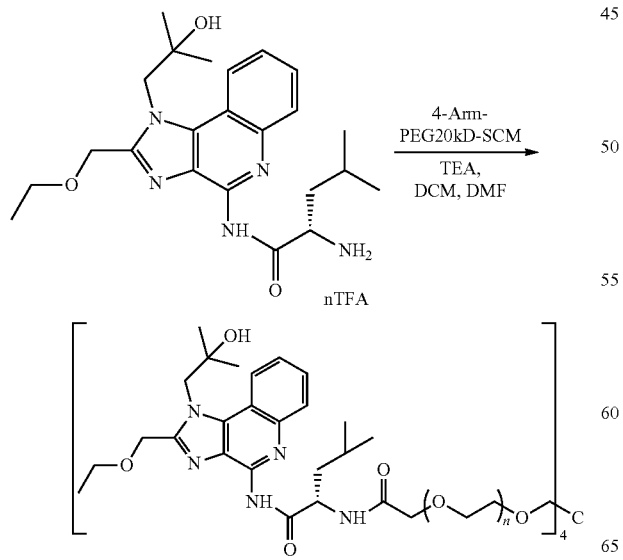

4-arm-PEG20kD-CM-L-Leucine-R848

A solution of 4-arm-PEG20kD-SCM (5.200 g, 0.96 mmol of SCM) in anhydrous dichloromethane (30 ml) was added to a solution of R848-Leu-NH₂.nTFA (~0.936 mmol) in N,N-dimethylformamide (1.0 ml) at room temperature. Dichloromethane (~10 mL) was used to dissolve the residue of 4-arm-PEG20kD-SCM in the vial, which was added to the reaction mixture. Triethylamine (0.35 ml, 2.51 mmol) was added. The resulting mixture was stirred at room temperature for 35 min. Triethylamine (0.25 ml, 1.79 mmol) was added. The mixture was stirred at room temperature for 19 h. The reaction mixture was concentrated to remove the solvent. The residue was recrystallized with isopropyl alcohol (275 ml). The solid was washed with ethyl ether and dried under high vacuum overnight to afford 5.12 g of white solid as product. Drug loading was 4% (w/w).

$^1$H-NMR (500 MHz, CDCl₃) δ 8.09-8.08 (m, 5.5H), 7.51 (t, J=7.5 Hz, 2.75H), 7.40 (m, 5.5H). 4.85 (br, 5.5H), 4.70 (s, 5.5H), 4.02-3.91 (m, 5.5H), 3.70-3.32 (m, 1818H), 1.81 (m, 2.75H), 1.72 (br, 2.75H), 1.63 (m, 2.75H), 1.22 (m, 16.5H), 1.12 (t, J=6.0 Hz, 8.25H), 0.95 (br, 8.25H), 0.86 (d, J=6.0 Hz, 8.25H).

Example 12

Synthesis of 4-arm-PEG20kD-CM-α,α-dimethyl-glycine-N-R848 (Compound 10)

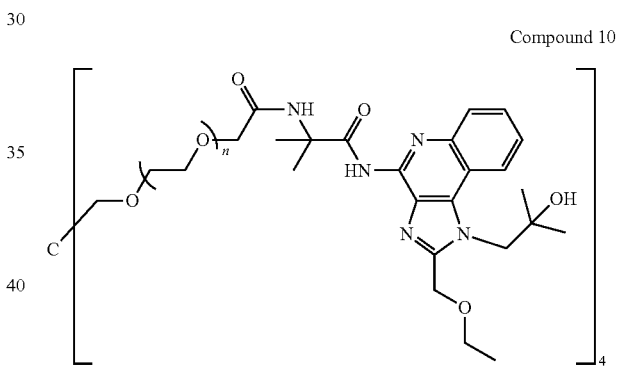

The title compound was synthesized according to the following reaction scheme.

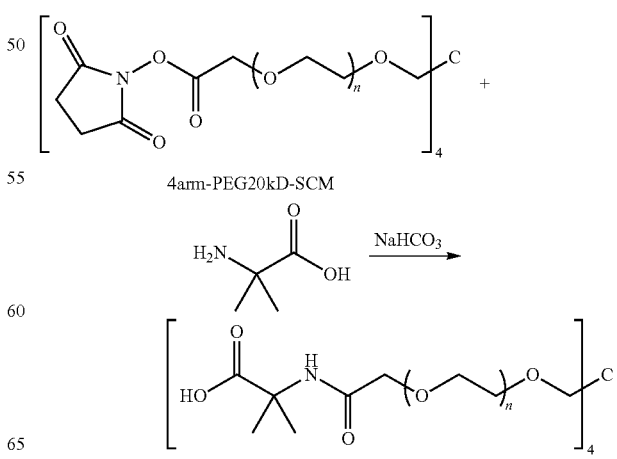

4-arm-PEG20kD-CM-α,α-dimethyl-glycine

2-Amino-2-methylpropanoic acid (2.890 g, 28 mmol) and sodium bicarbonate (2.352 g, 28 mmol) were dissolved in water (40 ml). 4-arm-PEG20kD-SCM (7.0 g, 1.4 mmol of SCM) was added in portions. The reaction mixture was stirred at 20° C. for 18 hours. The reaction was neutralized with 1M HCl (42 ml) to pH 4.7. The reaction mixture was saturated with sodium chloride and extracted with dichloromethane (3×100 ml). Organic phase was dried over anhydrous magnesium sulfate and concentrated. Residue was recrystallized with isopropyl alcohol (500 ml) to give 4.710 g white solid 4-arm-PEG20kD-CM-α,α-dimethyl-glycine with 80% substitution.

$^1$H NMR (500 MHz, CDCl$_3$) δ 7.45 (s, 3.56H), 4.15 (s, 2.77H), 3.97 (s, 2.77H), 3.64 (br, 1818H), 3.41 (s, 7.90H), 1.62 (s, 19.36H).

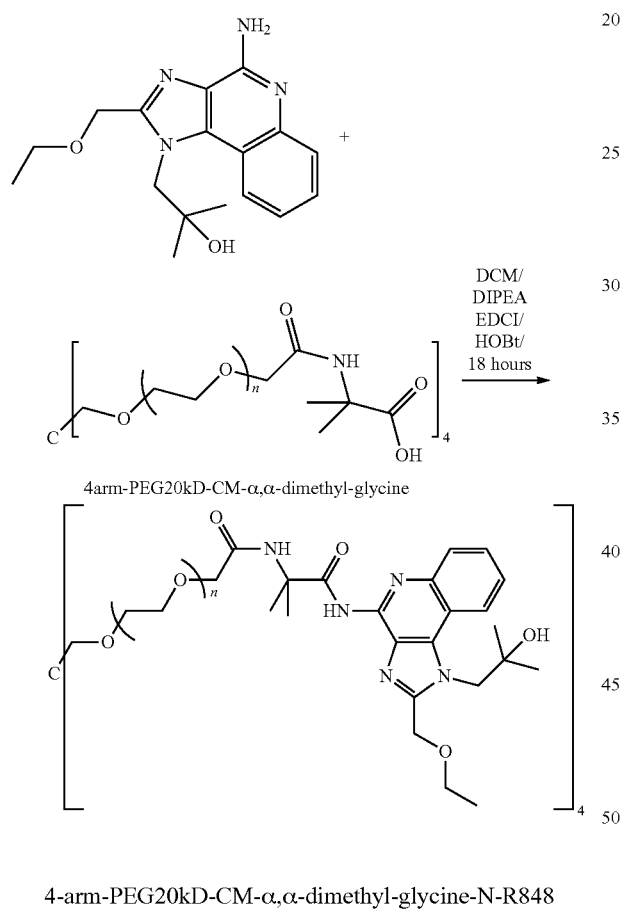

4-arm-PEG20kD-CM-α,α-dimethyl-glycine-N-R848

At 20° C., 4-arm-PEG20kD-CM-α,α-dimethyl-glycine (2.000 g, 0.43 mmol of COOH), N,N-diisopropylethylamine (258 mg, 2.0 mmol), N-(3-dimethylaminopropyl)-N'-ethylcarbodiimide hydrochloride (153 mg, 0.9 mmol), and hydroxybenzotriazole (108 mg, 0.9 mmol) were dissolved in anhydrous dichloromethane (15 ml). R848 (138 mg, 0.44 mmol) was added in 30 minutes. The reaction solution was stirred at 20° C. for 18 hours. The reaction solution was poured into 1 liter of ethyl ether while being stirred. The formed precipitate was collected by filtration and washed with ethyl ether (50 ml). The obtained solid was added into isopropyl alcohol (300 ml) and the suspension was heated up to 60° C. to form a clear solution. The solution was cooled to room temperature while being stirred. The formed precipitate was collected by filtration and washed with ethyl ether (50 ml). The purification by precipitation in isopropyl alcohol was repeated once more and followed by drying under high vacuum overnight to give pure conjugate 1.819 g as white solid with 4.7% (w/w) R848 loading.

$^1$H NMR (500 MHz, CDCl$_3$) δ 9.71 (s, 3.95H), 8.29-8.03 (m, 3.95H), 7.57 (s, 3.95H), 7.45 (s, 3.95H), 4.83 (d, J=66.8 Hz, 11.85H), 3.61 (br, 1818H), 2.50 (s, 7.90H), 1.76 (s, 11.85H), 1.42 (s, 3.95H), 1.26 (d, J=34.3 Hz, 27.65H).

Example 13

Synthesis of mPEG5kD-carbamate-N-R848 (Compound 11)

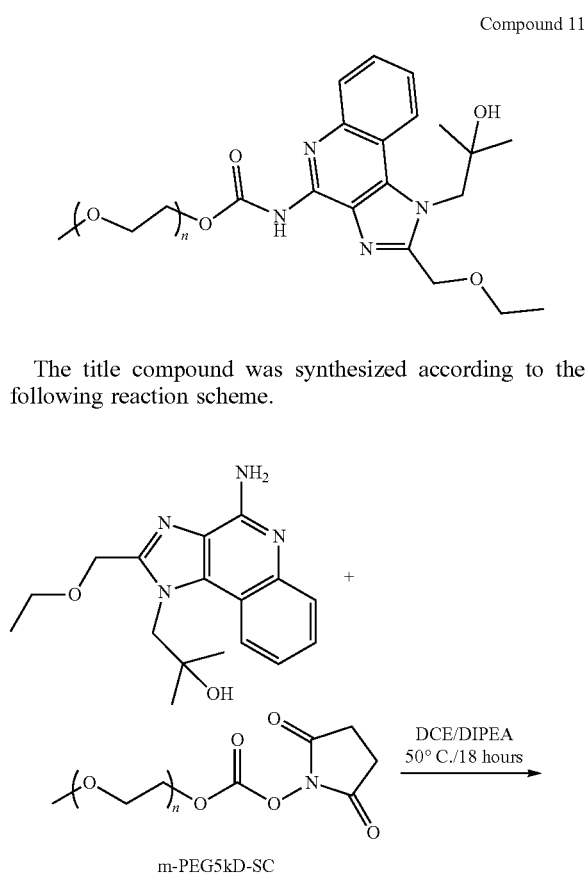

The title compound was synthesized according to the following reaction scheme.

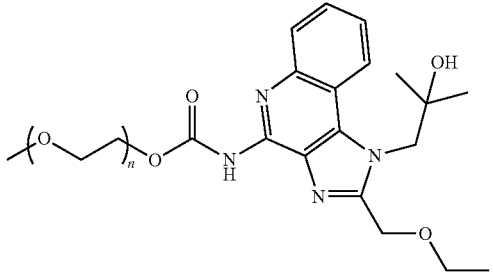

mPEG5kD-carbamate-N-R848:

At 50° C., mPEG5kD-SC (2.500 g, 0.5 mmol), R848 (236 mg, 0.75 mmol), and N, N-diisopropylethylamine (129 mg, 1.0 mmol) were dissolved in anhydrous N,N-dimethylformamide (20 ml). The reaction solution was stirred at 50° C. for 18 hours. The reaction solution was added into 1 liter of ethyl ether while being stirred. The formed precipitate was collected by filtration and was washed with ethyl ether (50 ml). The obtained solid was added into isopropyl alcohol (300 ml) and the suspension was heated up to 60° C. to form a clear solution. The solution was cooled to room temperature while being stirred. The formed precipitate was collected by filtration and was washed with ethyl ether (50 ml). The purification by precipitation in isopropyl alcohol was repeated once more and followed by drying under high vacuum overnight to give pure conjugate 2.338 g as white solid with 4.5% (w/w) R848 loading.

$^1$H NMR (500 MHz, CDCl$_3$) δ 8.18 (s, 0.77H), 8.13 (dd, J=8.4, 1.3 Hz, 0.78H), 7.59 (ddd, J=8.4, 7.0, 1.3 Hz, 0.82H), 7.49-7.44 (m, 0.82H), 4.91 (s, 1.7H), 4.78 (s, 1.7H), 4.43 (d, J=4.8 Hz, 1H), 3.63 (br, 574H), 3.37 (s, 3H), 1.32 (s, 5H), 1.25 (t, J=7.0 Hz, 2H).

Example 14

Synthesis of 4-arm-PEG20kD-carbamate-N-R848 (Compound 12)

Compound 12

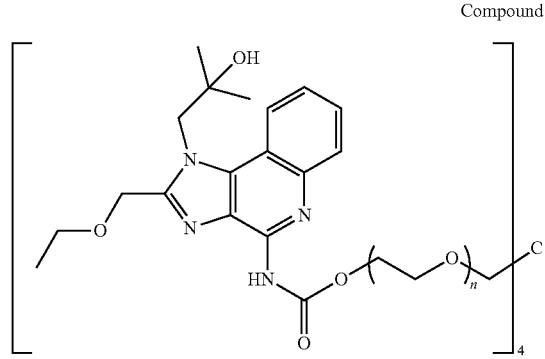

The title compound was synthesized according to the following reaction scheme.

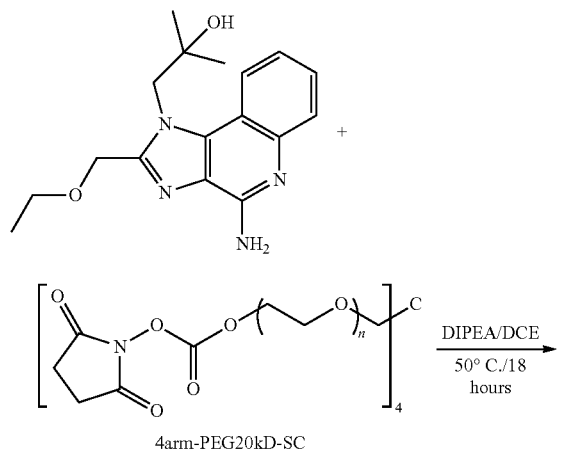

4arm-PEG20kD-SC

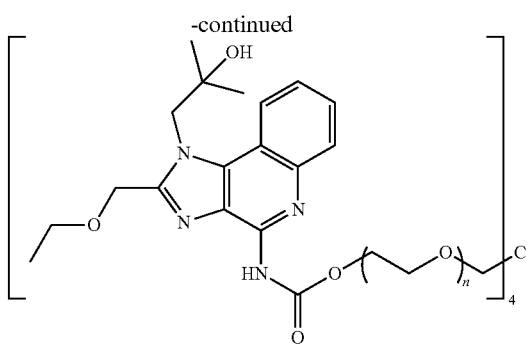

4-arm-PEG20kD-carbamate-N-R848

At 50° C., 4-arm-PEG20kD-SC (5.0 g, 1.0 mmol of SCM) and R848 (377 mg, 1.2 mmol) were dissolved in anhydrous 1,2-dichloroethane (25 ml). N,N-diisopropylethylamine (129 mg, 2 mmol) was added into the solution. The reaction solution was stirred at 50° C. for 18 hours. The reaction solution was added into 1 liter of ethyl ether while being stirred. The formed precipitate was collected by filtration and was washed with ethyl ether (50 ml). The obtained solid was added into isopropyl alcohol (300 ml) and the suspension was heated up to 60° C. to form a clear solution. The solution was cooled to room temperature while being stirred. The precipitate was formed and collected by filtration and was washed with ethyl ether (50 ml). The purification by precipitation in isopropyl alcohol was repeated once more and followed by drying under high vacuum overnight to give pure conjugate 4.240 g as white solid with 4.5% (w/w) R848 loading.

$^1$H NMR (500 MHz, CDCl$_3$) δ 8.16 (t, J=8.7 Hz, 5.93H), 7.61 (t, J=7.7 Hz, 3.16H), 7.48 (t, J=7.7 Hz, 3.16H), 4.93 (s, 2.96H), 4.80 (s, 5.93H), 4.45 (t, J=4.8 Hz, 2.96H), 3.82 (t, J=4.8 Hz, 2.96H), 3.79 (t, J=5.0 Hz, 5.93H), 3.65 (br, 1818H), 3.42 (s, 3.16H), 1.33 (s, 19.75H), 1.26 (t, J=7.0 Hz, 7.90H).

Example 15

Synthesis of 4-arm-PEG20kD-urea-N-R848 (Compound 13)

Compound 13

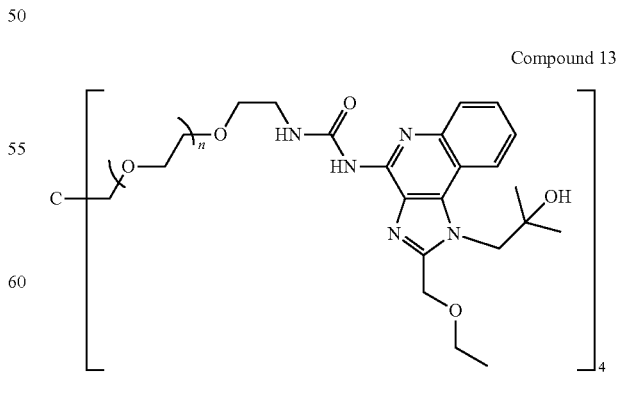

The title compound was synthesized according to the following reaction scheme.

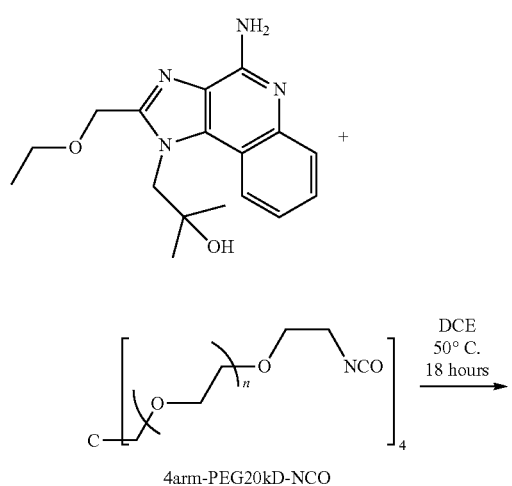

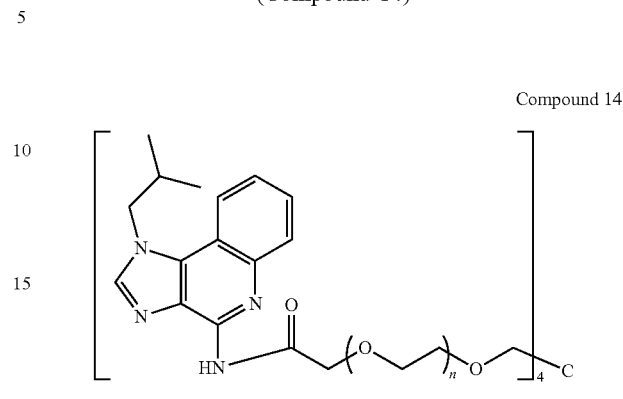

Example 16

Synthesis of 4-arm-PEG20kD-CM-imiquimod (Compound 14)

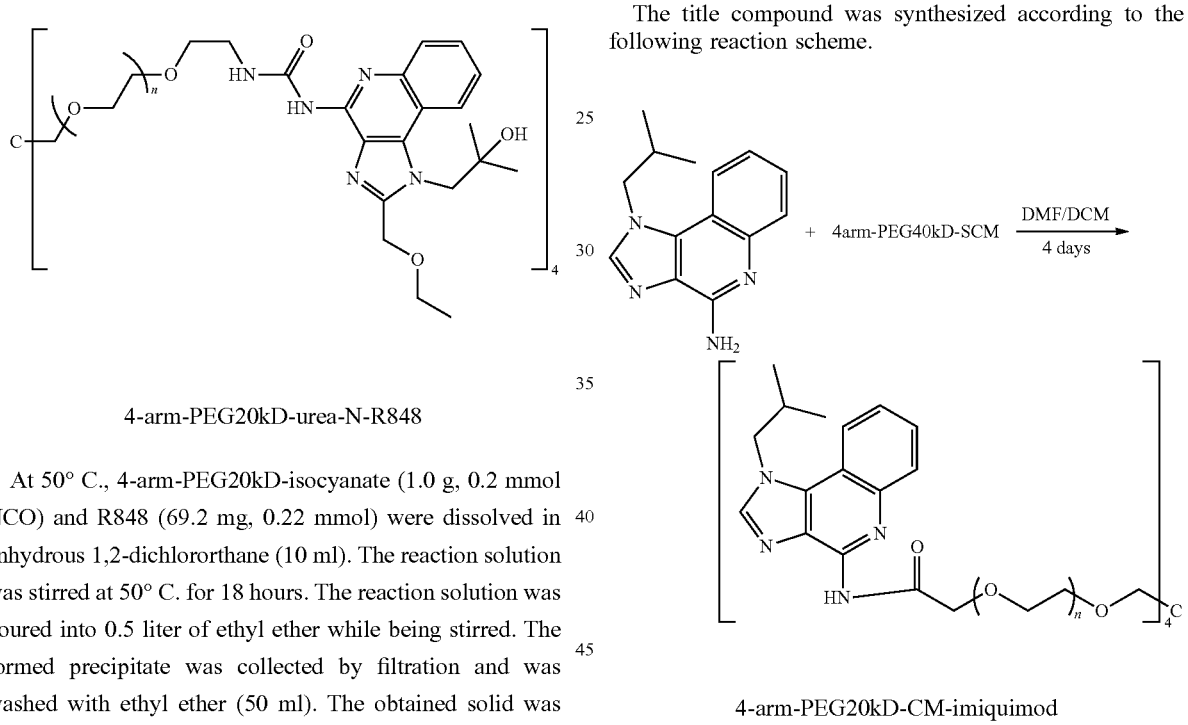

4-arm-PEG20kD-urea-N-R848

At 50° C., 4-arm-PEG20kD-isocyanate (1.0 g, 0.2 mmol NCO) and R848 (69.2 mg, 0.22 mmol) were dissolved in anhydrous 1,2-dichlororthane (10 ml). The reaction solution was stirred at 50° C. for 18 hours. The reaction solution was poured into 0.5 liter of ethyl ether while being stirred. The formed precipitate was collected by filtration and was washed with ethyl ether (50 ml). The obtained solid was added into isopropyl alcohol (250 ml) and the suspension was heated up to 60° C. to form a clear solution. The solution was cooled to room temperature while being stirred. The formed precipitate was collected by filtration and was washed with ethyl ether (50 ml). The purification by precipitation in isopropyl alcohol was repeated once more and followed by drying under high vacuum overnight to give pure conjugate as white solid 938 mg with 4.7% (w/w) R848 loading.

$^1$H NMR (500 MHz, CDCl$_3$) δ 10.30 (d, J=5.5 Hz, 3.56H), 8.17-8.09 (m, 7.11H), 7.94 (d, J=8.3 Hz, 3.56H), 7.57 (t, J=7.8 Hz, 3.56H), 7.43 (t, J=7.8 Hz, 3.56H), 4.92 (s, 7.51H), 4.77 (s, 7.51H), 3.63 (br, 1818H), 1.32 (s, 23.70H), 1.24 (t, J=7.1 Hz, 10.67H).

The title compound was synthesized according to the following reaction scheme.

4-arm-PEG20kD-CM-imiquimod 4-arm-PEG20kD-SCM (6.789 g, 1.2 mmol of SCM) was dissolved in anhydrous dichloromethane (33 ml), and then was added to a suspension of imiquimod (359.7 mg, 1.452 mmol) in N,N-dimethylformamide (5.0 ml) at room temperature. Dichloromethane (~10 mL) was used to dissolve the 4-arm-PEG20kD-SCM residue and added to the reaction mixture. The resulting mixture was stirred at room temperature for 3 days. Dichloromethane (10 ml) was added. The mixture was stirred at room temperature for another day. The reaction mixture was Concentrated to remove the solvents. The residue was recrystallized twice with isopropyl alcohol to afford 4.8612 g of product as white solid. Drug loading was 3.9% (w/w).

$^1$H NMR (500 MHz, CDCl$_3$) δ 9.55 (br, 2.5H), 8.026 (m, 3.2H), 7.853 (d, J=8.0 Hz, 3.3H), 7.720 (s, 3.3H), 7.450 (t, J=8.0 Hz, 3.3H), 7.371 (t, J=8.0 Hz, 3.3H), 4.30-4.18 (m, 13.26H), 3.471 (m, 1818H), 2.190 (m, 3.1H), 0.877 and 0.986 (2 s, 20.4H).

Example 17

Synthesis of 4-arm-PEG40kD-CM-N-imiquimod (Compound 15)

Compound 15

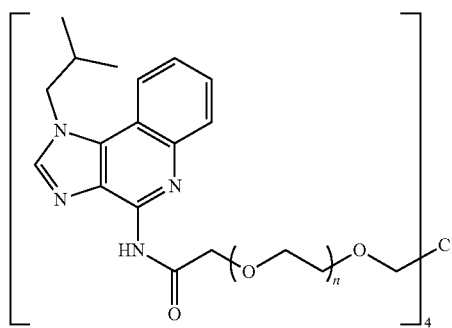

The title compound was synthesized according to the following reaction scheme.

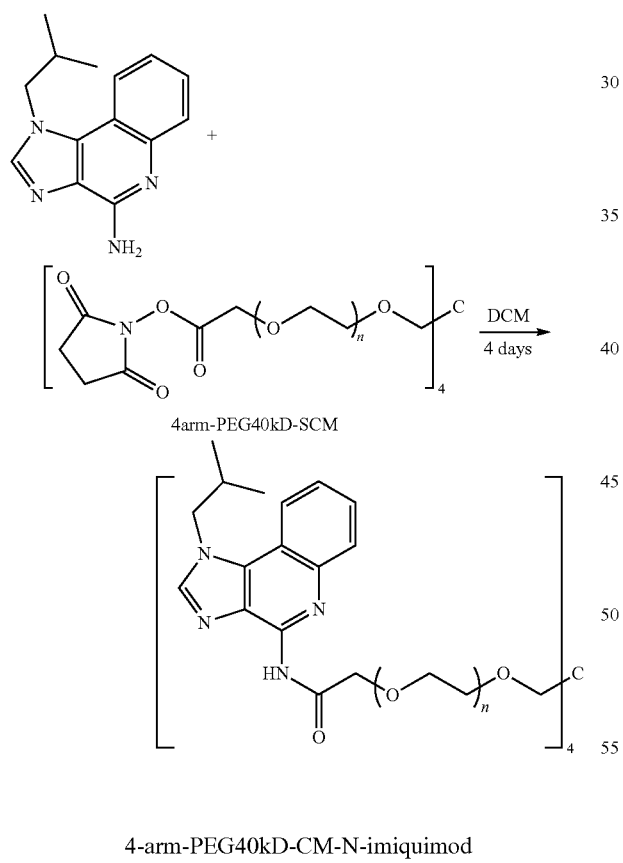

4-arm-PEG40kD-CM-N-imiquimod 4-arm-PEG40kD-SCM (5.110 g, 0.51 mmol of SCM) was dissolved in anhydrous dichloromethane (33 ml), and imiquimod (148 mg, 0.61 mmol) was added at room temperature. The resulting suspension was stirred at room temperature for 4 days to form a clear solution. The reaction mixture was concentrated to remove the solvent. The residue was recrystallized twice with isopropyl alcohol (250 ml) as mentioned above to afford 4.609 g of product as white solid. The product contained 1.8% (w/w) imiquimod based on NMR analysis.

$^1$H NMR (500 MHz, CDCl$_3$) δ 8.21 (d, 3.06H), 8.02 (d, 3.06H), 7.85 (s, 3.15H), 7.63 (t, 3.34H), 7.53 (t, 3.17H), 4.34 (d, 6.21H), 3.89-3.43 (m, 3636H), 1.03 (s, 18.09H).

Example 18

Synthesis of 4-arm-PEG20kD 4-((6-amino-8-hydroxy-2-(2-methoxyethoxy)-9H-purin-9-yl)methyl)-benzamide (Compound 16)

Compound 16

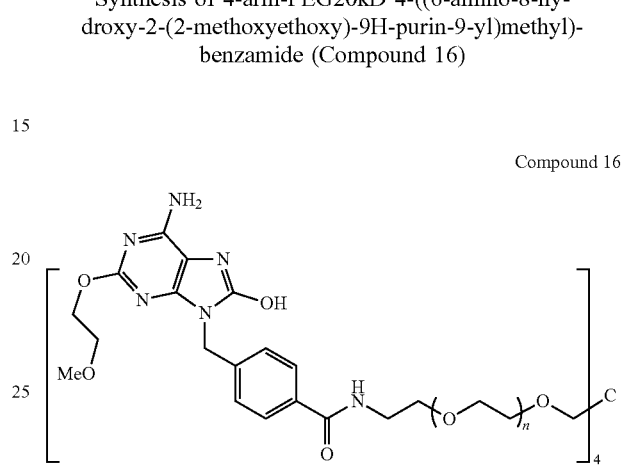

The title compound was synthesized according to the following reaction scheme.

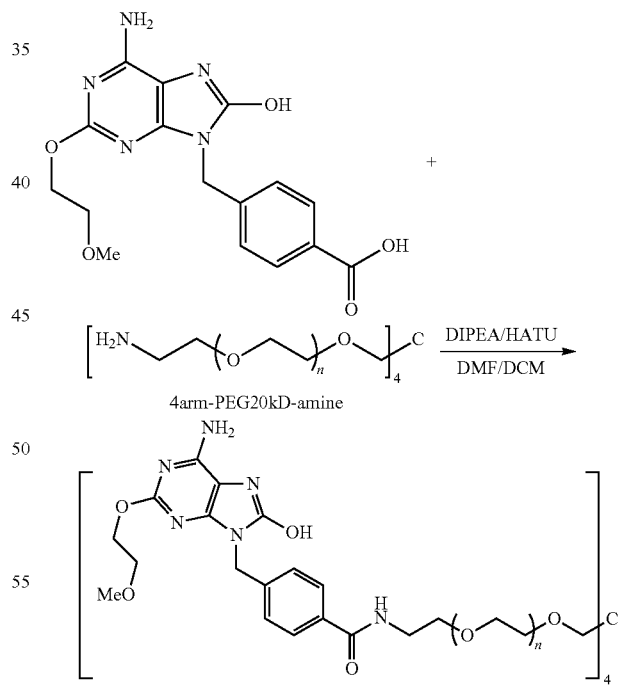

At 20° C., 4-arm-PEG20kD-amine (1.500 g, 0.3 mmol of amine) was dissolved in dichloromethane (3 ml). The solution was added into N,N-dimethylformamide (10 ml) solution containing N, N-diisopropylethylamine (116 mg, 0.9 mmol), 1-[bis(dimethylamino)methylene]-1H-1,2,3-triazolo[4,5-b]pyridinium-3-oxid hexafluorophosphate(137 mg, 0.36 mmol), and 4-((6-amino-8-hydroxy-2-(2-methoxyethoxy)-9H-purin-9-yl)methyl) benzoic acid (108 mg, 0.3 mmol). The reaction mixture was stirred at 20° C. for 18 hours. The reaction solution was added into 0.3 liter of ethyl ether while being stirred. The formed precipitate was collected by filtration and was washed with ethyl ether (50 ml). The obtained solid was purified by flash chromatography with 10-30% methanol in dichloromethane. The product was dissolved in 20 ml dichloromethane and filtered. The filtrate was concentrated and precipitated in ethyl ether again to give pure conjugate 300 mg as white solid with 6.0% (w/w) drug loading.

$^1$H NMR (500 MHz, CDCl$_3$) δ 9.26 (s, 3.95H), 7.78 (d, J=7.9 Hz, 7.90H), 7.52 (d, J=7.9 Hz, 7.90H), 5.67 (s, 7.90H), 5.04 (s, 7.90H), 4.42 (t, J=5.0 Hz, 7.90H), 3.66 (br, 1818H).

Example 19

In Vivo Study: Administration of Anti-PD1 Antibody, RSLAIL-2 and TLR-Agonist in an EMT6 Tumor Model Studies were conducted to evaluate and compare the antitumor response of a combination of an illustrative anti-PD1 antibody (RMP1-14, "aPD-1"), an exemplary long acting IL-2Rβ-biased agonist, RSLAIL-2, and an exemplary long-acting TLR-agonist, 4-arm-PEG20kD-Gly-CM-N-R848, in a murine EMT6 tumor model when compared to immunotherapy with the single agent aPD-1.

In vivo model: Mice used were ~10 weeks old female Balb/c strain with 2 million EMT6 tumor cells implanted on each flank. Cells were allowed to mature into tumors for 7 days reaching a volume of 100-150 mm$^3$ volume.

Dosing: 4-arm-PEG20kD-Gly-CM-N-R848 was dosed in 40 μl volume intra- or peritumorally (i.e., directly) to one of the two tumors (primary tumor, right flank). The contralateral side tumor (left flank) was not treated directly with the TLR-agonist, 4-arm-PEG20kD-Gly-CM-N-R848. RSLAIL-2 was dosed systemically by intravenous injection at 0.8 mg/kg. The aPD-1 was dosed systemically by intraperitoneal injection at 200 micrograms per mouse.

Group labeled: "RSLAIL-2+4-arm-PEG20kD-Gly-CM-N-R848+aPD1": mice were dosed intra-/peritumorally with 5 μg of 4arm-PEG20kD-Gly-CM-N-R848 on the first dosing day (dosing day 0) at a tumor size 100-150 mm$^3$. The same mice were also dosed intravenously with RSLAIL-2 at a dose of 0.8 mg/kg on days 0, 9 and 18 (i.e., they were dosed for a total of 3 doses, 9 days apart). The same mice were also dosed intraperitoneally with aPD-1 at a dose of 200 micrograms on days 0, 4, 9 and 13 (i.e., they were dosed for a total of 4 doses).

Group labeled: "RSLAIL-2+aPD1": mice were dosed intravenously with RSLAIL-2 at a dose of 0.8 mg/kg on days 0, 9 and 18 (i.e., they were dosed for a total of 3 doses, 9 days apart). The same mice were also dosed intraperitoneally with aPD-1 at a dose of 200 micrograms on days 0, 4, 9 and 13 (i.e., they were dosed for a total of 4 doses).

Group labeled: "4-arm-PEG20kD-Gly-CM-N-R848+aPD1": mice were dosed intra-/peritumorally with 5 μg of 4arm-PEG20kD-Gly-CM-N-R848 on the first dosing day (dosing day 0) at a tumor size 100-150 mm$^3$. The same mice were also dosed intraperitoneally with aPD-1 at a dose of 200 micrograms on days 0, 4, 9 and 13 (i.e., they were dosed for a total of 4 doses).

Group labeled: "aPD1": mice were dosed intraperitoneally with aPD-1 at a dose of 200 micrograms on days 0, 4, 9 and 13 (i.e., they were dosed for a total of 4 doses).

Group labeled "vehicle": mice were dosed intraperitumorally with 40 μl Hank's buffered saline (vehicle of 4-arm-PEG20kD-Gly-CM-N-R848) on the first dosing day (dosing day 0) at tumor size ranging from 100-150 mm$^3$. The same mice were also dosed intraperitoneally with phosphate buffered saline (aPD-1 vehicle) on days 0, 4, 9 and 13, for a total of 4 doses.

Measurements: Tumor volumes were collected by caliper measurements 2-3 times per week and calculated using the formula: L×W$^2$/2 where L is tumor length and W is tumor width.

Results: Data is provided in Table 1.

TABLE 1

Survival Proportions

| Days after treatment start | Vehicle it., i.p. | 4-arm-PEG20kD-Gly-CM-N-R848 i.p. + RSLAIL-2 i.v. + aPD-1 i.p. | RSLAIL-2 i.v. + aPD-1 i.p. | 4-arm-PEG20kD-Gly-CM-N-R848 i.p. + aPD-1 i.p. | aPD-1 i.p. |
|---|---|---|---|---|---|
| 0 | ++++ | ++++ | ++++ | ++++ | ++++ |
| 4 | ++++ | ++++ | ++++ | ++++ | ++++ |
| 7 | ++++ | ++++ | ++++ | ++++ | ++++ |
| 9 | ++++ | ++++ | ++++ | ++++ | ++++ |
| 11 | ++++ | ++++ | ++++ | ++++ | ++++ |
| 14 | ++++ | ++++ | ++++ | ++++ | ++++ |
| 16 | ++ | ++++ | ++ | ++++ | + |
| 18 | + | ++++ | ++ | ++++ | None |
| 21 | None | ++++ | ++ | ++ | |
| 23 | | ++++ | ++ | ++ | |
| 25 | | ++++ | ++ | ++ | |
| 28 | | ++++ | ++ | ++ | |
| 30 | | ++++ | ++ | None | |
| 32 | | ++++ | ++ | | |
| 35 | | ++++ | ++ | | |
| 55 | | ++++ | ++ | | |

Survival percentages are provided as follows:
0%≤+<25%
25%≤++<50%
50%≤+++<75%
75%≤++++<100%

FIG. 1 is a graph of the average tumor volume (mm$^3$) for the treatment and vehicle groups.

Single agent treatment with aPD1 leads to no long-term survival animals with tumor growth inhibition similar to no drug treatment.

Double agent treatment with aPD-1+4-arm-PEG20kD-CM-N-R848 resulted in significantly prolonged survival of 20% of the animals until day 28 of the study.

Double agent treatment with aPD-1+RSLAIL-2 resulted in long-term survival of 30% of the animals by the end of the study at day 55 after commencement of dosing. All animals in the surviving group had complete responses, both tumors were eliminated with no evidence of tumor re-growth.

Most notably, triple combination treatment with aPD-1+RSLAIL-2+4-arm-PEG20kD-CM-N-R848 resulted in survival of 80% of the animals by the end of the study at day 55 after commencement of dosing. All animals in the surviving group had complete responses, both tumors eliminated. Strikingly, both the primary and secondary tumors were eliminated over the course of treatment. That is to say, the combination treatment with aPD-1 and RSLAIL-2+4-arm-PEG20kD-CM-N-R848 not only is a significant improvement over the equivalent dose single and double agent treatments, dual combination immunotherapeutic treatment modalities, 30% survival with aPD-1+RSLAIL-2 treatment and 0% survival with aPD-1+4-arm-PEG20kD-CM-N-R848 treatment at day 55, respectively versus triple combination immunotherapy at 80% survival to at least day 55, but also resulted in the complete eradication of both the primary tumor (injected with the TLR-agonist) and the secondary tumor (no direct injection of TLR-agonist) removed from the site of the primary tumor.

The vehicle group had no surviving animals. All animals were removed from the study due to reaching limiting tumor volume between days 14 and 18 after treatment start.

INCORPORATION BY REFERENCE

All articles, books, patents, patent publications and other publications referenced herein are incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

It is claimed:

1. A kit comprising:
   (a) a PD-1/PD-L1 axis inhibitor;
   (b) a toll-like receptor (TLR) agonist covalently attached to a multi-arm, water-soluble, non-peptidic polymer, wherein the TLR agonist is selected from a multi-armed polymer conjugate of R848, a multi-armed polymer conjugate of imiquimod, or a multi-armed polymer conjugate of 44(6-amino-8-hydroxy-2-(2-methoxyethoxy)-9H-purin-9-yl)methyl)-benzamide; and
   (c) an IL-2Rβ-activating amount of a long acting interleukin-2 receptor beta (IL-2Rβ)-preferential agonist; and
instructions for their administration to a subject having a cancer.

2. The kit of claim 1, wherein the PD-1/PD-L1 axis inhibitor and the long acting IL-2Rβ-preferential agonist are formulated for parenteral administration.

3. The kit of claim 1, wherein at least one of the PD-1/PD-L1 axis inhibitor or the long acting IL-2Rβ-preferential agonist is formulated for intravenous administration.

4. The kit of claim 1, wherein the kit comprises at least the PD-1/PD-L1 axis inhibitor and the long acting IL-2Rβ-preferential agonist formulated in a single formulation.

5. The kit of claim 1, wherein the kit comprises (i) the PD-1/PD-L1 axis inhibitor and the long acting IL-2Rβ-preferential agonist formulated in a single formulation, and (ii) the toll-like receptor agonist formulated in a separate formulation.

6. The kit of claim 1, wherein each of the PD-1/PD-L1 axis inhibitor, the long-acting IL-2Rβ-preferential agonist, and the TLR agonist is in a solid form suitable for reconstitution in an aqueous diluent.

7. The kit of claim 1, wherein the toll-like receptor agonist is formulated for intratumoral injection or peritumoral injection.

8. The kit of claim 1, wherein the PD-1/PD-L1 axis inhibitor is selected from atezolizumab, avelumab, durvalumab, nivolumab, pembrolizumab, or BGB-A317.

9. The kit of claim 1, wherein the long acting IL-2Rβ-preferential agonist is selected from multi(2,7-(bis-methoxyPEG-carboxyamide)(9H-fluorene-9-yl)methyl N-carbamate)interleukin-2, (2,7-(bis-methoxyPEG$_{10\ kD}$-carboxyamide)(9H-fluorene-9-yl)methyl N-carbamate)$_{4-6}$interleukin-2, or (2,7-(bis-methoxyPEG-carboxyamide)(9H-fluorene-9-yl)methyl N-carbamate)$_{6\ avg}$interleukin-2.

10. The kit of claim 1, wherein the TLR agonist is selected from 4-arm-PEG20kD-CM-imiquimod, 4-arm-PEG20kD-CM-glycine-N-imiquimod, 4-arm-PEG20kD-CM-N-R848, 4-arm-PEG20kD-CM-glycine-N-R848, Compound 1

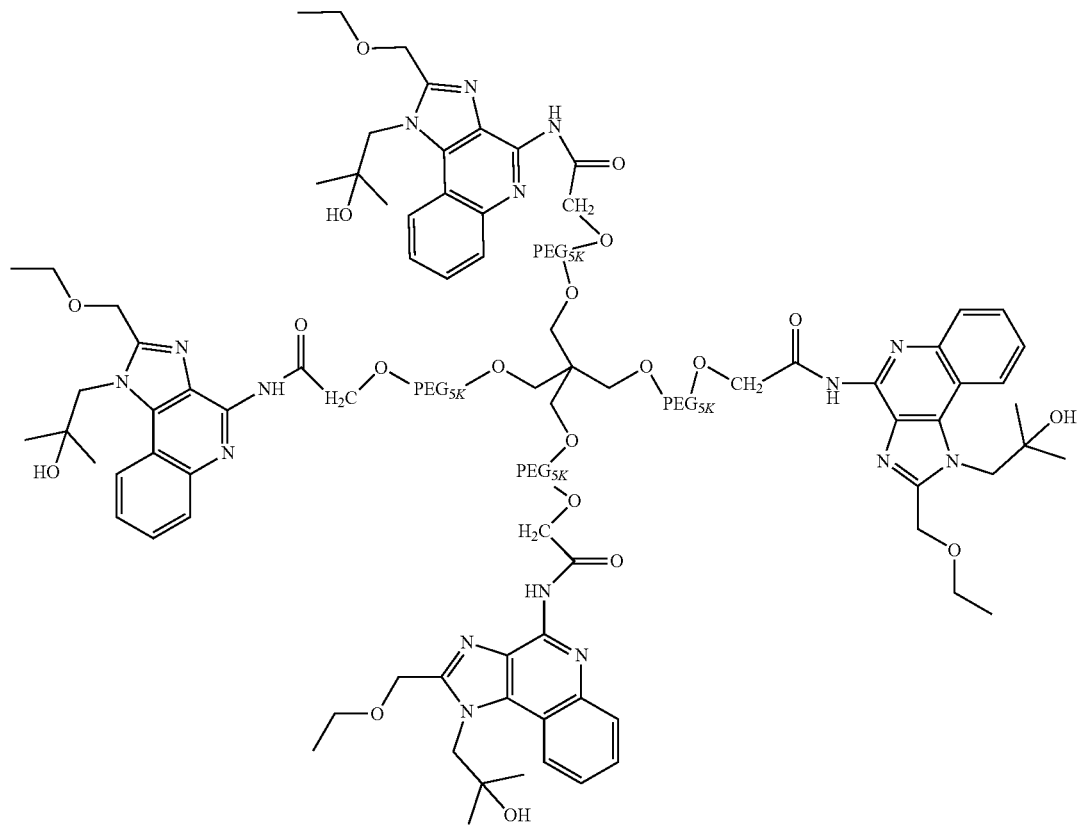

-continued
Compound 2
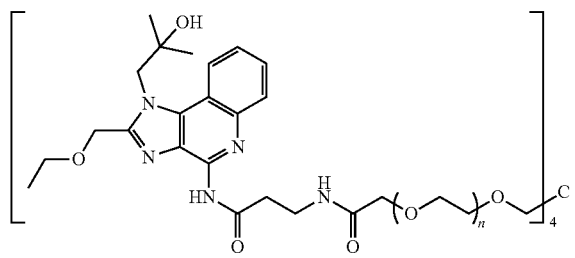
Compound 3
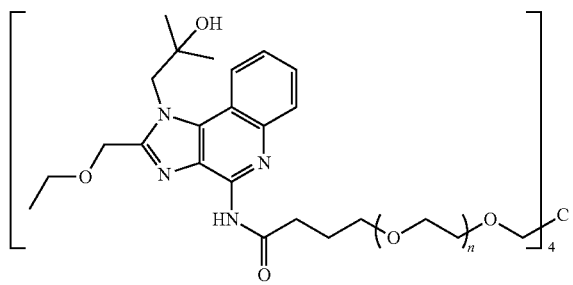
Compound 4
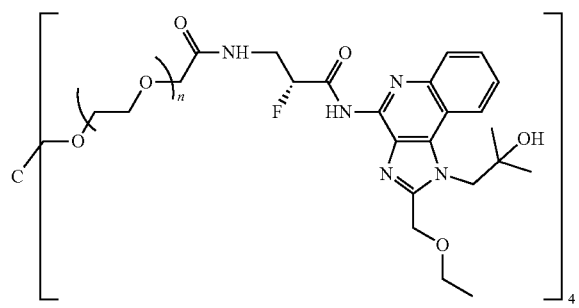
Compound 5
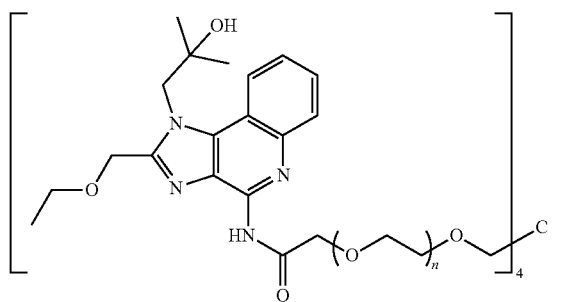
Compound 6
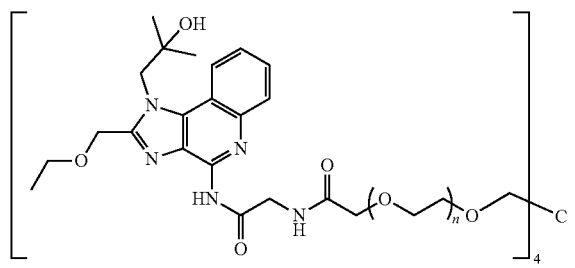
Compound 7
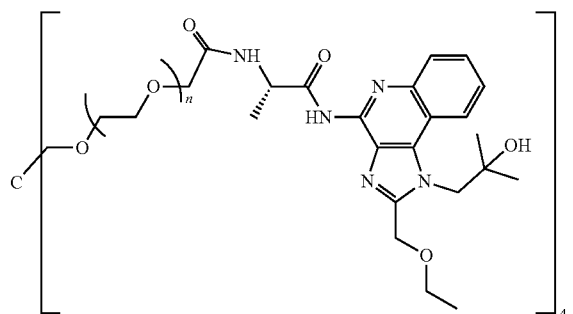
Compound 8
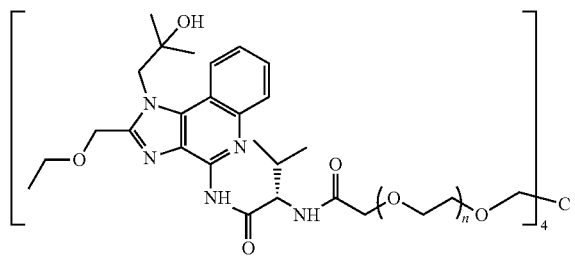
Compound 9
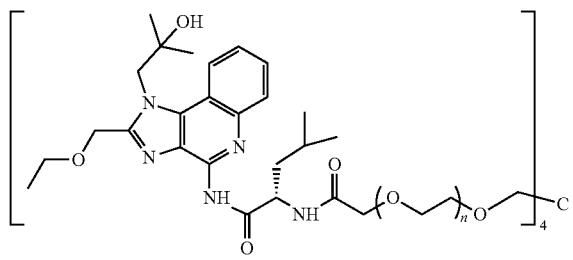
Compound 10
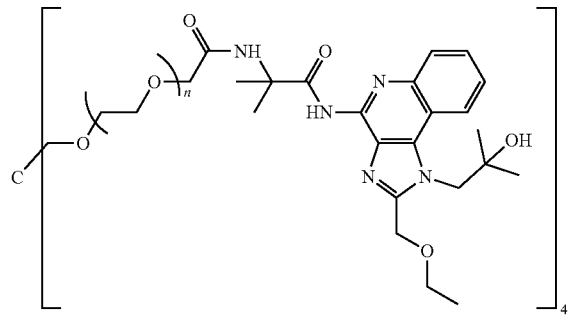
Compound 12
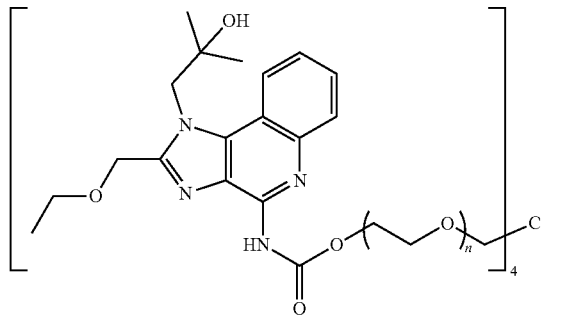

Compound 13

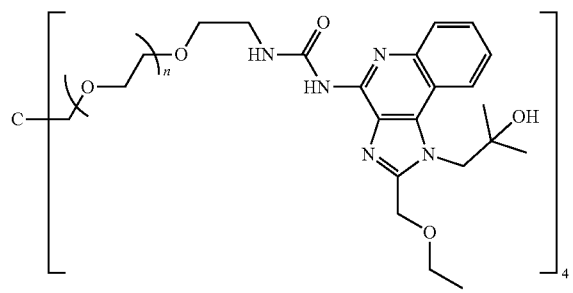

Compound 14

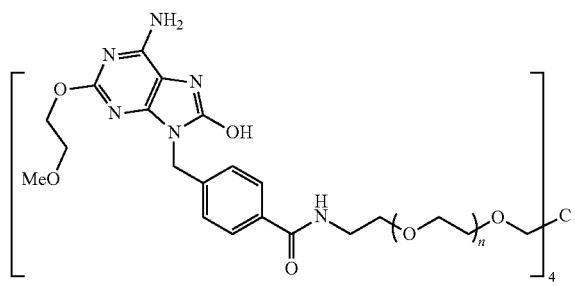

Compound 15

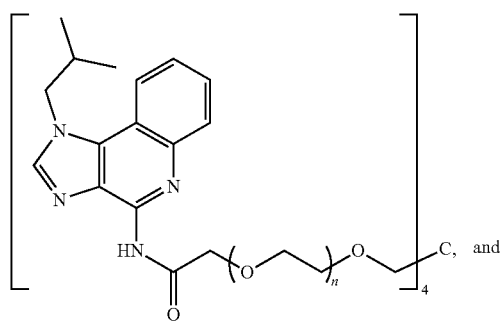

Compound 16 or a pharmaceutically acceptable salt thereof, wherein each n for each of Compounds 1-10 and 12-16 is independently an integer from 40 to 350.

11. A method of treating a subject having a cancer, the method comprising: (a) administering to the subject having a cancer an effective amount of a PD-1/PD-L1 axis inhibitor; (b) administering to the subject an effective, IL-2Rβ-activating amount of a long acting interleukin-2 receptor beta (IL-2Rβ)-preferential agonist, wherein the long acting IL-2Rβ-preferential agonist is selected from multi(2,7-(bis-methoxyPEG-carboxyamide)(9H-fluorene-9-yl)methyl N-carbamate)interleukin-2,(2,7-(bis-methoxyPEG$_{10\ kD}$-carboxyamide)(9H-fluorene-9-yl)methyl N-carbamate)$_{4-6}$interleukin-2, or (2,7-(bis-methoxyPEG-carboxyamide)(9H-fluorene-9-yl)methyl N-carbamate)6$_{avg}$interleukin-2; and (c) administering to the subject an effective amount of a toll-like receptor (TLR) agonist covalently attached to a multi-arm, water-soluble, non-peptidic polymer, wherein the TLR agonist is selected from a multi-armed polymer conjugate of R848, a multi-armed polymer conjugate of imiquimod, or a multi-armed polymer conjugate of 4-((6-amino-8-hydroxy-2-(2-methoxyethoxy)-9H-purin-9-yl)methyl)-benzamide.

12. The method of claim 11, wherein each of the PD-1/PD-L1 axis inhibitor, the toll-like receptor agonist and the long acting IL-2Rβ-preferential agonist are administered at substantially the same time.

13. The method of claim 11, wherein the PD-1/PD-L1 axis inhibitor is administered separately from at least one of the toll-like receptor agonist or the long acting IL-2Rβ-preferential agonist.

14. The method of claim 11, wherein each of the PD-1/PD-L1 axis inhibitor and the long acting IL-2Rβ-preferential agonist are administered at substantially the same time.

15. The method of claim 11, wherein each of the PD-1/PD-L1 axis inhibitor and the toll-like receptor agonist are administered at substantially the same time.

16. The method of claim 11, wherein the toll-like receptor agonist is administered separately from at least one of the PD-1/PD-L1 axis inhibitor or the long acting IL-2Rβ-preferential agonist.

17. The method of claim 11, wherein administering steps (a) and (b) both comprise parenteral administering.

18. The method of claim 11, wherein the toll-like receptor agonist is administered by a method selected from intratumoral injection and peritumoral injection.

19. The method of claim 11, wherein the PD-1/PD-L1 axis inhibitor is an anti-PD-1 antibody.

20. The method of claim 19, wherein the anti-PD-1 antibody is selected from atezolizumab, avelumab, durvalumab, nivolumab, pembrolizumab, or BGB-A317.

21. The method of claim 11, wherein the TLR agonist is selected from 4-arm-PEG20kD-CM-imiquimod, 4-arm-PEG20kD-CM-glycine-N-imiquimod, 4-arm-PEG20kD-CM-N-R848, 4-arm-PEG20kD-CM-glycine-N-R848, Compound 1
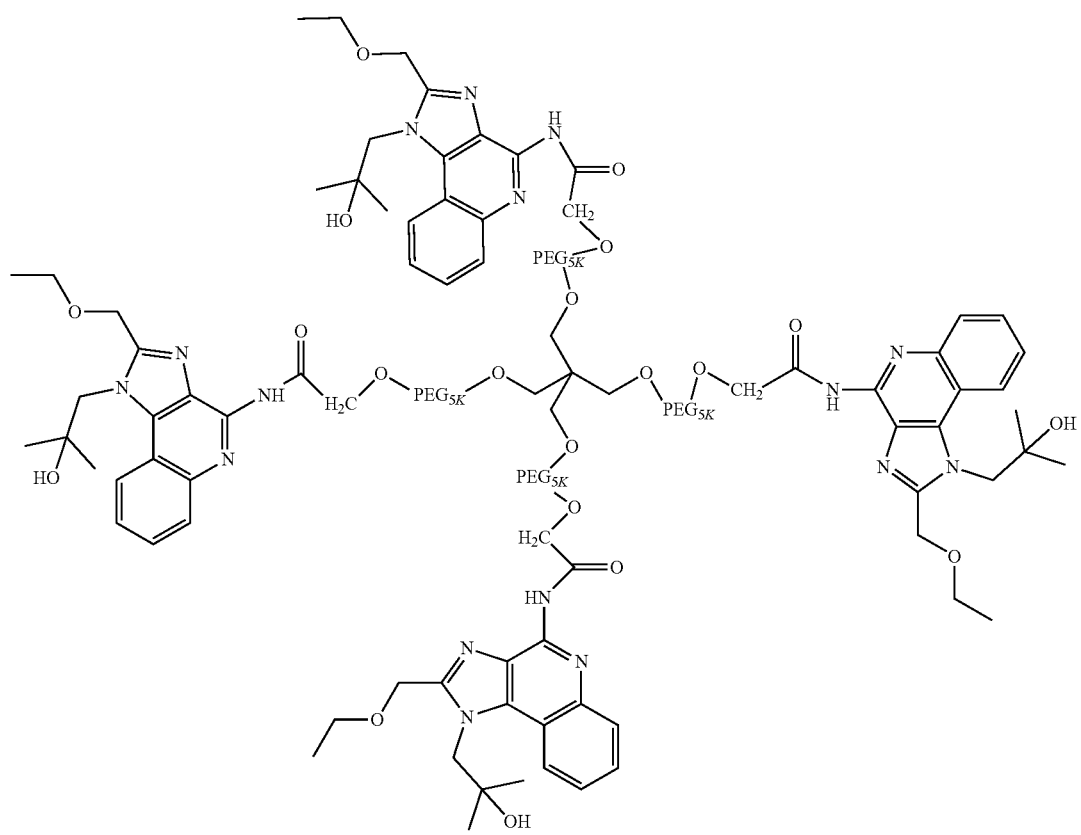
Compound 2
Compound 3
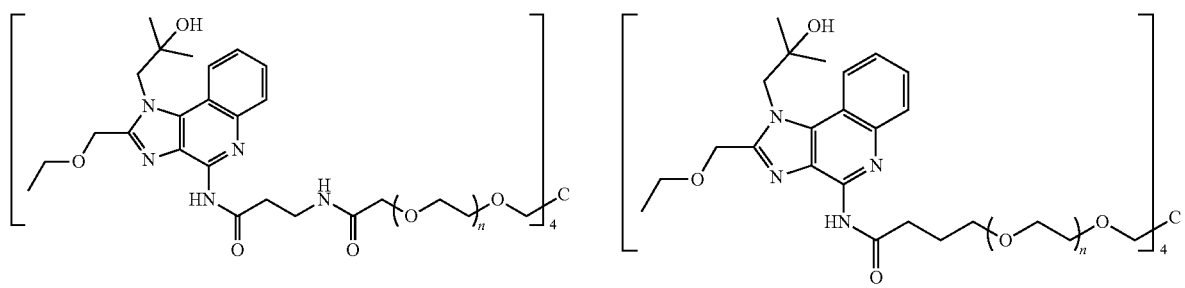
Compound 4
Compound 5
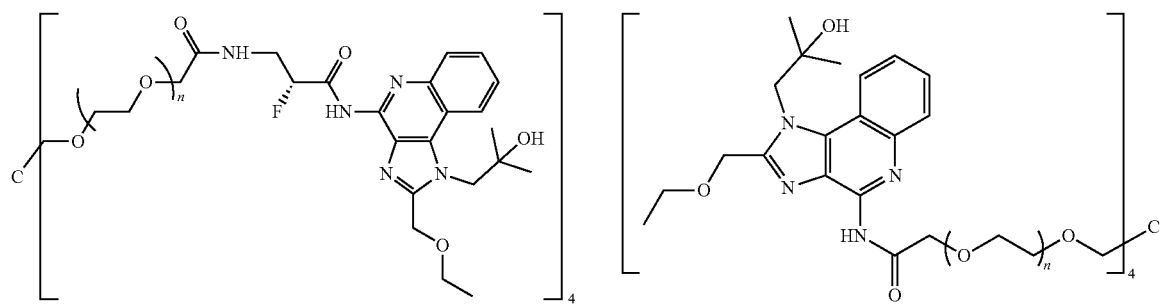

-continued
Compound 6
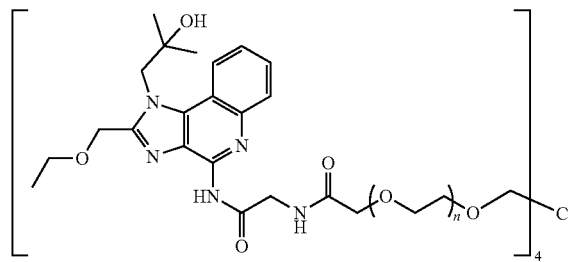
Compound 8
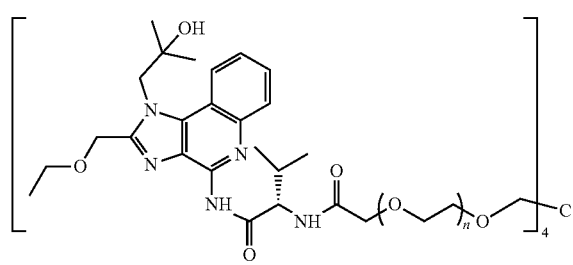
Compound 10
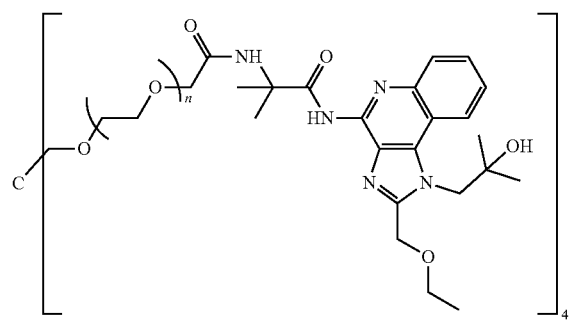
Compound 13
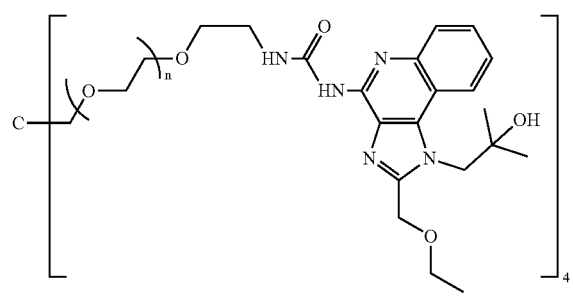
Compound 15
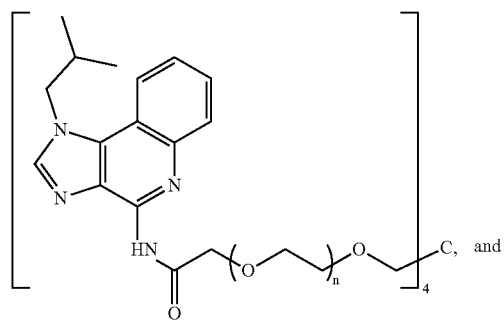
Compound 7
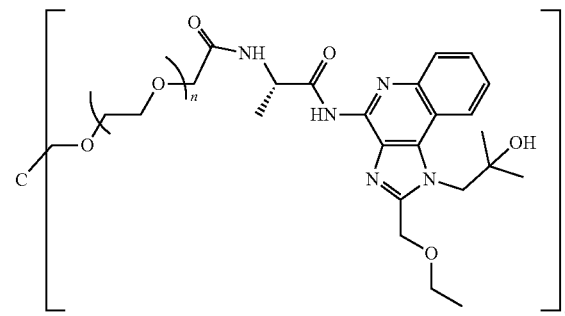
Compound 9
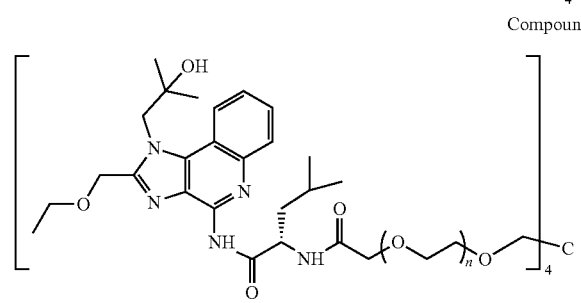
Compound 12
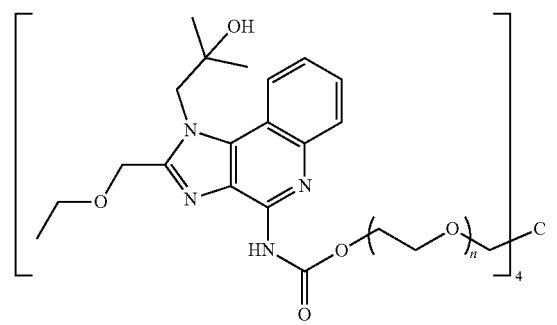
Compound 14
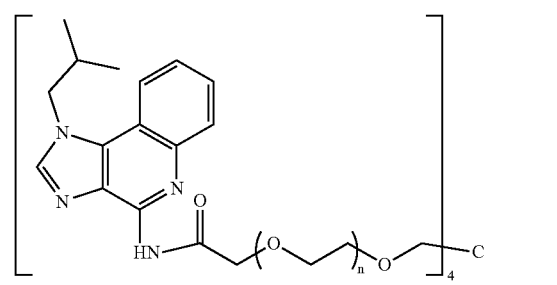
Compound 16
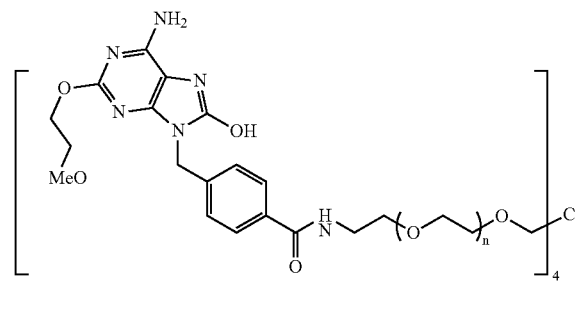

or a pharmaceutically acceptable salt thereof, wherein each n for each of Compounds 1-10 and 12-16 is independently an integer from 40 to 350.

22. The method of claim 11, wherein the cancer is a solid cancer.

23. The method of claim 22, wherein the cancer is selected from breast cancer, ovarian cancer, colon cancer, prostate cancer, bone cancer, colorectal cancer, gastric cancer, lymphoma, malignant melanoma, liver cancer, small cell lung cancer, non-small cell lung cancer, pancreatic cancer, thyroid cancers, kidney cancer, cancer of the bile duct, brain cancer, cervical cancer, maxillary sinus cancer, bladder cancer, esophageal cancer, Hodgkin's lymphoma or adrenocortical cancer.

24. The method of claim 11, wherein administration of the PD-1/PD-L1 axis inhibitor, the IL-2Rβ-activating amount of the long acting IL-2Rβ-preferential agonist, and the toll-like receptor agonist is effective to promote activation of the immune system.

25. The method of claim 11, wherein administration of the PD-1/PD-L1 axis inhibitor, the IL-2Rβ-activating amount of the long acting IL-2Rβ-preferential agonist, and the toll-like receptor agonist is effective to (i) promote activation of at least one of CD8 T cells, CD11c+ and CD8+dendritic cells, and neutrophils, and (ii) stimulate T cells.

26. The method of claim 11, wherein administration of the PD-1/PD-L1 axis inhibitor, the IL-2Rβ-activating amount of the long acting IL-2Rβ-preferential agonist, and the toll-like receptor agonist is effective to suppress T regulatory cells, macrophages, and monocytes.

27. The method of claim 11, wherein administration of the PD-1/PD-L1 axis inhibitor, the IL-2Rβ-activating amount of the long acting IL-2Rβ-preferential agonist, and the toll-like receptor agonist is effective to produce an abscopal effect on the cancer.

28. The method of claim 11, wherein step (a) is carried out before, after, or simultaneously with step (b).

* * * * *